US008762169B2

(12) United States Patent
Mohlenbrock et al.

(10) Patent No.: US 8,762,169 B2
(45) Date of Patent: Jun. 24, 2014

(54) MEDICAL VALUE INDEX

(71) Applicant: Verras, Ltd., Palo Alto, CA (US)

(72) Inventors: William C. Mohlenbrock, Carlsbad, CA (US); Timothy M. Breen, San Jose, CA (US)

(73) Assignee: Verras Healthcare International, LLC

( * ) Notice: Subject to any disclaimer, the term of this patent is extended or adjusted under 35 U.S.C. 154(b) by 0 days.

(21) Appl. No.: 14/017,919

(22) Filed: Sep. 4, 2013

(65) Prior Publication Data
US 2014/0081664 A1 Mar. 20, 2014

Related U.S. Application Data

(63) Continuation-in-part of application No. 13/289,284, filed on Nov. 4, 2011, now abandoned.

(51) Int. Cl.
*G06Q 10/00* (2012.01)
*G06Q 50/00* (2012.01)
*A61B 5/00* (2006.01)
*G06F 19/00* (2011.01)

(52) U.S. Cl.
USPC .................................. 705/2; 705/3

(58) Field of Classification Search
USPC ....................................... 705/2–3
See application file for complete search history.

(56) References Cited

U.S. PATENT DOCUMENTS

| 2002/0133379 | A1* | 9/2002 | Lewis et al. ........................ 705/4 |
| 2003/0163352 | A1* | 8/2003 | Surpin et al. ...................... 705/2 |
| 2007/0192143 | A1* | 8/2007 | Krishnan et al. .................. 705/3 |
| 2008/0133290 | A1* | 6/2008 | Siegrist et al. .................... 705/7 |
| 2011/0184759 | A1* | 7/2011 | Selker et al. ...................... 705/3 |

OTHER PUBLICATIONS

The Joint Commission, The Specifications Manual for National Hospital Inpatient Quality Measures, Jun. 2011, The Joint Commission, Sections: Introduction (pp. -i- through -ix-), NQF-Endorsed Voluntary Consensus Standards for Hospital Care—Measure Set: Heart Failure (HF) (pp. HF-1-1 through HF-1-10, pp. -x- through -xii-).*

* cited by examiner

Primary Examiner — Joy Chng
(74) Attorney, Agent, or Firm — Richard D. Clarke

(57) ABSTRACT

The present invention incorporates medical knowledge into the processes and algorithms that combine inpatient quality outcomes, ambulatory quality measures and health insurers' financial data into a Medical Value Index (MVI) which forms actionable information that hospitals and physicians can use to improve the efficacies and efficiencies of their care. It then quantifies the financial net savings that predictably accrue as a result of the providers' improved medical outcomes. This MVI information enables a hospital or health insurer to equitably share the net saving with the physicians and hospitals as incentives to continuously improve the quality of their patients' care and control costs.

15 Claims, 61 Drawing Sheets

Figure 1C: Medical Value Index (MVI6)
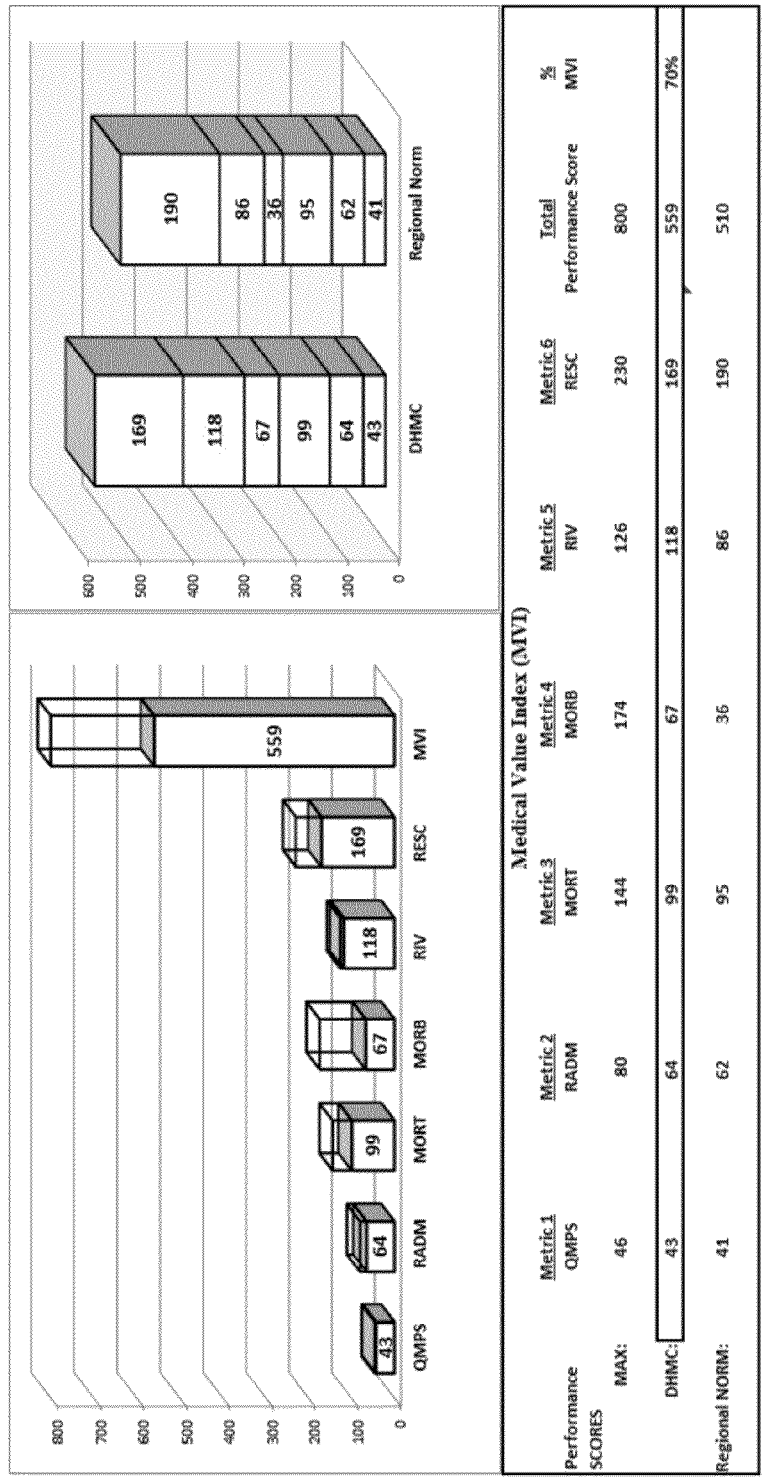

Figure 2: Global Drivers, Case Mix Index Modifier, & Hospital 3 Yr. Average Case Charge

Global Drivers:

| Hospital Case Mix Index Modifier. | | | | CMI Modifier to Apply |
|---|---|---|---|---|
| Average 3Yr CMI | >> | >> | >> | 1.6827 |
| 1.6827 | | | | |

| Inpatient Case Charge (Charge Per Discharge) Modifier. | | | Charge Modifier to Apply |
|---|---|---|---|
| | Greater or Equal 100K | 1 | 0 |
| Average 3Yr Case Charge | $100,000.00 — 99,999.99 | 5 | 0 |
| $37,441.00 | $95,000.00 — 94,999.99 | 10 | 0 |
| | $90,000.00 — 89,999.99 | 15 | 0 |
| | $85,000.00 — 84,999.99 | 20 | 0 |
| | $80,000.00 — 79,999.99 | 25 | 0 |
| | $75,000.00 — 74,999.99 | 30 | 0 |
| | $70,000.00 — 69,999.99 | 35 | 0 |
| | $65,000.00 — 64,999.99 | 40 | 0 |
| | $60,000.00 — 59,999.99 | 45 | 0 |
| | $55,000.00 — 54,999.99 | 50 | 0 |
| | $50,000.00 — 49,999.99 | 55 | 0 |
| | $45,000.00 — 44,999.99 | 60 | 0 |
| | $40,000.00 — 39,999.99 | 65 | 65 |
| | $35,000.00 — 34,999.99 | 70 | 0 |
| | $30,000.00 — 29,999.99 | 75 | 0 |
| | $25,000.00 — 24,999.99 | 80 | 0 |
| | $20,000.00 — 19,999.99 | 85 | 0 |
| | $15,000.00 — 14,999.99 | 90 | 0 |
| | $10,000.00 — 9,999.99 | 95 | 0 |
| | $5,000.00 — 4,999.99 | 100 | 0 |
| | Less Than 5K | | |

Figure 3: QMPS

METRIC 1

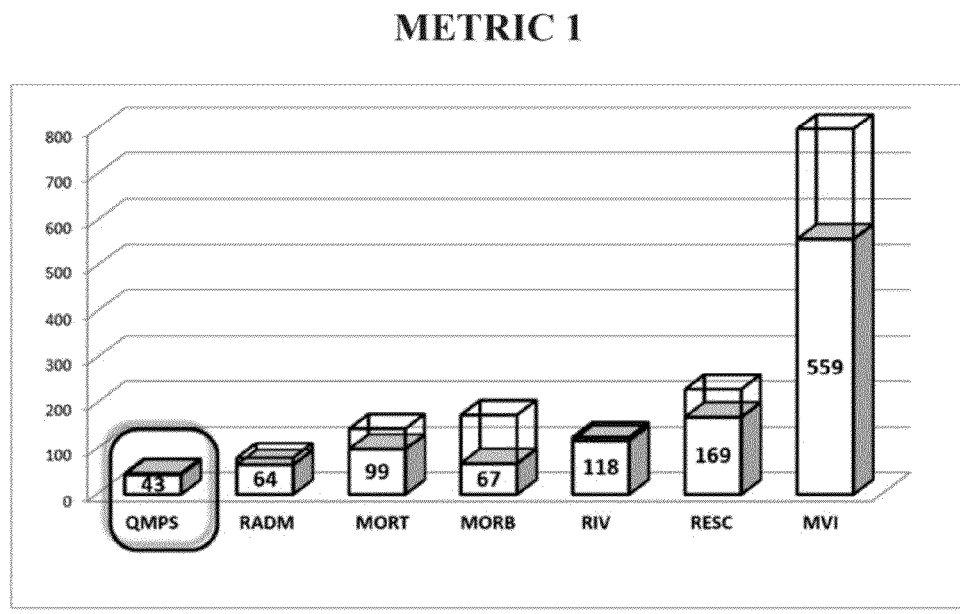

TITLE: Quality Measures & Patient Satisfactions (QMPS)

Score Range: 0 to 46 points (calculated score for this hospital shown as 43 out of 46)

Graphing Color: Medium Blue

Graphing Position: First Position, Left Most of Horizontal Bars and Bottom of Stack Type of Measure: Bundle of Core National Process of Care Measures Score Modified by CMI: No Score Modified by Average Per-Case Charge: No

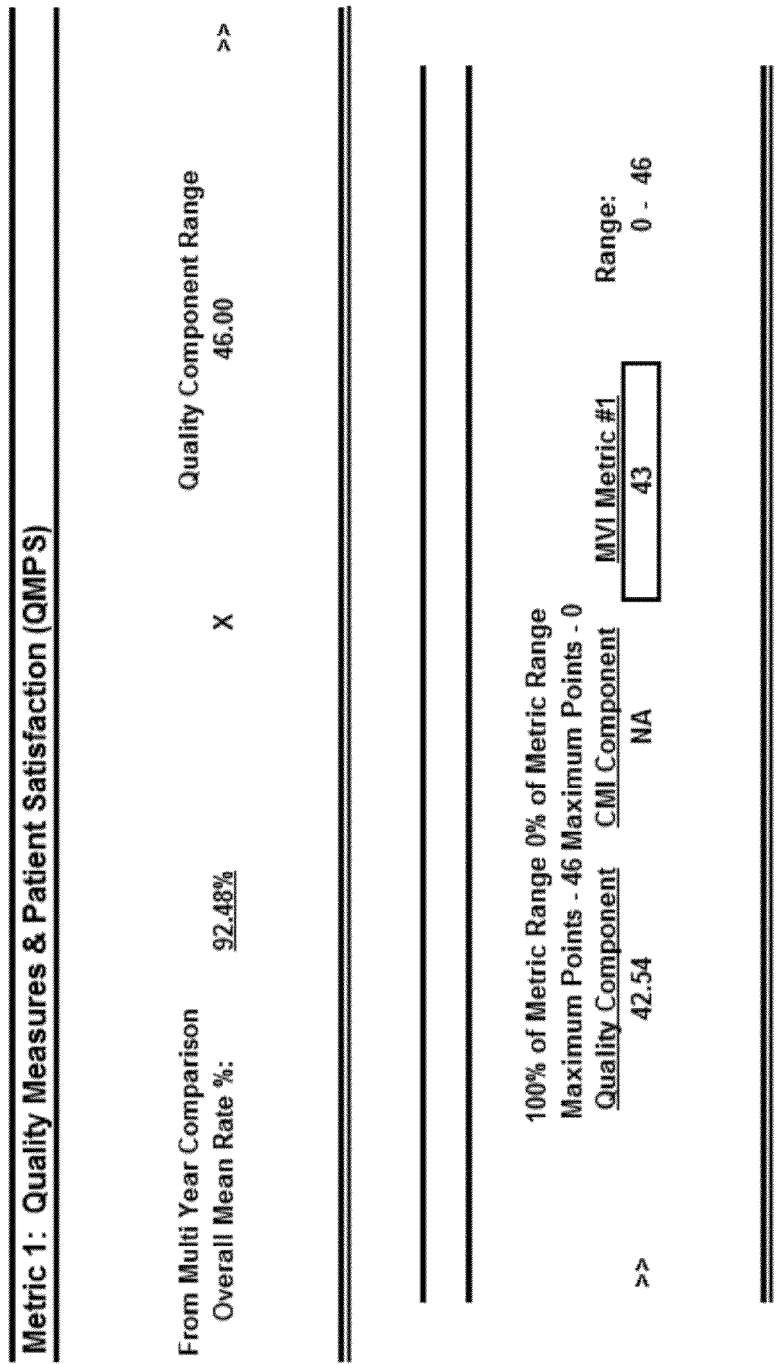
Figure 4: Computation Summary of Quality Measures & Patient Satisfaction (QMPS)

Figure 5: National Hospital Quality Measures (NHQM) – CMS

Metric 1 Select National Quality Measures and Patient Satisfaction (CMS)
[All Business / All MDCs / All Services – DHMC Only, IP Only]

Acute Myocardial Infarction (AMI) – Improvement Is Rate Increase

| KEY | Title | Mean | Delta | ImpUnc | Deg | 2012 Rate | 2012 Num. | 2012 Den. | 2011 & 2010 Rate | 2011 & 2010 Num. | 2011 & 2010 Den. |
|---|---|---|---|---|---|---|---|---|---|---|---|
| AMI-1: | Aspirin at Arrival | 99.2% | -0.4% | 0 | 1 | 99.0% | 199 | 201 | 99.4% | 339 | 341 |
| AMI-2: | Aspirin Prescribed at Discharge | 99.4% | 0.0% | 0 | 1 | 99.4% | 177 | 178 | 99.5% | 367 | 369 |
| AMI-3: | ACEI or ARB for LVSD | 77.9% | -19.9% | 0 | 1 | 68.0% | 17 | 25 | 87.9% | 58 | 66 |
| AMI-4: | Adult Smoking Cessation Advice/Counseling | 100.0% | 0.0% | 1 | 0 | 100.0% | 86 | 86 | 100.0% | 178 | 178 |
| AMI-5: | Beta Blocker Prescribed at Discharge | 99.6% | -0.3% | 0 | 1 | 99.4% | 174 | 175 | 99.7% | 353 | 354 |
| AMI-7a: | Hospital Arrival | NA | NA | NA | NA | NA | NA | NA | NA | NA | NA |
| AMI-8a: | Primary PCI Received within 90 Minutes of Hospital Arrival | 92.3% | -2.2% | 0 | 1 | 91.2% | 31 | 34 | 93.3% | 56 | 60 |
|  | *AMI SubTotal* | *94.7%* | *-0.5%* | *1* | *0* | *97.9%* | *114* | *117* | *98.0%* | *225* | *228* |

Heart Failure (HF) – Improvement Is Rate Increase

| KEY | Title | Mean | Delta | ImpUnc | Deg | Rate | Num. | Den. | Rate | Num. | Den. |
|---|---|---|---|---|---|---|---|---|---|---|---|
| HF-1: | Discharge Instructions | 88.7% | -0.6% | 0 | 1 | 88.4% | 236 | 267 | 89.0% | 453 | 509 |
| HF-2: | Evaluation of LVS Funtion | 99.4% | -0.4% | 0 | 1 | 99.2% | 356 | 359 | 99.5% | 658 | 661 |
| HF-3: | ACEI or ARB for LVSD | 96.4% | 0.7% | 1 | 0 | 96.8% | 91 | 94 | 96.1% | 171 | 178 |
| HF-4: | Adult Smoking Cessation Advice/Counseling | 100.0% | 0.0% | 1 | 0 | 100.0% | 63 | 63 | 100.0% | 110 | 110 |
|  | *HF SubTotal* | *96.1%* | *-0.1%* | *2* | *0* | *95.5%* | *166* | *174* | *95.6%* | *329* | *343* |

Pneumonia (PN) – Improvement Is Rate Increase

| KEY | Title | Mean | Delta | ImpUnc | Deg | Rate | Num. | Den. | Rate | Num. | Den. |
|---|---|---|---|---|---|---|---|---|---|---|---|
| PN-2: | Pneumococcal Vaccination | 94.7% | 3.7% | 1 | 0 | 96.5% | 359 | 372 | 92.8% | 645 | 695 |
| PN-3b: | Blood Cultures Performed in the ER Prior to Initial Antibiotic Received in Hospital | 95.5% | -1.4% | 0 | 1 | 94.8% | 379 | 400 | 96.2% | 700 | 728 |
| PN-4: | Adult Smoking Cessation Advice/Counseling | 98.5% | 0.6% | 1 | 0 | 98.8% | 169 | 171 | 98.3% | 339 | 345 |
| PN-5c: | Initial Antibiotic Received Within 6 Hours of Hospital | 96.0% | -0.6% | 0 | 1 | 95.7% | 334 | 349 | 96.3% | 619 | 643 |
| PN-6: | Initial Antibiotic Selection for CAP in Immunocompetent | 92.4% | 1.4% | 1 | 0 | 93.1% | 216 | 232 | 91.7% | 396 | 432 |
|  | *PN SubTotal* | *95.4%* | *0.6%* | *3* | *0* | *96.1%* | *318* | *323* | *95.2%* | *559* | *587* |

Surgical Care Improvement Project (SCIP) – Improvement Is Rate Increase

| KEY | Title | Mean | Delta | ImpUnc | Deg | Rate | Num. | Den. | Rate | Num. | Den. |
|---|---|---|---|---|---|---|---|---|---|---|---|
| SCIP-Inf-1a: | Prophylactic Antibiotic Received within One Hour to Surgical Incision | 99.0% | 0.1% | 1 | 0 | 99.0% | 713 | 720 | 98.9% | 1463 | 1485 |
| SCIP-Inf-2: | Prophylactic Antibiotic Selection for Surgical Patients | 98.7% | 0.4% | 1 | 0 | 98.9% | 729 | 737 | 98.6% | 1500 | 1522 |
| SCIP-Inf-3a: | Prophylactic Antibiotics Discontinued within 24 Hours After Surgery End Time | 105.7% | -17.6% | 0 | 1 | 96.9% | 685 | 707 | 114.5% | 1433 | 1252 |
| SCIP-Inf-4: | Cardiac Patients with controlled 6am. Postoperative | 91.7% | -1.0% | 0 | 1 | 91.2% | 156 | 171 | 92.3% | 363 | 400 |
| SCIP-Inf-6: | Surgery Patients with Appropriate Hair Removal | 93.4% | 13.2% | 1 | 0 | 100.0% | 1171 | 1171 | 86.8% | 2111 | 2431 |
| SCIP-Card-2: | Surgery Patients on Beta BlockerTherapy Prior Arrival & Periop | 97.2% | 1.6% | 0 | 0 | 98.0% | 391 | 399 | 96.4% | 796 | 826 |
| SCIP-VTE-1: | Surgery Patients with Venous Thromboembolism | 94.9% | 1.8% | 0 | 0 | 95.8% | 676 | 706 | 94.0% | 1030 | 1096 |
| SCIP-VTE-2: | Surgery Patients with Venous Thromboembolism Prophy | 94.4% | 1.9% | 1 | 0 | 95.3% | 672 | 705 | 93.4% | 1021 | 1093 |
|  | *SCIP SubTotal* | *97.2%* | *1.6%* | *1* | *0* | *98.3%* | *709* | *721* | *96.7%* | *1276* | *1320* |

Patient Satisfaction – Improvement Is Rate Increase

| KEY | Title | Mean | Delta | ImpUnc | Deg | Rate | Num. | Den. | Rate | Num. | Den. |
|---|---|---|---|---|---|---|---|---|---|---|---|
| PS-1: | Admission Overall | 87.9% | 0.2% | 0 | 0 | 88.0% | 3470 | 3945 | 87.8% | 7066 | 8052 |
| PS-2: | Room Overall | 82.9% | 1.2% | 0 | 0 | 83.5% | 3295 | 3945 | 82.3% | 6628 | 8052 |
| PS-3: | Meals Overall | 80.2% | -0.9% | 0 | 1 | 79.7% | 3145 | 3945 | 80.6% | 6493 | 8052 |
| PS-4: | Nurses Overall | 79.6% | 0.0% | 1 | 0 | 79.6% | 3139 | 3945 | 79.6% | 6406 | 8052 |
| PS-5: | Test & Treatments | 94.0% | -0.4% | 0 | 1 | 93.8% | 3699 | 3945 | 94.2% | 7583 | 8052 |
| PS-6: | Visitors & Family | 82.9% | 1.1% | 0 | 0 | 83.4% | 3292 | 3945 | 82.4% | 6631 | 8052 |
| PS-7: | Physician | 83.5% | -2.3% | 0 | 1 | 82.4% | 3249 | 3945 | 84.7% | 6818 | 8052 |
| PS-8: | Discharge | 82.7% | -0.7% | 0 | 1 | 82.4% | 3250 | 3945 | 83.1% | 6689 | 8052 |
| PS-9: | Personal Issues | 86.8% | 0.6% | 0 | 0 | 87.1% | 3438 | 3945 | 86.5% | 6965 | 8052 |
| PS-10: | Overall Assessment | 86.6% | 0.4% | 1 | 0 | 86.8% | 3426 | 3945 | 86.4% | 6958 | 8052 |
|  | *PS SubTotal* | *84.7%* | *0.6%* | *1B* | *0* | *87.1%* | *3438* | *3945* | *86.5%* | *6965* | *8052* |
|  | Metric 1 Net: | 92% | -1% | | 15 | | | | | | |

Figure 6A: Nat. Hospital Quality Measures (NHQM) – "Measurement Period" Data

| Metric 1 | Select National Quality Measures and Patient Satisfaction (CMS) [All Business / All MDCs / All Services - OHMC Only, IP Only] Acute Myocardial Infarction (AMI) - Improvement Is Rate Increase | 2012 Aggregated | | |
|---|---|---|---|---|
| KEY | Title | Rate | Num. | Den. |
| AMI-1: | Aspirin at Arrival | 99.0% | 199 | 201 |
| AMI-2: | Aspirin Prescribed at Discharge | 99.4% | 177 | 178 |
| AMI-3: | ACEI or ARB for LVSD | 68.0% | 17 | 25 |
| AMI-4: | Adult Smoking Cessation Advice/Counseling | 100.0% | 86 | 86 |
| AMI-5: | Beta Blocker Prescribed at Discharge | 99.4% | 174 | 175 |
| AMI-7a: | Fibronolytic Therapy Received within 30 Minutes of Hospital Arrival | NA | NA | NA |
| AMI-8a: | Primary PCI Received within 90 Minutes of Hospital | 91.2% | 31 | 34 |
| | *AMI SubTotal* | *97.9%* | *114* | *117* |

Heart Failure (HF) - Improvement Is Rate Increase

| KEY | Title | Rate | Num. | Den. |
|---|---|---|---|---|
| HF-1: | Discharge Instructions | 88.4% | 236 | 267 |
| HF-2: | Evaluation of LVS Funtion | 99.2% | 356 | 359 |
| HF-3: | ACEI or ARB for LVSD | 96.8% | 91 | 94 |
| HF-4: | Adult Smoking Cessation Advice/Counseling | 100.0% | 63 | 63 |
| | *HF SubTotal* | *95.5%* | *166* | *174* |

Pneumonia (PN) - Improvement Is Rate Increase

| KEY | Title | Rate | Num. | Den. |
|---|---|---|---|---|
| PN-2: | Pneumococcal Vaccination | 96.5% | 359 | 372 |
| PN-3b: | Blood Cultures Performed in the ER Prior to Initial Antibiotic Received in Hospital | 94.8% | 379 | 400 |
| PN-4: | Adult Smoking Cessation Advice/Counseling | 98.8% | 169 | 171 |
| PN-5c: | Initial Antibiotic Received Within 6 Hours of Hospital | 95.7% | 334 | 349 |
| PN-6: | Initial Antibiotic Selection for CAP in Immunocompetent Patient | 93.1% | 216 | 232 |
| | *PN SubTotal* | *96.1%* | *310* | *323* |

Surgical Care Improvement Project (SCIP) - Improvement Is Rate Incr

| KEY | Title | Rate | Num. | Den. |
|---|---|---|---|---|
| SCIP-Inf-1a: | Prophylactic Antibiotic Received within One Hour to Surgical Incision | 99.0% | 713 | 720 |
| SCIP-Inf- | Prophylactic Antibiotic Selection for Surgical Patients | 98.9% | 729 | 737 |
| SCIP-Inf-3a: | Prophylactic Antibiotics Discontinued within 24 Hours After Surgery End Time | 96.9% | 685 | 707 |
| SCIP-Inf-4: | Cardiac Patients with controlled 6am, Postoperative Blood Glucose | 91.2% | 156 | 171 |
| SCIP-Inf-6: | Surgery Patients with Appropriate Hair Removal | 100.0% | 1171 | 1171 |
| SCIP-Card- | Surgery Patients on Beta BlockerTherapy Prior Arrival | 98.0% | 391 | 399 |
| SCIP-VTE- | Surgery Patients with Venous Thromboembolism | 95.8% | 676 | 706 |
| SCIP-VTE-2: | Surgery Patients with Venous Thromboembolism Prophy in 24hrs | 95.3% | 672 | 705 |
| | *SCIP SubTotal* | *98.3%* | *709* | *721* |

Patient Satisfaction - Improvement Is Rate Increase

| KEY | Title | Rate | Num. | Den. |
|---|---|---|---|---|
| PS-1: | Admission Overall | 88.0% | 3470 | 3945 |
| PS-2: | Room Overall | 83.5% | 3295 | 3945 |
| PS-3: | Meals Overall | 79.7% | 3145 | 3945 |
| PS-4: | Nurses Overall | 79.6% | 3139 | 3945 |
| PS-5: | Test & Treatments | 93.8% | 3699 | 3945 |
| PS-6: | Visitors & Family | 83.4% | 3292 | 3945 |
| PS-7: | Physician | 82.4% | 3249 | 3945 |
| PS-8: | Discharge | 82.4% | 3250 | 3945 |
| PS-9: | Personal Issues | 87.1% | 3438 | 3945 |
| PS-10: | Overall Assessment | 86.8% | 3426 | 3945 |
| | *PS SubTotal* | *83.7%* | *3303* | *3945* |

Figure 6B: Nat. Hospital Quality Measures (NHQM) – "Measurement Period" Data

| 2012 | | | | | | | | | | | |
|---|---|---|---|---|---|---|---|---|---|---|---|
| 2012Q4 DHMC IP | | | 2012Q3 DHMC IP | | | 2012Q2 DHMC IP | | | 2012Q1 DHMC IP | | |
| Rate | Num. | Den. | Rate | Num. | Den. | Rate | Num. | Den. | Rate | Num. | Den. |
| 100.0% | 63 | 63 | 92.9% | 26 | 28 | 100.0% | 61 | 61 | 100.0% | 49 | 49 |
| 98.0% | 48 | 49 | 100.0% | 27 | 27 | 100.0% | 56 | 56 | 100.0% | 46 | 46 |
| 100.0% | 4 | 4 | 100.0% | 4 | 4 | 11.1% | 1 | 9 | 100.0% | 8 | 8 |
| 100.0% | 21 | 21 | 100.0% | 12 | 12 | 100.0% | 28 | 28 | 100.0% | 25 | 25 |
| 100.0% | 50 | 50 | 100.0% | 26 | 26 | 98.2% | 55 | 56 | 100.0% | 43 | 43 |
| NA | NA | NA | NA | NA | NA | NA | NA | NA | NA | NA | NA |
| 87.5% | 14 | 16 | 100.0% | 7 | 7 | 100.0% | 5 | 5 | 83.3% | 5 | 6 |
| 98.5% | 33 | 34 | 98.1% | 17 | 17 | 95.8% | 34 | 36 | 99.4% | 29 | 30 |
| 88.6% | 62 | 70 | 88.7% | 55 | 62 | 89.2% | 58 | 65 | 87.1% | 61 | 70 |
| 100.0% | 94 | 94 | 100.0% | 85 | 85 | 97.6% | 80 | 82 | 99.0% | 97 | 98 |
| 92.9% | 26 | 28 | 94.1% | 16 | 17 | 100.0% | 22 | 22 | 100.0% | 27 | 27 |
| 100.0% | 16 | 16 | 100.0% | 15 | 15 | 100.0% | 15 | 15 | 100.0% | 17 | 17 |
| 96.7% | 29 | 30 | 95.5% | 43 | 45 | 95.1% | 44 | 46 | 95.3% | 51 | 53 |
| 95.8% | 68 | 71 | 94.4% | 85 | 90 | 96.3% | 105 | 109 | 99.0% | 101 | 102 |
| 97.4% | 74 | 76 | 91.5% | 75 | 82 | 93.3% | 112 | 120 | 96.7% | 118 | 122 |
| 96.8% | 30 | 31 | 96.9% | 31 | 32 | 100.0% | 47 | 47 | 100.0% | 61 | 61 |
| 92.3% | 60 | 65 | 96.0% | 72 | 75 | 97.0% | 96 | 99 | 96.4% | 106 | 110 |
| 89.7% | 35 | 39 | 94.9% | 56 | 59 | 100.0% | 63 | 63 | 87.3% | 62 | 71 |
| 95.5% | 58 | 61 | 94.3% | 66 | 70 | 96.0% | 90 | 94 | 97.7% | 97 | 99 |
| 98.9% | 179 | 181 | 98.7% | 156 | 158 | 98.3% | 178 | 181 | 100.0% | 200 | 200 |
| 98.9% | 184 | 186 | 96.9% | 156 | 161 | 99.5% | 183 | 184 | 100.0% | 206 | 206 |
| 95.0% | 172 | 181 | 98.7% | 152 | 154 | 96.6% | 172 | 178 | 97.4% | 189 | 194 |
| 91.3% | 42 | 46 | 96.8% | 30 | 31 | 83.7% | 36 | 43 | 94.1% | 48 | 51 |
| 100.0% | 288 | 288 | 100.0% | 256 | 256 | 100.0% | 300 | 300 | 100.0% | 327 | 327 |
| 95.7% | 89 | 93 | 98.8% | 84 | 85 | 100.0% | 114 | 114 | 97.2% | 104 | 107 |
| 96.1% | 197 | 205 | 94.5% | 173 | 183 | 96.3% | 206 | 214 | 96.2% | 100 | 104 |
| 95.6% | 196 | 205 | 94.0% | 171 | 182 | 96.3% | 206 | 214 | 95.2% | 99 | 104 |
| 97.6% | 178 | 183 | 98.1% | 155 | 158 | 98.2% | 178 | 181 | 99.2% | 198 | 200 |
| 90.7% | 896 | 988 | 86.5% | 902 | 1043 | 87.7% | 867 | 989 | 87.0% | 805 | 925 |
| 85.9% | 849 | 988 | 79.9% | 833 | 1043 | 85.6% | 847 | 989 | 82.8% | 766 | 925 |
| 82.3% | 813 | 988 | 75.8% | 791 | 1043 | 85.6% | 847 | 989 | 75.0% | 694 | 925 |
| 79.5% | 785 | 988 | 73.3% | 764 | 1043 | 84.2% | 833 | 989 | 81.8% | 757 | 925 |
| 95.6% | 945 | 988 | 91.0% | 949 | 1043 | 95.7% | 946 | 989 | 92.9% | 859 | 925 |
| 85.0% | 840 | 988 | 78.3% | 817 | 1043 | 91.1% | 901 | 989 | 79.4% | 734 | 925 |
| 82.7% | 817 | 988 | 80.6% | 841 | 1043 | 88.7% | 877 | 989 | 77.2% | 714 | 925 |
| 86.9% | 859 | 988 | 74.1% | 773 | 1043 | 88.8% | 878 | 989 | 80.0% | 740 | 925 |
| 91.3% | 902 | 988 | 81.1% | 846 | 1043 | 93.0% | 920 | 989 | 83.2% | 770 | 925 |
| 86.9% | 859 | 988 | 83.6% | 872 | 1043 | 91.1% | 901 | 989 | 85.8% | 794 | 925 |
| 86.3% | 853 | 988 | 80.7% | 842 | 1043 | 86.3% | 854 | 989 | 81.6% | 755 | 925 |

Figure 7A: National Hospital Quality Measures (NHQM) – "Back Period" Data

| Metric 1 | Select National Quality Measures and Patient Satisfaction (CMS) [All Business / All MDCs / All Services – DHMC Only, IP Only] Acute Myocardial Infarction (AMI) – Improvement Is Rate Increase | 2011 & 2010 Aggregated | | |
|---|---|---|---|---|
| KEY | Title | Rate | Num. | Den. |
| AMI-1: | Aspirin at Arrival | 99.4% | 339 | 341 |
| AMI-2: | Aspirin Prescribed at Discharge | 99.5% | 367 | 369 |
| AMI-3: | ACEI or ARB for LVSD | 87.9% | 58 | 66 |
| AMI-4: | Adult Smoking Cessation Advice/Counseling | 100.0% | 178 | 178 |
| AMI-5: | Beta Blocker Prescribed at Discharge | 99.7% | 353 | 354 |
| AMI-7a: | Fibronolytic Therapy Received within 30 Minutes of Hospital Arrival | NA | NA | NA |
| AMI-8a: | Primary PCI Received within 90 Minutes of Hospital | 93.3% | 56 | 60 |
| | AMI SubTotal | 98.8% | 225 | 228 |

Heart Failure (HF) – Improvement Is Rate Increase
| KEY | Title | | | |
|---|---|---|---|---|
| HF-1: | Discharge Instructions | 89.0% | 453 | 509 |
| HF-2: | Evaluation of LVS Funtion | 99.5% | 658 | 661 |
| HF-3: | ACEI or ARB for LVSD | 96.1% | 171 | 178 |
| HF-4: | Adult Smoking Cessation Advice/Counseling | 100.0% | 110 | 110 |
| | HF SubTotal | 95.6% | 328 | 342.5 |

Pneumonia (PN) – Improvement Is Rate Increase
| KEY | Title | | | |
|---|---|---|---|---|
| PN-2: | Pneumococcal Vaccination | 92.8% | 645 | 695 |
| PN-3b: | Blood Cultures Performed in the ER Prior to Initial Antibiotic Received in Hospital | 96.2% | 700 | 728 |
| PN-4: | Adult Smoking Cessation Advice/Counseling | 98.3% | 339 | 345 |
| PN-5c: | Initial Antibiotic Received Within 6 Hours of Hospital | 96.3% | 619 | 643 |
| PN-6: | Initial Antibiotic Selection for CAP in Immunocompetent Patient | 91.7% | 396 | 432 |
| | PN SubTotal | 95.2% | 559 | 586.8 |

Surgical Care Improvement Project (SCIP) – Improvement Is Rate Incre
| KEY | Title | | | |
|---|---|---|---|---|
| SCIP-Inf-1a: | Prophylactic Antibiotic Received within One Hour to Surgical Incision | 98.9% | 1469 | 1485 |
| SCIP-Inf- | Prophylactic Antibiotic Selection for Surgical Patients | 98.6% | 1500 | 1522 |
| SCIP-Inf-3a: | Prophylactic Antibiotics Discontinued within 24 Hours After Surgery End Time | 114.5% | 1433 | 1252 |
| SCIP-Inf-4: | Cardiac Patients with controlled 6am, Postoperative Blood Glucose | 92.3% | 369 | 400 |
| SCIP-Inf-6: | Surgery Patients with Appropriate Hair Removal | 86.8% | 2111 | 2431 |
| SCIP-Card-2: | Surgery Patients on Beta BlockerTherapy Prior Arrival & Periop | 96.4% | 796 | 826 |
| SCIP-VTE- | Surgery Patients with Venous Thromboembolism | 94.0% | 1030 | 1096 |
| SCIP-VTE-2: | Surgery Patients with Venous Thromboembolism Prophy in 24hrs | 93.4% | 1021 | 1093 |
| | SCIP SubTotal | 96.7% | 1276 | 1320 |

Patient Satisfaction – Improvement Is Rate Increase
| KEY | Title | | | |
|---|---|---|---|---|
| PS-1: | Admission Overall | 87.8% | 7066 | 8052 |
| PS-2: | Room Overall | 82.3% | 6628 | 8052 |
| PS-3: | Meals Overall | 80.6% | 6493 | 8052 |
| PS-4: | Nurses Overall | 79.6% | 6406 | 8052 |
| PS-5: | Test & Treatments | 94.2% | 7583 | 8052 |
| PS-6: | Visitors & Family | 82.4% | 6631 | 8052 |
| PS-7: | Physician | 84.7% | 6818 | 8052 |
| PS-8: | Discharge | 83.1% | 6689 | 8052 |
| PS-9: | Personal Issues | 86.5% | 6965 | 8052 |
| PS-10: | Overall Assessment | 86.4% | 6958 | 8052 |
| | PS SubTotal | 84.2% | 6783 | 8052 |

Figure 7B: National Hospital Quality Measures (NHQM) – "Back Period" Data

| 2011 | | | | | | | | | | | |
|---|---|---|---|---|---|---|---|---|---|---|---|
| 2011Q4 DHMC IP | | | 2011Q3 DHMC IP | | | 2011Q2 DHMC IP | | | 2011Q1 DHMC IP | | |
| Rate | Num. | Den. | Rate | Num. | Den. | Rate | Num. | Den. | Rate | Num. | Den. |
| 100.0% | 63 | 63 | 92.9% | 26 | 28 | 100.0% | 61 | 61 | 100.0% | 49 | 49 |
| 98.0% | 48 | 49 | 100.0% | 27 | 27 | 100.0% | 56 | 56 | 100.0% | 46 | 46 |
| 100.0% | 4 | 4 | 100.0% | 4 | 4 | 11.1% | 1 | 9 | 100.0% | 8 | 8 |
| 100.0% | 21 | 21 | 100.0% | 12 | 12 | 100.0% | 28 | 28 | 100.0% | 25 | 25 |
| 100.0% | 50 | 50 | 100.0% | 26 | 26 | 98.2% | 55 | 56 | 100.0% | 43 | 43 |
| | | | | | | | | | | | |
| NA | NA | NA | NA | NA | NA | NA | NA | NA | NA | NA | NA |
| 87.5% | 14 | 16 | 100.0% | 7 | 7 | 100.0% | 5 | 5 | 83.3% | 5 | 6 |
| 98.5% | 33 | 34 | 98.1% | 17 | 17 | 95.8% | 34 | 36 | 99.4% | 29 | 30 |
| | | | | | | | | | | | |
| 88.6% | 62 | 70 | 88.7% | 55 | 62 | 89.2% | 58 | 65 | 87.1% | 61 | 70 |
| 100.0% | 94 | 94 | 100.0% | 85 | 85 | 97.6% | 80 | 82 | 99.0% | 97 | 98 |
| 92.9% | 26 | 28 | 94.1% | 16 | 17 | 100.0% | 22 | 22 | 100.0% | 27 | 27 |
| 100.0% | 16 | 16 | 100.0% | 15 | 15 | 100.0% | 15 | 15 | 100.0% | 17 | 17 |
| 96.7% | 29 | 30 | 95.5% | 43 | 45 | 95.1% | 44 | 46 | 95.3% | 51 | 53 |
| | | | | | | | | | | | |
| 95.8% | 68 | 71 | 94.4% | 85 | 90 | 96.3% | 105 | 109 | 99.0% | 101 | 102 |
| | | | | | | | | | | | |
| 97.4% | 74 | 76 | 91.5% | 75 | 82 | 93.3% | 112 | 120 | 96.7% | 118 | 122 |
| 96.8% | 30 | 31 | 96.9% | 31 | 32 | 100.0% | 47 | 47 | 100.0% | 61 | 61 |
| 92.3% | 60 | 65 | 96.0% | 72 | 75 | 97.0% | 96 | 99 | 96.4% | 106 | 110 |
| | | | | | | | | | | | |
| 89.7% | 35 | 39 | 94.9% | 56 | 59 | 100.0% | 63 | 63 | 87.3% | 62 | 71 |
| 95.5% | 58 | 61 | 94.3% | 66 | 70 | 96.0% | 90 | 94 | 97.7% | 97 | 99 |
| | | | | | | | | | | | |
| 98.9% | 179 | 181 | 98.7% | 156 | 158 | 98.3% | 178 | 181 | 100.0% | 200 | 200 |
| 98.9% | 184 | 186 | 96.9% | 156 | 161 | 99.5% | 183 | 184 | 100.0% | 206 | 206 |
| | | | | | | | | | | | |
| 95.0% | 172 | 181 | 98.7% | 152 | 154 | 96.6% | 172 | 178 | 97.4% | 189 | 194 |
| | | | | | | | | | | | |
| 91.3% | 42 | 46 | 96.8% | 30 | 31 | 83.7% | 36 | 43 | 94.1% | 48 | 51 |
| 100.0% | 288 | 288 | 100.0% | 256 | 256 | 100.0% | 300 | 300 | 100.0% | 327 | 327 |
| | | | | | | | | | | | |
| 95.7% | 89 | 93 | 98.8% | 84 | 85 | 100.0% | 114 | 114 | 97.2% | 104 | 107 |
| 96.1% | 197 | 205 | 94.5% | 173 | 183 | 96.3% | 206 | 214 | 96.2% | 100 | 104 |
| | | | | | | | | | | | |
| 95.6% | 196 | 205 | 94.0% | 171 | 182 | 96.3% | 206 | 214 | 95.2% | 99 | 104 |
| 97.6% | 178 | 183 | 98.1% | 155 | 158 | 98.2% | 178 | 181 | 99.2% | 198 | 200 |
| | | | | | | | | | | | |
| 88.0% | 884 | 1004 | 79.0% | 868 | 1099 | 89.0% | 833 | 936 | 86.0% | 802 | 933 |
| 82.0% | 823 | 1004 | 72.0% | 791 | 1099 | 85.0% | 796 | 936 | 76.0% | 709 | 933 |
| 86.0% | 863 | 1004 | 79.0% | 868 | 1099 | 91.0% | 852 | 936 | 68.0% | 634 | 933 |
| 81.0% | 813 | 1004 | 65.0% | 714 | 1099 | 82.1% | 768 | 936 | 76.0% | 709 | 933 |
| 95.0% | 954 | 1004 | 88.0% | 967 | 1099 | 97.0% | 908 | 936 | 93.0% | 868 | 933 |
| 79.0% | 793 | 1004 | 71.0% | 780 | 1099 | 91.0% | 852 | 936 | 64.0% | 597 | 933 |
| 89.0% | 894 | 1004 | 74.0% | 813 | 1099 | 91.0% | 852 | 936 | 82.0% | 765 | 933 |
| 89.0% | 894 | 1004 | 65.0% | 714 | 1099 | 94.0% | 880 | 936 | 77.0% | 718 | 933 |
| 91.0% | 914 | 1004 | 69.0% | 758 | 1099 | 91.0% | 852 | 936 | 75.0% | 700 | 933 |
| 82.0% | 823 | 1004 | 76.0% | 835 | 1099 | 87.0% | 814 | 936 | 82.0% | 765 | 933 |
| 85.3% | 857 | 1004 | 76.6% | 842 | 1099 | 88.4% | 827 | 936 | 76.6% | 715 | 933 |

Figure 7C: National Hospital Quality Measures (NHQM) – "Back Period" Data

| 2010 | | | | | | | | | | | |
|---|---|---|---|---|---|---|---|---|---|---|---|
| 2010Q4 DHMC IP | | | 2010Q3 DHMC IP | | | 2010Q2 DHMC IP | | | 2010Q1 DHMC IP | | |
| Rate | Num. | Den. | Rate | Num. | Den. | Rate | Num. | Den. | Rate | Num. | Den. |
| 100.0% | 54 | 54 | 100.0% | 25 | 25 | 100.0% | 36 | 36 | 100.0% | 25 | 25 |
| 98.0% | 50 | 51 | 100.0% | 43 | 43 | 100.0% | 51 | 51 | 100.0% | 46 | 46 |
| 100.0% | 14 | 14 | 100.0% | 7 | 7 | 100.0% | 13 | 13 | 100.0% | 7 | 7 |
| 100.0% | 22 | 22 | 100.0% | 23 | 23 | 100.0% | 24 | 24 | 100.0% | 23 | 23 |
| 100.0% | 50 | 50 | 100.0% | 38 | 38 | 100.0% | 50 | 50 | 100.0% | 41 | 41 |
| NA | NA | NA | NA | NA | NA | NA | NA | NA | NA | NA | NA |
| 100.0% | 5 | 5 | 100.0% | 8 | 8 | 85.7% | 6 | 7 | 100.0% | 6 | 6 |
| 99.5% | 33 | 33 | 100.0% | 24 | 24 | 99.4% | 30 | 30 | 100.0% | 25 | 25 |
| 94.4% | 51 | 54 | 91.1% | 51 | 56 | 91.2% | 52 | 57 | 84.0% | 63 | 75 |
| 100.0% | 73 | 73 | 100.0% | 70 | 70 | 100.0% | 70 | 70 | 100.0% | 89 | 89 |
| 90.0% | 18 | 20 | 95.0% | 19 | 20 | 100.0% | 20 | 20 | 95.8% | 23 | 24 |
| 100.0% | 7 | 7 | 100.0% | 11 | 11 | 100.0% | 13 | 13 | 100.0% | 16 | 16 |
| 96.8% | 37 | 39 | 96.2% | 38 | 39 | 96.9% | 39 | 40 | 93.6% | 48 | 51 |
| 93.1% | 67 | 72 | 87.5% | 56 | 64 | 88.5% | 69 | 78 | 86.2% | 94 | 109 |
| 96.1% | 74 | 77 | 100.0% | 64 | 64 | 100.0% | 71 | 71 | 96.6% | 112 | 116 |
| 95.5% | 42 | 44 | 97.7% | 43 | 44 | 97.4% | 38 | 39 | 100.0% | 47 | 47 |
| 98.6% | 69 | 70 | 95.2% | 59 | 62 | 98.4% | 61 | 62 | 96.0% | 96 | 100 |
| 95.5% | 42 | 44 | 85.4% | 35 | 41 | 89.6% | 43 | 48 | 89.6% | 60 | 67 |
| 95.8% | 59 | 61 | 93.5% | 51 | 55 | 94.6% | 56 | 60 | 93.2% | 82 | 88 |
| 98.5% | 199 | 202 | 99.4% | 173 | 174 | 98.9% | 182 | 184 | 99% | 202 | 205 |
| 98.1% | 202 | 206 | 97.2% | 174 | 179 | 98.9% | 187 | 189 | 99% | 208 | 211 |
| 151.1% | 198 | 131 | 125.0% | 170 | 136 | 133.3% | 180 | 135 | 140% | 200 | 143 |
| 87.0% | 47 | 54 | 92.3% | 48 | 52 | 94.5% | 52 | 55 | 97% | 66 | 68 |
| 0.3% | 1 | 320 | 100.0% | 296 | 296 | 100.0% | 304 | 304 | 100% | 339 | 340 |
| 99.1% | 108 | 109 | 97.1% | 100 | 103 | 95.5% | 105 | 110 | 88% | 92 | 105 |
| 87.0% | 87 | 100 | 88.9% | 80 | 90 | 96.0% | 96 | 100 | 91% | 91 | 100 |
| 87.9% | 87 | 99 | 85.6% | 77 | 90 | 95.0% | 95 | 100 | 91% | 90 | 99 |
| 76.1% | 116 | 153 | 99.8% | 140 | 140 | 102.0% | 150 | 147 | 1 | 161 | 159 |
| 92.0% | 945 | 1027 | 90.0% | 959 | 1065 | 95.0% | 908 | 956 | 84% | 867 | 1032 |
| 86.0% | 883 | 1027 | 87.0% | 927 | 1065 | 87.0% | 832 | 956 | 84% | 867 | 1032 |
| 76.0% | 781 | 1027 | 77.0% | 820 | 1065 | 90.0% | 860 | 956 | 79% | 815 | 1032 |
| 71.0% | 729 | 1027 | 83.0% | 884 | 1065 | 90.0% | 860 | 956 | 90% | 929 | 1032 |
| 95.0% | 976 | 1027 | 95.0% | 1012 | 1065 | 96.0% | 918 | 956 | 95% | 980 | 1032 |
| 88.0% | 904 | 1027 | 88.0% | 937 | 1065 | 90.0% | 860 | 956 | 88% | 908 | 1032 |
| 77.0% | 791 | 1027 | 90.0% | 959 | 1065 | 96.0% | 918 | 956 | 80% | 826 | 1032 |
| 82.0% | 842 | 1027 | 81.0% | 863 | 1065 | 90.0% | 860 | 956 | 89% | 918 | 1032 |
| 89.0% | 914 | 1027 | 92.0% | 980 | 1065 | 96.0% | 918 | 956 | 90% | 929 | 1032 |
| 87.0% | 893 | 1027 | 91.0% | 969 | 1065 | 93.0% | 889 | 956 | 94% | 970 | 1032 |
| 83.4% | 856 | 1027 | 86.4% | 920 | 1065 | 91.7% | 877 | 956 | 1 | 889 | 1032 |

Figure 8: RADM
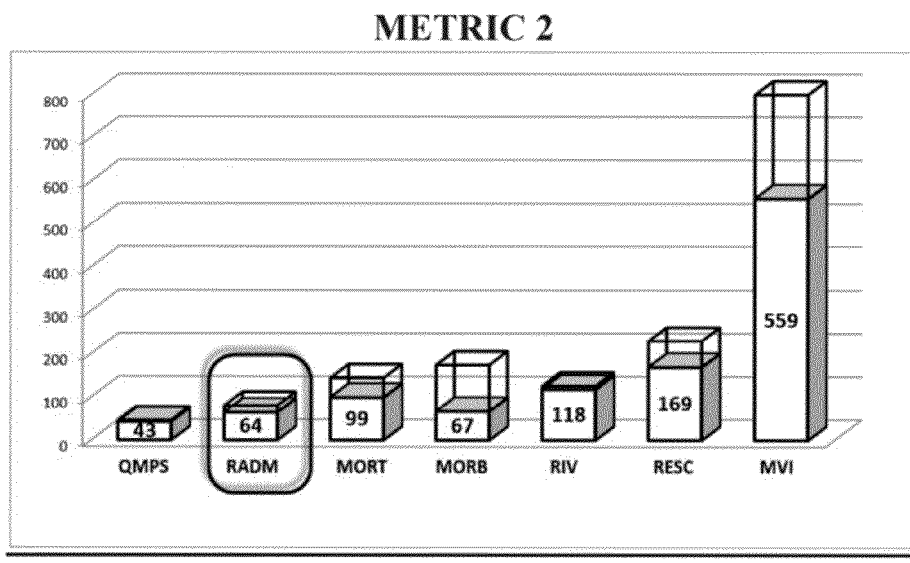
TITLE: Composite Re-Admission Rate (RADM)
Score Range: 0 to 80 points (calculated score for this hospital shown as 64 out of 80)
Graphing Color: Orange
Graphing Position: Second Position, 2nd From Left of Horizontal, 2nd From Bottom of Stack
Type of Measure: Bundle of Re-Admission Rate measures
Score Modified by CMI: No
Score Modified by Average Per-Case Charge: No

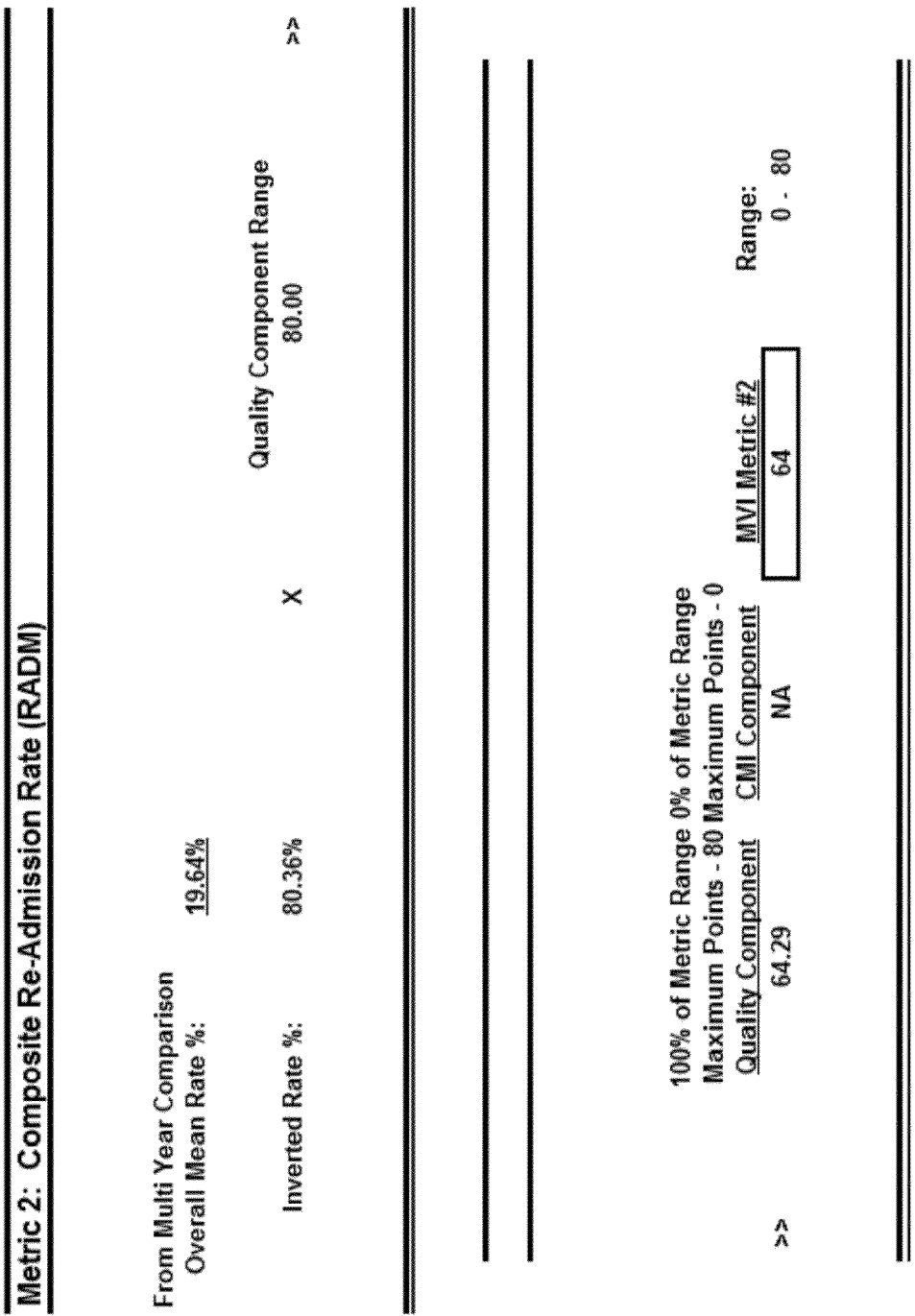
Figure 9: Composite Re-Admit Rate (RADM) - Computation Summary

Figure 10: Composite Re-Admit Rate (RADM) – Computation Detail

Metric 2 Composite Re-Admit Rate Rate
[All Business / All MDCs / All Services - DHMC Only, IP Only]
Inpatient Re-Admission Indicators - Improvement Is Rate Decrease

| KEY | Title | 2012 Measurement Period | | | 2011 & 2010 Back Period | | | 2012 vs 2011 & 2010 Comparison | | | |
|---|---|---|---|---|---|---|---|---|---|---|---|
| | | Rate | Num. | Den. | Rate | Num. | Den. | Mean | Delta | Imp/Unc | Deg |
| RADM-30-AM | Acute Myocardial Infarction (AMI) Re-Admission Rate | 18.9% | 38 | 201 | 19.1% | 65 | 341 | 19.0% | -0.2% | 1 | 0 |
| RADM-30-HF | Heart Failure (HF) Re-Admission Rate | 22.5% | 60 | 267 | 23.2% | 118 | 509 | 22.8% | -0.7% | 1 | 0 |
| RADM-30-PN | Pneumonia (PN) Re-Admission Rate | 16.7% ↑ | 62 | 372 | 17.6% ↑ | 122 | 695 | 17.1% ↑ | -0.9% | 1 | 0 |
| | Metric 2 Net: | | | | | | | 20% | | 3 | 0 |

Figure 11: Composite Re-Admit Rate (RADM) – "Measurement Period" Data

| Metric 2 | Composite Re-Admit Rate Rate |
|---|---|
| [All Business / All MDCs / All Services - DHMC, IP Only] | |

Inpatient Re-Admission Indicators - Improvement Is Rate Decrease

| KEY | Title | | | 2012 Aggregated | | |
|---|---|---|---|---|---|---|
| | | | Rate | Num. | Den. | |
| RADM-30-AMI | Acute Myocardial Infarction (AMI) Re-Admission Rate | | 18.9% | 38 | 201 | |
| RADM-30-HF | Heart Failure (HF) Re-Admission Rate | | 22.5% | 60 | 267 | |
| RADM-30-PN | Pneumonia (PN) Re-Admission Rate | | ↗ 16.7% | 62 | 372 | |

2012

| 2012Q4 DHMC IP | | | 2012Q3 DHMC IP | | | 2012Q2 DHMC IP | | | 2012Q1 DHMC IP | | |
|---|---|---|---|---|---|---|---|---|---|---|---|
| Rate | Num. | Den. | Rate | Num. | Den. | Rate | Num. | Den. | Rate | Num. | Den. |
| 20.6% | 13 | 63 | 21.4% | 6 | 28 | 18.0% | 11 | 61 | 16.3% | 8 | 49 |
| 24.3% | 17 | 70 | 24.2% | 15 | 62 | 18.5% | 12 | 65 | 22.9% | 16 | 70 |
| 15.5% | 11 | 71 | 18.9% | 17 | 90 | 14.7% | 16 | 109 | 17.6% | 18 | 102 |

Figure 12: Composite Re-Admit Rate (RADM) – "Back Period" Data

| Metric 2 | Composite Re-Admit Rate Rate |
|---|---|
| | [All Business / All MDCs / All Services - DHMC, IP Only] |
| | Inpatient Re-Admission Indicators - Improvement Is Rate Decrease |

| KEY | Title | 2011 & 2010 Aggregated | | |
|---|---|---|---|---|
| | | Rate | Num. | Den. |
| RADM-30-AMI | Acute Myocardial Infarction (AMI) Re-Admission Rate | 19.1% | 65 | 341 |
| RADM-30-HF | Heart Failure (HF) Re-Admission Rate | 23.2% | 118 | 509 |
| ↗ RADM-30-PN | Pneumonia (PN) Re-Admission Rate | ↗ 17.6% | 122 | 695 |

2011

| 2011Q4 DHMC IP | | | 2011Q3 DHMC IP | | | 2011Q2 DHMC IP | | | 2011Q1 DHMC IP | | |
|---|---|---|---|---|---|---|---|---|---|---|---|
| Rate | Num. | Den. | Rate | Num. | Den. | Rate | Num. | Den. | Rate | Num. | Den. |
| 19.0% | 12 | 63 | 21.4% | 6 | 28 | 21.3% | 13 | 61 | 18.4% | 9 | 49 |
| 25.7% | 18 | 70 | 19.4% | 12 | 62 | 24.6% | 16 | 65 | 25.7% | 18 | 70 |
| 16.9% | 12 | 71 | 20.0% | 18 | 90 | 17.4% | 19 | 109 | 18.6% | 19 | 102 |

2010

| 2010Q4 DHMC IP | | | 2010Q3 DHMC IP | | | 2010Q2 DHMC IP | | | 2010Q1 DHMC IP | | |
|---|---|---|---|---|---|---|---|---|---|---|---|
| Rate | Num. | Den. | Rate | Num. | Den. | Rate | Num. | Den. | Rate | Num. | Den. |
| 18.5% | 10 | 54 | 16.0% | 4 | 25 | 16.7% | 6 | 36 | 20.0% | 5 | 25 |
| 22.2% | 12 | 54 | 21.4% | 12 | 56 | 24.6% | 14 | 57 | 21.3% | 16 | 75 |
| 15.3% | 11 | 72 | 15.6% | 10 | 64 | 16.7% | 13 | 78 | 18.3% | 20 | 109 |

Figure 13: MORT

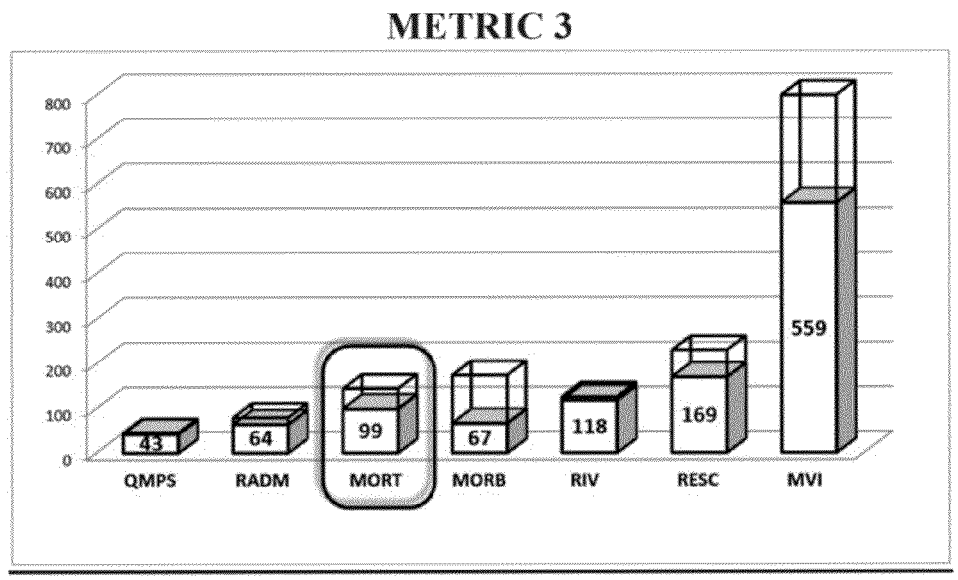

TITLE: Risk Adjusted Mortality Rate (MORT)

Score Range: 0 to 144 points (calculated score for this hospital shown as 99 out of 144)

Graphing Color: Yellow

Graphing Position: Third Position, 3rd From Left of Horizontal, 3rd From Bottom of Stack Type of Measure: Outcome Aggregation; Collection of Mortality Rates Score Modified by CMI: Yes Score Modified by Average Per-Case Charge: No Figure 14: Risk Adjusted Mortality (MORT) – Computation Summary

Metric 3: Risk Adjusted Mortality Rate Analysis (MORT)

| | |
|---|---|
| Correct For Missing Sub Measures | |
| Number of Sub Measures: | 9 |
| Degraded: | 2 |
| Improved/Unchanged: | 7 |
| NotMeasurable: | 0 |
| Set NotMeasured to C: | x12.4 |
| + | 0.00 >> |

From Multi Year Comparison
Overall Trend Grade Score: 93.80

90% of Metric Range 10% of Metric Range
Maximum Points - 129.Maximum Points -14.4

| Quality Component | CMI Component | MVI Metric #3 | Range: |
|---|---|---|---|
| 93.80 | 5.05 | 99 | 0 - 144 |

>>

Figure 15: Risk Adjusted Mortality Rate (MORT) – Computation Detail Data

Metric 3 Risk Adjusted Mortality Rate
[All Payors / All MDCs / All Services - DHMC Only, IP Only]
Inpatient Mortality - Improvement Is Rate Decrease

| KEY | Title | 2012 vs 2011 & 2010 Comparison | | | | | |
|---|---|---|---|---|---|---|---|
| | | TrendGradeScore | TrendGrade | Imp/Unc | Deg | MeanDeltaFlag | |
| ALL MDC | Hospital Mortality Rate Comparison | 12.4 | C | 1 | 0 | 1 | |
| 8 | Ortho Mortality Rate Comparison | 14.4 | A | 1 | 0 | 2 | |
| 5 | Circ Mortality Rate Comparison | 14.4 | A | 1 | 0 | 2 | |
| 6 | Dgst Mortality Rate Comparison | 0.0 | F | 0 | 1 | 0 | |
| 4 | Pulm Mortality Rate Comparison | 14.4 | A | 1 | 0 | 2 | |
| 1 | Nerv Mortality Rate Comparison | 0.0 | F | 0 | 1 | 0 | |
| MORT-30-AMI | Acute Myocardial Infarction (AMI) 30-Day Mortality | 12.4 | C | 1 | 0 | 1 | |
| MORT-30-HF | Heart Failure (HF) 30-Day Mortality Rate | 12.4 | C | 1 | 0 | 1 | |
| MORT-30-PN | Pneumonia (PN) 30-Day Mortality Rate | 13.4 | B | 1 | 0 | 1.5 | |
| 9 | | | | | | 1.2 | |
| | Metric 3 Net: | 94 | | 7 | 2 | | |

| | 2012 Measurement Period | | | | |
|---|---|---|---|---|---|
| DeltaFlag | Delta | Obs | Exp | ExpUL | ExpLL |
| 1 | -0.1% | 3.7% | 3.8% | 3.9% | 3.7% |
| 2 | -0.9% | 0.6% | 1.4% | 1.5% | 1.3% |
| 2 | -0.6% | 3.9% | 4.5% | 4.6% | 4.4% |
| 0 | 0.7% | 3.1% | 2.5% | 2.6% | 2.4% |
| 2 | -0.6% | 4.9% | 5.5% | 5.6% | 5.4% |
| 0 | 3.0% | 8.0% | 5.0% | 5.1% | 4.9% |
| 1 | -0.3% | 17.2% | 17.5% | 21.0% | 14.0% |
| 1 | -0.4% | 13.1% | 13.5% | 16.2% | 10.7% |
| 1 | -0.1% | 16.9% | 17.0% | 19.5% | 14.5% |

| | 2011 & 2010 Back Period | | | | | |
|---|---|---|---|---|---|---|
| DeltaFlag | Delta | Obs | Exp | ExpUL | ExpLL | |
| 1 | -0.1% | 3.7% | 3.8% | 3.9% | 3.7% | |
| 2 | -0.9% | 0.6% | 1.4% | 1.5% | 1.3% | |
| 2 | -0.6% | 3.9% | 4.5% | 4.6% | 4.4% | |
| 0 | 0.7% | 3.1% | 2.5% | 2.6% | 2.4% | |
| 2 | -0.6% | 4.9% | 5.5% | 5.6% | 5.4% | |
| 0 | 3.0% | 8.0% | 5.0% | 5.1% | 4.9% | |
| 1 | -0.3% | 17.2% | 17.5% | 21.0% | 14.0% | |
| 1 | -0.4% | 13.1% | 13.5% | 16.2% | 10.7% | |
| 2 | 1.2% | 16.9% | 15.8% | 19.0% | 17.0% | |

DeltaFlag Legend
GRN  2 = Significantly Improved
YLW  1 = Unchanged or Insignificant Change
RED  0 = Significant Degradation Figure 16: Risk Adjusted Mortality Rate (MORT) – "Measurement Period" Data

| Metric 3 | Risk Adjusted Mortality Rate | | | | | | | |
|---|---|---|---|---|---|---|---|---|
| | [All Payors / All MDCs / All Services - DHMC, IP Only] | | | | | | | |
| | Inpatient Mortality - Improvement Is Rate Decrease | | | | 2012 Aggregated | | | |
| KEY | Title | DeltaFlag | Delta | Obs | Exp | ExpUL | ExpLL | |
| ALL MDC | Hospital Mortality Rate Comparison | 1 | -0.1% | 3.7% | 3.8% | 3.9% | 3.7% | |
| 8 | Ortho Mortality Rate Comparison | 2 | -0.9% | 0.6% | 1.4% | 1.5% | 1.3% | |
| 5 | Circ Mortality Rate Comparison | 2 | -0.6% | 3.9% | 4.5% | 4.6% | 4.4% | |
| 6 | Dgst Mortality Rate Comparison | 0 | 0.7% | 3.1% | 2.5% | 2.6% | 2.4% | |
| 4 | Pulm Mortality Rate Comparison | 2 | -0.6% | 4.9% | 5.5% | 5.6% | 5.4% | |
| 1 | Nerv Mortality Rate Comparison | 0 | 3.0% | 8.0% | 5.0% | 5.1% | 4.9% | |
| MORT-30-AMI | Acute Myocardial Infarction (AMI) 30-Day Mortality | 1 | -0.3% | 17.2% | 17.5% | 21.0% | 14.0% | |
| MORT-30-HF | Heart Failure (HF) 30-Day Mortality Rate | 1 | -0.4% | 13.1% | 13.5% | 16.2% | 10.7% | |
| MORT-30-PN | Pneumonia (PN) 30-Day Mortality Rate | 1 | -0.1% | 16.9% | 17.0% | 19.5% | 14.5% | |

| | 2012 2012Q4-2012Q1 DHMC IP | | | | | |
|---|---|---|---|---|---|---|
| DeltaFlag | Delta | Obs | Exp | ExpUL | ExpLL | |
| 2 | -0.1% | 3.7% | 3.8% | 3.9% | 3.7% | |
| 2 | -0.9% | 0.6% | 1.4% | 1.5% | 1.3% | |
| 2 | -0.6% | 3.9% | 4.5% | 4.6% | 4.4% | |
| 0 | 0.7% | 3.1% | 2.5% | 2.6% | 2.4% | |
| 2 | -0.6% | 4.9% | 5.5% | 5.6% | 5.4% | |
| 0 | 3.0% | 8.0% | 5.0% | 5.1% | 4.9% | |
| 2 | -0.3% | 17.2% | 17.5% | 21.0% | 14.0% | |
| 2 | -0.4% | 13.1% | 13.5% | 16.2% | 10.7% | |
| 2 | -0.1% | 16.9% | 17.0% | 19.5% | 14.5% | |

DeltaFlag Legend
GRN   2 = Significantly Improved
YLW   1 = Unchanged or Insignificant Change
RED   0 = Significant Degredation Figure 17: Risk Adjusted Mortality Rate (MORT) — "Back Period" Data

| Metric 3 | Risk Adjusted Mortality Rate | | | | | | | | | | |
|---|---|---|---|---|---|---|---|---|---|---|---|
| | [All Payors / All MDCs / All Services - DHMC, IP Only] | | | | | | | | | | |
| | Inpatient Mortality - Improvement Is Rate Decrease | | | | | | | | | | |

|  |  | 2011 & 2010 Aggregated | | | | | |
|---|---|---|---|---|---|---|---|
| KEY | Title | DeltaFlag | Delta | Obs | Exp | ExpUL | ExpLL |
| ALL MDC | Hospital Mortality Rate Comparison | 1 | -0.1% | 3.7% | 3.8% | 3.9% | 3.7% |
| 8 | Ortho Mortality Rate Comparison | 2 | -0.9% | 0.6% | 1.4% | 1.5% | 1.3% |
| 5 | Circ Mortality Rate Comparison | 2 | -0.6% | 3.9% | 4.5% | 4.6% | 4.4% |
| 6 | Dgst Mortality Rate Comparison | 0 | 0.7% | 3.1% | 2.5% | 2.6% | 2.4% |
| 4 | Pulm Mortality Rate Comparison | 2 | -0.6% | 4.9% | 5.5% | 5.6% | 5.4% |
| 1 | Nerv Mortality Rate Comparison | 0 | 3.0% | 8.0% | 5.0% | 5.1% | 4.9% |
| MORT-30-AMI | Acute Myocardial Infarction (AMI) 30-Day Mortality | 1 | -0.3% | 17.2% | 17.5% | 21.0% | 14.0% |
| MORT-30-HF | Heart Failure (HF) 30-Day Mortality Rate | 1 | -0.4% | 13.1% | 13.5% | 16.2% | 10.7% |
| MORT-30-PN | Pneumonia (PN) 30-Day Mortality Rate | 2 | 1.2% | 16.9% | 15.8% | 19.0% | 17.0% |

| 2011 2011Q4-2011Q1 DHMC IP | | | | | | | 2010 2010Q4-2010Q1 DHMC IP | | | | | | |
|---|---|---|---|---|---|---|---|---|---|---|---|---|---|
| DeltaFlag | Delta | Obs | Exp | ExpUL | ExpLL | | DeltaFlag | Delta | Obs | Exp | ExpUL | ExpLL | |
| 2 | -0.2% | 3.7% | 3.9% | 4.0% | 3.8% | | 0 | 0.0% | 3.6% | 3.6% | 3.7% | 3.5% | |
| 2 | -2.1% | 0.0% | 2.1% | 2.2% | 2.0% | | 0 | 0.4% | 1.1% | 0.7% | 0.8% | 0.6% | |
| 2 | -0.7% | 4.6% | 5.3% | 5.4% | 5.2% | | 2 | -0.6% | 3.2% | 3.8% | 3.9% | 3.7% | |
| 0 | 0.5% | 3.4% | 2.9% | 3.0% | 2.8% | | 0 | 0.8% | 2.9% | 2.0% | 2.1% | 1.9% | |
| 2 | -0.9% | 5.0% | 5.9% | 6.0% | 5.8% | | 2 | -0.3% | 4.8% | 5.2% | 5.3% | 5.1% | |
| 0 | 4.6% | 10.2% | 5.6% | 5.7% | 5.5% | | 0 | 1.5% | 5.8% | 4.4% | 4.5% | 4.3% | |
| 2 | -0.3% | 17.2% | 17.5% | 21.0% | 14.0% | | 2 | -0.3% | 17.2% | 17.5% | 21.0% | 14.0% | |
| 2 | -0.4% | 13.1% | 13.5% | 16.2% | 10.7% | | 2 | -0.4% | 13.1% | 13.5% | 16.2% | 10.7% | |
| 2 | -0.1% | 16.9% | 17.0% | 19.5% | 14.5% | | 0 | 2.4% | 16.9% | 14.5% | 18.4% | 19.5% | |

DeltaFlag Legend
GRN  2 = Significantly Improved
YLW  1 = Unchanged or Insignificant Change
RED  0 = Significant Degredation Figure 18: MORB
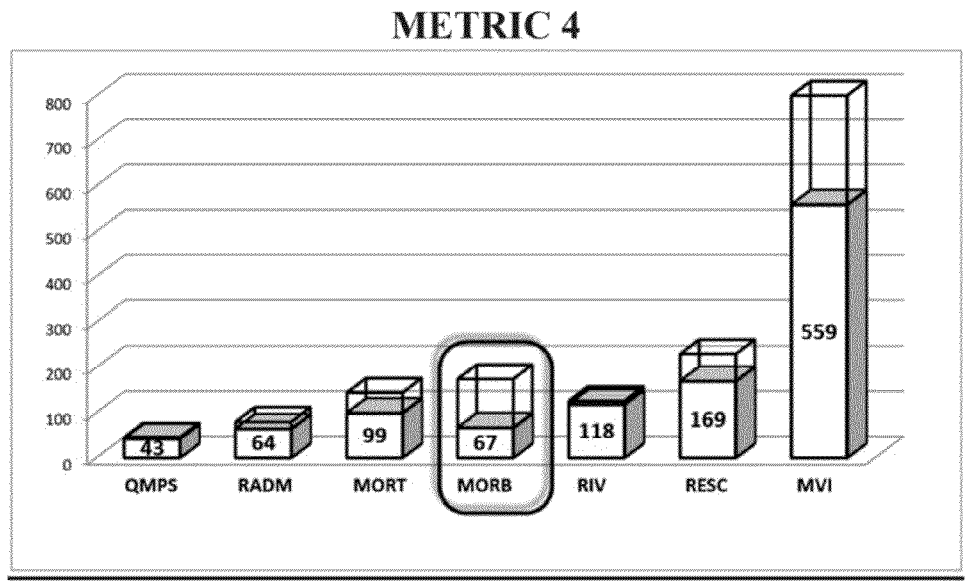
TITLE: Risk Adjusted Morbidity Rate (MORB)
Score Range: 0 to 174 points (calculated score for this hospital shown as 67 out of 174)
Graphing Color: Red
Graphing Position: Fourth Position, 4th From Left of Horizontal, 4th From Bottom of Stack
Type of Measure: Outcome Aggregation; Excessive LOS
Score Modified by CMI: Yes
Score Modified by Average Per-Case Charge: No Figure 19: Risk Adjusted Morbidity Rate (MORB) – Computation Summary
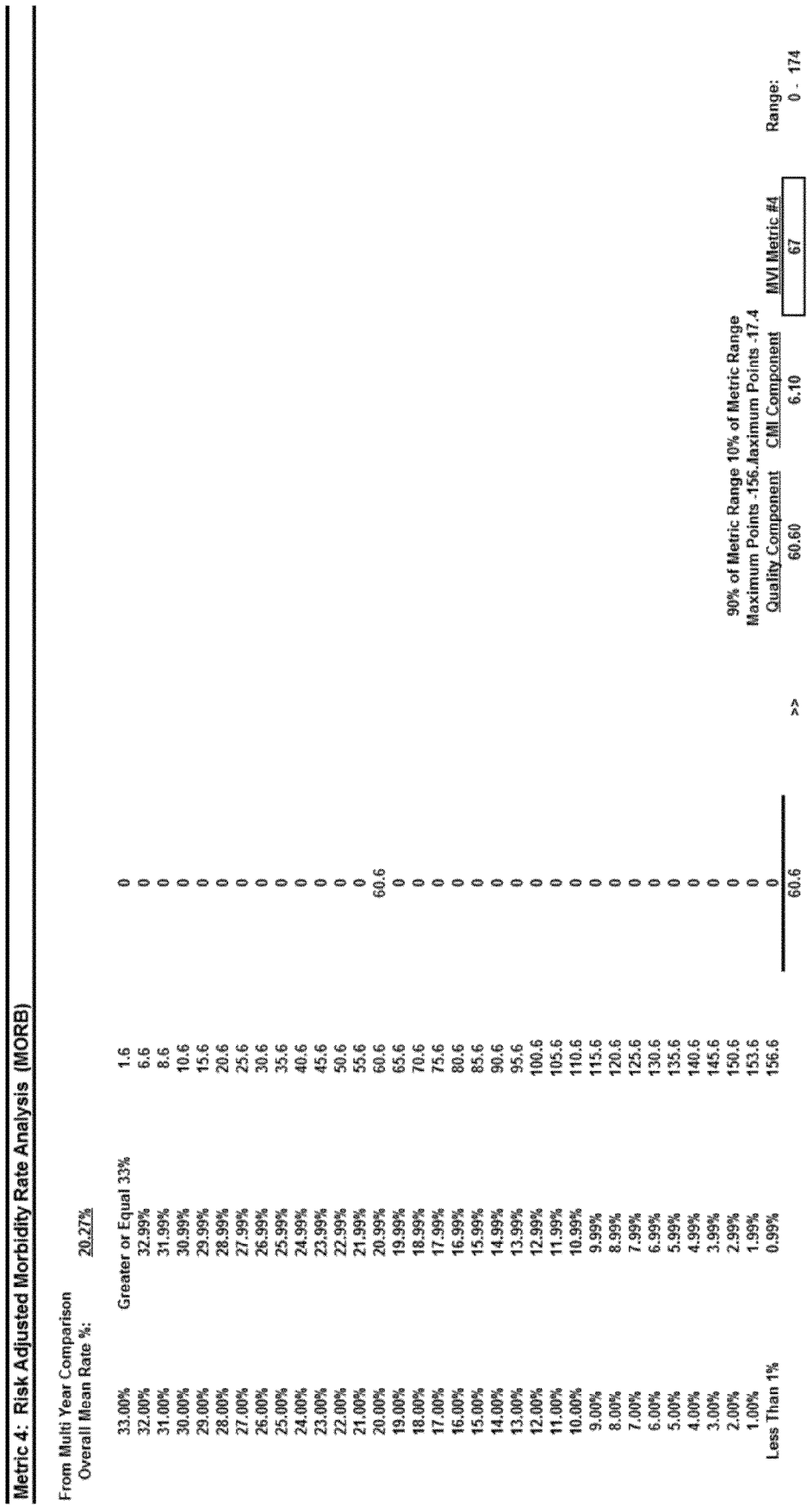

Figure 20: Risk Adjusted Morbidity Rate (MORB) – Computation Detail

Metric 4 Risk Adjusted Morbidity Rate
[All Payors / All MDCs / All Services - DHMC Only, IP Only]

Inpatient Morbidity - Improvement Is Rate Decrease

| KEY | Title | 2012 Measurement Period | | | 2011 & 2010 Back Period | | | 2012 vs 2011 & 2010 Comparison | | |
|-----|-------|------|------|------|------|------|------|------|------|------|
| | | Rate | Num. | Den. | Rate | Num. | Den. | Mean | Delta | Imp/Unc | Deg |
| 853 | Infectios & Parasitic Diseases w/ OR Procedure w/MCC | 31.0% | 9 | 29 | 32.8% | 21 | 64 | 31.92% | -1.8% | 1 | 0 |
| 207 | Respiratory System Diagnosis w/ Ventilator Support 96+ Hour | 18.9% | 9 | 29 | 21.1% | 21 | 64 | 20.02% | -2.2% | 1 | 0 |
| 194 | Simple Pneumonia & Pleurisy w/cc | 16.0% | 41 | 256 | 16.5% | 85 | 515 | 16.26% | -0.5% | 1 | 0 |
| 208 | Respiratory System Diagnosis w/ Ventilator Support <96 Hour | 15.6% | 41 | 256 | 17.9% | 85 | 515 | 16.77% | -2.3% | 1 | 0 |
| 871 | Septicemia or Severe Sepsis w/o MV 96+ Hrs | 22.9% | 16 | 70 | 24.2% | 38 | 157 | 23.53% | -1.3% | 1 | 0 |
| 870 | Septicemia or Severe Sepsis w/ MV 96+ Hrs | 27.3% | 16 | 70 | 28.6% | 38 | 157 | 27.92% | -1.3% | 1 | 0 |
| 193 | Simple Pneumonia & Pleurisy w/mcc | 22.5% | 20 | 89 | 20.8% | 36 | 173 | 21.64% | 1.7% | 0 | 1 |
| 189 | Pulmonary Edema & Respiratory Failure | 11.2% | 20 | 89 | 11.0% | 36 | 173 | 11.11% | 0.2% | 0 | 1 |
| 981 | Extensive OR Procedure Unrelated to Principle Dx | 22.7% | 5 | 22 | 25.5% | 12 | 47 | 24.13% | -2.8% | 1 | 0 |
| 392 | Esophagitis, Gastroent & Misc Digest Disorders w/o MCC | 9.8% | 5 | 22 | 9.0% | 12 | 47 | 9.36% | 0.8% | 0 | 1 |
| 10 | | 19.8% | | | 20.7% | | | 20.27% | -1.0% | 7 | 3 |

Metric 4 Net:

Figure 21: Risk Adjusted Morbidity Rate (MORB) – "Measurement Period" Data

| Metric 4 | Risk Adjusted Morbidity Rate |
|---|---|
| | [All Payors / All MDCs / All Services - DHMC, IP Only] |

Inpatient Morbidity - Improvement Is Rate Decrease

| | | 2012 Aggregated | | |
|---|---|---|---|---|
| KEY | Title | Rate | Num. | Den. |
| 853 | Infectios & Parasitic Diseases w/ OR Procedure w/MCC | 31.0% | 9 | 29 |
| 207 | Respiratory System Diagnosis w/ Ventilator Support 96+ Hour | 18.9% | 7 | 37 |
| 194 | Simple Pneumonia & Pleurisy w/cc | 16.0% | 41 | 256 |
| 208 | Respiratory System Diagnosis w/ Ventilator Support <96 Hour | 15.6% | 10 | 64 |
| 871 | Septicemia or Severe Sepsis w/o MV 96+ Hrs | 22.9% | 16 | 70 |
| 870 | Septicemia or Severe Sepsis w/ MV 96+ Hrs | 27.3% | 3 | 11 |
| 193 | Simple Pneumonia & Pleurisy w/mcc | 22.5% | 20 | 89 |
| 189 | Pulmonary Edema & Respiratory Failure | 11.2% | 11 | 98 |
| 981 | Extensive OR Procedure Unrelated to Principle Dx | 22.7% | 5 | 22 |
| 392 | Esophagitis, Gastroent & Misc Digest Disorders w/o MCC | 9.8% | 24 | 246 |

| 2012 2012Q4-2012Q1 DHMC IP | | |
|---|---|---|
| Rate | Num. | Den. |
| 31.0% | 9 | 29 |
| 18.9% | 7 | 37 |
| 16.0% | 41 | 256 |
| 15.6% | 10 | 64 |
| 22.9% | 16 | 70 |
| 27.3% | 3 | 11 |
| 22.5% | 20 | 89 |
| 11.2% | 11 | 98 |
| 22.7% | 5 | 22 |
| 9.8% | 24 | 246 |

Figure 22: Risk Adjusted Morbidity Rate – "Back Period" Data

| Metric 4 | Risk Adjusted Morbidity Rate | | | | |
|---|---|---|---|---|---|
| [All Payors / All MDCs / All Services - DHMC, IP Only] | | | | | |
| Inpatient Morbidity - Improvement Is Rate Decrease | | | | 2011 & 2010 Aggregated | |
| KEY | Title | | Rate | Num. | Den. |
| 853 | Infections & Parasitic Diseases w/ OR Procedure w/MCC | | 32.8% | 21 | 64 |
| 207 | Respiratory System Diagnosis w/ Ventilator Support 96+ Hour | | 21.1% | 15 | 71 |
| 194 | Simple Pneumonia & Pleurisy w/cc | | 16.5% | 85 | 515 |
| 208 | Respiratory System Diagnosis w/ Ventilator Support <96 Hour | | 17.9% | 24 | 134 |
| 871 | Septicemia or Severe Sepsis w/o MV 96+ Hrs | | 24.2% | 38 | 157 |
| 870 | Septicemia or Severe Sepsis w/ MV 96+ Hrs | | 28.6% | 6 | 21 |
| 193 | Simple Pneumonia & Pleurisy w/mcc | | 20.8% | 36 | 173 |
| 189 | Pulmonary Edema & Respiratory Failure | | 11.0% | 20 | 182 |
| 981 | Extensive OR Procedure Unrelated to Principle Dx | | 25.5% | 12 | 47 |
| 392 | Esophagitis, Gastroent & Misc Digest Disorders w/o MCC | | 9.0% | 43 | 480 |

| 2011 | | | 2010 | | |
|---|---|---|---|---|---|
| 2011Q4-2011Q1 DHMC IP | | | 2010Q4-2010Q1 DHMC IP | | |
| Rate | Num. | Den. | Rate | Num. | Den. |
| 31.6% | 12 | 38 | 34.6% | 9 | 26 |
| 18.9% | 7 | 37 | 23.5% | 8 | 34 |
| 17.2% | 45 | 262 | 15.8% | 40 | 253 |
| 18.7% | 14 | 75 | 16.9% | 10 | 59 |
| 23.9% | 21 | 88 | 24.6% | 17 | 69 |
| 30.8% | 4 | 13 | 25.0% | 2 | 8 |
| 21.5% | 20 | 93 | 20.0% | 16 | 80 |
| 9.6% | 10 | 104 | 12.8% | 10 | 78 |
| 23.3% | 7 | 30 | 29.4% | 5 | 17 |
| 10.7% | 25 | 233 | 7.3% | 18 | 247 |

Figure 23: RIV
METRIC 5
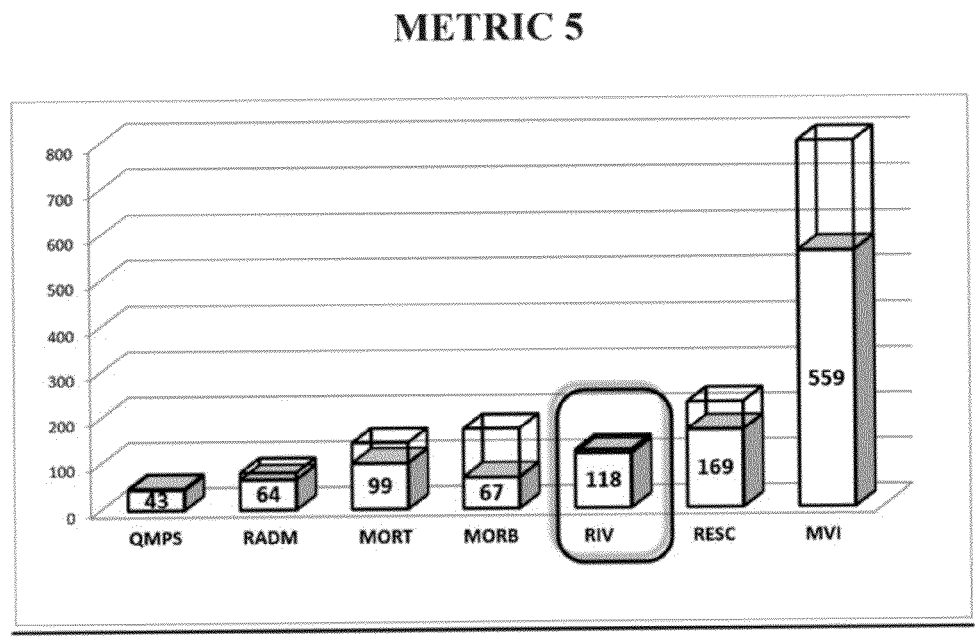
TITLE: Reduction In Variation (RIV)
Score Range: 0 to 126 points (calculated score for this hospital shown as 118 out of 126)
Graphing Color: Light Blue
Graphing Position: Fifth Position, 5th From Left of Horizontal, 5th From Bottom of Stack
Type of Measure: Charge (or Cost) Variation
Score Modified by CMI: Yes
Score Modified by Average Per-Case Charge: No

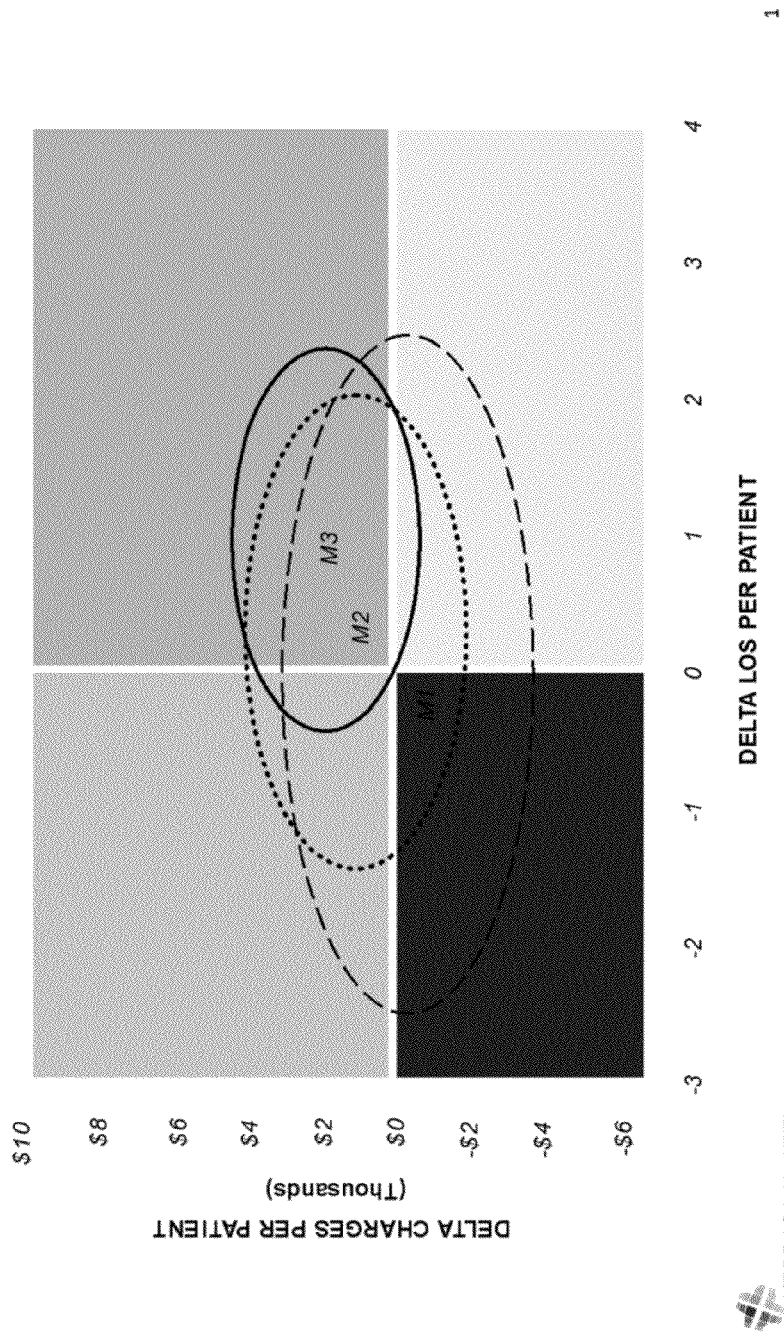
Figure 24: Reduction In Variation (RIV) – 3-Year Trending Model

Figure 25: Reduction In Variation (RIV) – Computation Summary

| Metric 5: Reductions In Variation (RIV) | | | | | |
|---|---|---|---|---|---|
| From Multi Year Comparison | | | | | |
| Overall - 5 Drgs x 5 Service Areas | | | | | |
| Number SubMeasures: | 25 | | | | |
| Significantly Degraded: | 0 | | | | |
| Improved/Unchanged: | 23 | | | | |
| NotMeasurable: | 2 | | | | |
| Net Change #: | 23 | | | | |
| Net Change %: | 100.00% | | | | |
| | | | | 90% of Metric Range/0% of Metric Range | |
| | | Quality Component Range | | Maximum Points -113aximum Points -12.6 | |
| | | 113.40 | | Quality Component  CMI Component | MVI Metric #5 |
| | | x | >> | 113.40          4.42 | 118 |
| | | | | | Range: |
| | | | | | 0 - 126 |
| Pulmonary ( MDC 4 ) | | | | | |
| Number DRGs: | 5 | | | | |
| Significantly Degraded: | 0 | Not Measurable When Measurement or Back Data Volume Too Low for Specific DRG | | | |
| Improved/Unchanged: | 5 | | | | |
| NotMeasurable: | 0 | | | | |
| Net Change #: | 5 | | | | |
| Net Change %: | 100.00% | | | | |
| Cardiology ( MDC 5 ) | | | | | |
| Number DRGs: | 5 | | | | |
| Significantly Degraded: | 0 | Not Measurable When Measurement or Back Data Volume Too Low for Specific DRG | | | |
| Improved/Unchanged: | 5 | | | | |
| NotMeasurable: | 0 | | | | |
| Net Change #: | 5 | | | | |
| Net Change %: | 100.00% | | | | |
| Neuro ( MDC 1 ) | | | | | |
| Number DRGs: | 5 | | | | |
| Significantly Degraded: | 0 | Not Measurable When Measurement or Back Data Volume Too Low for Specific DRG | | | |
| Improved/Unchanged: | 4 | | | | |
| NotMeasurable: | 1 | | | | |
| Net Change #: | 4 | | | | |
| Net Change %: | 100.00% | | | | |
| Orthopedics ( MDC 8 ) | | | | | |
| Number DRGs: | 5 | | | | |
| Significantly Degraded: | 0 | Not Measurable When Measurement or Back Data Volume Too Low for Specific DRG | | | |
| Improved/Unchanged: | 4 | | | | |
| NotMeasurable: | 1 | | | | |
| Net Change #: | 4 | | | | |
| Net Change %: | 100.00% | | | | |
| INFD ( MDC 18 ) | | | | | |
| Number DRGs: | 5 | | | | |
| Significantly Degraded: | 0 | Not Measurable When Measurement or Back Data Volume Too Low for Specific DRG | | | |
| Improved/Unchanged: | 5 | | | | |
| NotMeasurable: | 0 | | | | |
| Net Change #: | 5 | | | | |
| Net Change %: | 100.00% | | | | |

Figure 26A: Reduction In Variation (RIV) – Computation Detail

Metric 5 Reductions In Variation
[All Payors / Top 5 Drg By $ For 5 Selected Services - DHMC, IP Only]
Inpatient Reductions In Variation (RIV) - Improvement Is Variation Decrease

| | | | 2012 vs 2011 & 2010 Comparison | | | |
|---|---|---|---|---|---|---|
| Pulmonary ( MDC 4 ) | | | | | | |
| KEY | Title | Mean | Delta | Imp/Unc | SigDeg | SigTest |
| 194 | Simple Pneumonia & Pleurisy w/CC | $12,775 | $1,520 | 1 | 0 | 0 |
| 207 | Respiratory System Diangosis s/Ventilator Support 96+Hrs Ventilator | $83,940 | -$5,792 | 1 | 0 | 0 |
| 208 | Respiratory System Diangosis s/Ventilator Support <96Hrs Ventilator | $34,666 | -$2,636 | 1 | 0 | 0 |
| 193 | Simple Pneumonia & Pleurisy w/CC | $37,646 | -$5,355 | 1 | 0 | 0 |
| 189 | Pulmonary Edema & Respiratory Failure | $21,637 | -$553 | 1 | 0 | 0 |
| | | | | | | |
| Cardiology ( MDC 5 ) | | | | | | |
| KEY | Title | Mean | Delta | Imp/Unc | SigDeg | SigTest |
| 291 | Heart Failure & Shock w/MCC | $35,316 | $4,715 | 1 | 0 | 0 |
| 292 | Heart Failure & Shock w/CC | $15,890 | $1,427 | 1 | 0 | 0 |
| 312 | Syncope & Collapse | $12,126 | -$2,210 | 1 | 0 | 0 |
| 229 | Other Cardiothoracic Procedures w/cc | $20,450 | $2,673 | 1 | 0 | 0 |
| 228 | Other Cardiothoracic Procedures wmcc | $37,696 | -$55,176 | 1 | 0 | 1 |
| | | | | | | |
| Neuro ( MDC 1 ) | | | | | | |
| KEY | Title | | Delta | Imp/Unc | SigDeg | SigTest |
| 065 | Intracranial Hemorrhage or Cerebral Infarction w/cc | $9,628 | $1,154 | 1 | 0 | 0 |
| 066 | Intracranial Hemorrhage or Cerebral Infarction w/o cc/mcc | $7,354 | $2,054 | 1 | 0 | 0 |
| 064 | Intracranial Hemorrhage or Cerebral Infarction w/mcc | $52,410 | $3,018 | 1 | 0 | 0 |
| 069 | Tansient Ischemia | $5,260 | $352 | 1 | 0 | 0 |
| 086 | Traumatic Stupor & Coma, Coma <1 Hr Age >17 w/ CC | $5,676 | $1,622 | 0 | 0 | 1 |
| | | | | | | |
| Orthopedics ( MDC 8 ) | | | | | | |
| KEY | Title | | | | | |
| 552 | Medical Back Problems w/o MCC | $13,628 | -$1,270 | 1 | 0 | 0 |
| 481 | HIP & Femur Procedures Except Major Joint w/cc | $23,043 | $4,366 | 1 | 0 | 0 |
| 464 | Wnd Debrid & Skin Grft Exc Hand, For Musculo-Conn Tiss Dis | $37,943 | -$11,040 | 1 | 0 | 0 |
| 556 | Signs & Symptoms of Musculoskeletal System & Conn Tissue | $19,120 | $76 | 1 | 0 | 0 |
| 469 | Major Joint Replacement or Reattachemnt of Lower Extremity | $6,320 | -$2,528 | 0 | 0 | 1 |
| | | | | | | |
| INFD - ( MDC 18 ) | | | | | | |
| KEY | Title | | | | | |
| 853 | Infectious & Parasitic Disease w OR Procedure w/MCC | $95,179 | -$17,913 | 1 | 0 | 0 |
| 871 | Septicemia or severe sepsis w/o MV 96+ hours w/MCC | $33,798 | $352 | 1 | 0 | 0 |
| 870 | Septicemia or severe sepsis w/ MV 96+ hours | $96,067 | -$10,833 | 1 | 0 | 0 |
| 872 | Septicemia or severe sepsis w/o MV 96+ hours w/o MCC | $17,266 | -$2,875 | 1 | 0 | 0 |
| 854 | Infectious & Parasitic Disease w OR Procedure w/CC | $19,011 | -$7,604 | 1 | 0 | 0 |
| | Metric 5 Net: | $30,154 | -$4,426 | 23 | 0 | 3 |

Figure 26B: Reduction In Variation (RIV) – Computation Detail

| | 2012 Measurement Period | | | | | 2011 & 2010 Back Period | | | |
|---|---|---|---|---|---|---|---|---|---|
| Variation | Cases | VCI_LL | VCI_UL | | Variation | Cases | VCI_LL | VCI_UL |
| $12,015 | 122 | $10,673 | $13,745 | | $13,535 | 264 | $12,471 | $14,800 |
| $81,044 | 25 | $63,719 | $113,524 | | $86,836 | 54 | $72,996 | $107,200 |
| $33,348 | 43 | $27,606 | $42,554 | | $35,984 | 95 | $31,493 | $41,979 |
| $34,969 | 34 | $28,413 | $46,733 | | $40,324 | 77 | $34,807 | $47,934 |
| $21,360 | 53 | $17,929 | $26,429 | | $21,914 | 106 | $19,308 | $25,338 |
| Variation | Cases | VCI_LL | VCI_UL | | Variation | Cases | VCI_LL | VCI_UL |
| $37,674 | 28 | $29,969 | $51,595 | | $32,959 | 69 | $28,230 | $39,605 |
| $15,176 | 23 | $11,850 | $22,030 | | $16,603 | 55 | $13,977 | $20,452 |
| $11,021 | 42 | $9,123 | $14,218 | | $13,231 | 91 | $11,548 | $15,491 |
| $21,786 | 10 | $14,985 | $39,773 | | $19,113 | 20 | $14,535 | $27,916 |
| $10,108 | 8 | $6,683 | $20,573 | | $65,284 | 16 | $48,225 | $101,039 |
| $9,051 | 8 | $6,148 | $21,008 | | $10,205 | 15 | $7,471 | $16,094 |
| $8,381 | 5 | $5,227 | $25,068 | | $6,327 | 10 | $4,352 | $11,551 |
| $53,919 | 10 | $37,907 | $107,514 | | $50,901 | 20 | $38,709 | $74,344 |
| $5,436 | 4 | $3,080 | $20,270 | | $5,084 | 7 | $3,276 | $11,195 |
| $6,487 | 1 | $0 | $0 | | $4,866 | 2 | $2,171 | $155,259 |
| $12,993 | 12 | $9,343 | $22,392 | | $14,263 | 26 | $11,186 | $19,689 |
| $25,226 | 3 | $14,530 | $1,039,220 | | $20,860 | 900 | $19,939 | $21,871 |
| $32,423 | 3 | $16,881 | $203,768 | | $43,463 | 7 | $28,007 | $95,708 |
| $19,158 | 3 | $10,774 | $130,048 | | $19,082 | 8 | $12,617 | $38,837 |
| $5,056 | 1 | $0 | $0 | | $7,585 | 3 | $3,949 | $47,667 |
| $86,222 | 16 | $63,693 | $133,446 | | $104,136 | 39 | $85,104 | $134,208 |
| $33,974 | 39 | $27,887 | $43,977 | | $33,622 | 95 | $29,426 | $39,224 |
| $90,650 | 8 | $61,574 | $210,416 | | $101,483 | 17 | $75,581 | $154,450 |
| $15,828 | 9 | $10,691 | $30,323 | | $18,704 | 24 | $14,537 | $26,237 |
| $15,209 | 2 | $6,785 | $485,311 | | $22,813 | 5 | $13,668 | $65,554 |

Figure 27A: Reduction In Variation (RIV) – "Measurement Period" Data

| Metric 5 | Reductions In Variation | | | | |
|---|---|---|---|---|---|
| | [All Payors / Top 5 Drg By $ / 5 Selected Services - DHMC, IP Only] | | | | |
| | Inpatient Reductions in Variation (RIV) - Improvement Is Variation Decrease | | | | |
| | | | | 2012 Aggregated | |
| | | Variation | Cases | VCI_LL | VCI_UL |
| Pulmonary ( MDC 4 ) | | | | | |
| KEY | Title | | | | |
| 194 | Simple Pneumonia & Pleurisy w/CC | $12,015 | 122 | $10,673 | $13,745 |
| 207 | Respiratory System Diangosis s/Ventilator Support 96+Hrs Ventilat | $81,044 | 25 | $63,719 | $113,524 |
| 208 | Respiratory System Diangosis s/Ventilator Support <96Hrs Ventilat | $33,348 | 43 | $27,606 | $42,554 |
| 193 | Simple Pneumonia & Pleurisy w/CC | $34,969 | 34 | $28,413 | $46,733 |
| 189 | Pulmonary Edema & Respiratory Failure | $21,360 | 53 | $17,929 | $26,429 |
| Cardiology ( MDC 5 ) | | | | | |
| KEY | Title | | | | |
| 291 | Heart Failure & Shock w/MCC | $37,674 | 28 | $29,969 | $51,595 |
| 292 | Heart Failure & Shock w/CC | $15,176 | 23 | $11,860 | $22,030 |
| 312 | Syncope & Collapse | $11,021 | 42 | $9,123 | $14,218 |
| 229 | Other Cardiothoracic Procedures w/cc | $21,786 | 10 | $14,985 | $39,773 |
| 228 | Other Cardiothoracic Procedures wmcc | $10,108 | 8 | $6,683 | $20,573 |
| Neuro ( MDC 1 ) | | | | | |
| KEY | Title | | | | |
| 065 | Intracranial Hemorrhage or Cerebral Infarction w/cc | $9,051 | 8 | $6,148 | $21,008 |
| 066 | Intracranial Hemorrhage or Cerebral Infarction w/o cc/mcc | $8,381 | 5 | $5,227 | $25,068 |
| 064 | Intracranial Hemorrhage or Cerebral Infarction w/mcc | $53,919 | 10 | $37,907 | $107,514 |
| 069 | Tansient Ischemia | $5,436 | 4 | $3,080 | $20,270 |
| 086 | Traumatic Stupor & Coma, Coma <1 Hr Age >17 w/ CC | $6,487 | 1 | $0 | $0 |
| Orthopedics ( MDC 8 ) | | | | | |
| KEY | Title | | | | |
| 552 | Medical Back Problems w/o MCC | $12,993 | 12 | $9,343 | $22,392 |
| 481 | HIP & Femur Procedures Except Major Joint w/cc | $25,226 | 3 | $14,530 | $1,039,220 |
| 464 | Wnd Debrid & Skin Grft Exc Hand, For Musculo-Conn Tiss Dis | $32,423 | 3 | $16,881 | $203,768 |
| 556 | Signs & Symptoms of Musculoskeletal System & Conn Tissue | $19,158 | 3 | $10,774 | $130,048 |
| 469 | Major Joint Replacement or Reattachemnt of Lower Extremity | $5,056 | 1 | $0 | $0 |
| INFD - ( MDC 18 ) | | | | | |
| KEY | Title | | | | |
| 853 | Infectious & Parasitic Disease w OR Procedure w/MCC | $86,222 | 16 | $63,693 | $133,446 |
| 871 | Septicemia or severe sepsis w/o MV 96+ hours w/MCC | $33,974 | 39 | $27,887 | $43,977 |
| 870 | Septicemia or severe sepsis w/ MV 96+ hours | $90,650 | 8 | $61,574 | $210,416 |
| 872 | Septicemia or severe sepsis w/o MV 96+ hours w/o MCC | $15,828 | 9 | $10,691 | $30,323 |
| 854 | Infectious & Parasitic Disease w OR Procedure w/CC | $15,209 | 2 | $6,785 | $485,311 |

Figure 27B: Reduction In Variation (RIV) – "Measurement Period" Data

| | 2012 2012Q4-2012Q1 DHMC IP | | | |
|---|---|---|---|---|
| Variation | Cases | VCI_LL | VCI_UL | |
| $12,015 | 122 | $10,673 | $13,745 | |
| $81,044 | 25 | $63,719 | $113,524 | |
| $33,348 | 43 | $27,606 | $42,554 | |
| $34,969 | 34 | $28,413 | $46,733 | |
| $21,360 | 53 | $17,929 | $26,429 | |
| | | | | |
| $37,674 | 28 | $29,969 | $51,595 | |
| $15,176 | 23 | $11,860 | $22,030 | |
| $11,021 | 42 | $9,123 | $14,218 | |
| $21,786 | 10 | $14,985 | $39,773 | |
| $10,108 | 8 | $6,683 | $20,573 | |
| | | | | |
| $9,051 | 8 | $6,148 | $21,008 | |
| $8,381 | 5 | $5,227 | $25,068 | |
| $53,919 | 10 | $37,907 | $107,514 | |
| $5,436 | 4 | $3,080 | $20,270 | |
| $6,487 | 1 | $0 | $0 | |
| | | | | |
| $12,993 | 12 | $9,343 | $22,392 | |
| $25,226 | 3 | $14,530 | $1,039,220 | |
| $32,423 | 3 | $16,881 | $203,768 | |
| $19,158 | 3 | $10,774 | $130,048 | |
| $5,056 | 1 | $0 | $0 | |
| | | | | |
| $86,222 | 16 | $63,693 | $133,446 | |
| $33,974 | 39 | $27,887 | $43,977 | |
| $90,650 | 8 | $61,574 | $210,416 | |
| $15,828 | 9 | $10,691 | $30,323 | |
| $15,209 | 2 | $6,785 | $485,311 | |

Figure 28A: Reduction In Variation (RIV) – "Back Period" Data

| Metric 5 | Reductions In Variation<br>[All Payors / Top 5 Drg By $ / 5 Selected Services - DHMC, IP Only]<br>Inpatient Reductions In Variation (RIV) - Improvement Is Variation Decrease | | 2011 & 2010 Aggregated | | | |
|---|---|---|---|---|---|---|
| | | Variation | Cases | VCI_LL | VCI_UL | |
| Pulmonary ( MDC 4 ) | | | | | | |
| KEY | Title | | | | | |
| 194 | Simple Pneumonia & Pleurisy w/CC | $13,535 | 264 | $12,471 | $14,800 | |
| 207 | Respiratory System Diangosis s/Ventilator Support 96+Hrs Ventil | $86,836 | 54 | $72,996 | $107,200 | |
| 208 | Respiratory System Diangosis s/Ventilator Support <96Hrs Ventil | $35,984 | 95 | $31,493 | $41,979 | |
| 193 | Simple Pneumonia & Pleurisy w/CC | $40,324 | 77 | $34,807 | $47,934 | |
| 189 | Pulmonary Edema & Respiratory Failure | $21,914 | 106 | $19,308 | $25,338 | |
| Cardiology ( MDC 5 ) | | | | | | |
| KEY | Title | Variation | Cases | VCI_LL | VCI_UL | |
| 291 | Heart Failure & Shock w/MCC | $32,959 | 69 | $28,230 | $39,605 | |
| 292 | Heart Failure & Shock w/CC | $16,603 | 55 | $13,977 | $20,452 | |
| 312 | Syncope & Collapse | $13,231 | 91 | $11,548 | $15,491 | |
| 229 | Other Cardiothoracic Procedures w/cc | $19,113 | 20 | $14,535 | $27,916 | |
| 228 | Other Cardiothoracic Procedures wmcc | $65,284 | 16 | $48,225 | $101,039 | |
| Neuro ( MDC 1 ) | | | | | | |
| KEY | Title | | | | | |
| 065 | Intracranial Hemorrhage or Cerebral Infarction w/cc | $10,205 | 15 | $7,471 | $16,094 | |
| 066 | Intracranial Hemorrhage or Cerebral Infarction w/o cc/mcc | $6,327 | 10 | $4,352 | $11,551 | |
| 064 | Intracranial Hemorrhage or Cerebral Infarction w/mcc | $50,901 | 20 | $38,709 | $74,344 | |
| 069 | Tansient Ischemia | $5,084 | 7 | $3,276 | $11,195 | |
| 086 | Traumatic Stupor & Coma, Coma <1 Hr Age >17 w/ CC | $4,866 | 2 | $2,171 | $155,259 | |
| Orthopedics ( MDC 8 ) | | | | | | |
| KEY | Title | | | | | |
| 552 | Medical Back Problems w/o MCC | $14,263 | 26 | $11,186 | $19,689 | |
| 481 | HIP & Femur Procedures Except Major Joint w/cc | $20,860 | 900 | $19,939 | $21,871 | |
| 464 | Wnd Debrid & Skin Grft Exc Hand, For Musculo-Conn Tiss Dis | $43,463 | 7 | $28,007 | $95,708 | |
| 556 | Signs & Symptoms of Musculoskeletal System & Conn Tissue | $19,082 | 8 | $12,617 | $38,837 | |
| 469 | Major Joint Replacement or Reattachemnt of Lower Extremity | $7,585 | 3 | $3,949 | $47,667 | |
| INFD - ( MDC 18 ) | | | | | | |
| KEY | Title | | | | | |
| 853 | Infectious & Parasitic Disease w OR Procedure w/MCC | $104,136 | 39 | $85,104 | $134,208 | |
| 871 | Septicemia or severe sepsis w/o MV 96+ hours w/MCC | $33,622 | 95 | $29,426 | $39,224 | |
| 870 | Septicemia or severe sepsis w/ MV 96+ hours | $101,483 | 17 | $75,581 | $154,450 | |
| 872 | Septicemia or severe sepsis w/o MV 96+ hours w/o MCC | $18,704 | 24 | $14,537 | $26,237 | |
| 854 | Infectious & Parasitic Disease w OR Procedure w/CC | $22,813 | 5 | $13,668 | $65,554 | |

Figure 28B: Reduction In Variation (RIV) – "Back Period" Data

| | 2011 2011Q4-2011Q1 DHMC IP | | | | 2010 2010Q4-2010Q1 DHMC IP | | | |
|---|---|---|---|---|---|---|---|---|
| Variation | Cases | VCl_LL | VCl_UL | Variation | Cases | VCl_LL | VCl_UL |
| $15,581 | 163 | $14,053 | $17,484 | $11,489 | 101 | $10,094 | $13,336 |
| $79,005 | 28 | $62,463 | $107,537 | $94,667 | 26 | $74,243 | $130,679 |
| $41,003 | 53 | $34,416 | $50,732 | $30,964 | 42 | $25,477 | $39,484 |
| $45,177 | 48 | $37,608 | $56,588 | $35,470 | 29 | $28,148 | $47,971 |
| $18,510 | 64 | $15,767 | $22,418 | $25,317 | 42 | $20,831 | $32,283 |
| Variation | Cases | VCl_LL | VCl_UL | Variation | Cases | VCl_LL | VCl_UL |
| $37,215 | 37 | $30,264 | $48,341 | $28,702 | 32 | $23,010 | $38,159 |
| $20,961 | 40 | $17,170 | $26,915 | $12,245 | 15 | $8,965 | $19,312 |
| $17,333 | 41 | $14,231 | $22,178 | $9,128 | 50 | $7,625 | $11,375 |
| $38,226 | 10 | $26,293 | $69,786 | $0 | 10 | $0 | $0 |
| $40,417 | 9 | $27,300 | $77,430 | $90,150 | 7 | $58,092 | $198,516 |
| $9,434 | 10 | $6,489 | $17,223 | $10,976 | 5 | $6,576 | $31,540 |
| $10,091 | 8 | $6,672 | $20,538 | $2,563 | 2 | $1,143 | $81,786 |
| $37,056 | 10 | $25,488 | $67,650 | $64,745 | 10 | $44,534 | $118,199 |
| $3,982 | 4 | $2,256 | $14,847 | $6,186 | 3 | $3,221 | $38,877 |
| $0 | 0 | #NUM! | #NUM! | $9,731 | 2 | $4,341 | $310,518 |
| $10,901 | 15 | $7,981 | $17,192 | $17,625 | 11 | $12,315 | $30,931 |
| $41,720 | 5 | $24,996 | $119,885 | $0 | 0 | $0 | $0 |
| $57,648 | 4 | $32,657 | $214,943 | $29,278 | 3 | $15,244 | $184,004 |
| $19,490 | 5 | $11,677 | $56,006 | $18,674 | 3 | $9,723 | $117,361 |
| $15,169 | 3 | $7,898 | $95,333 | $0 | 0 | $0 | $0 |
| $94,466 | 26 | $74,086 | $130,402 | $113,805 | 13 | $81,608 | $187,862 |
| $35,774 | 60 | $30,323 | $43,632 | $31,470 | 35 | $25,455 | $41,232 |
| $124,803 | 12 | $88,410 | $211,900 | $78,163 | 5 | $46,830 | $224,606 |
| $17,654 | 17 | $13,148 | $26,868 | $19,753 | 7 | $12,729 | $43,497 |
| $45,626 | 4 | $25,847 | $170,119 | $0 | 1 | $0 | $0 |

Figure 29: RESC
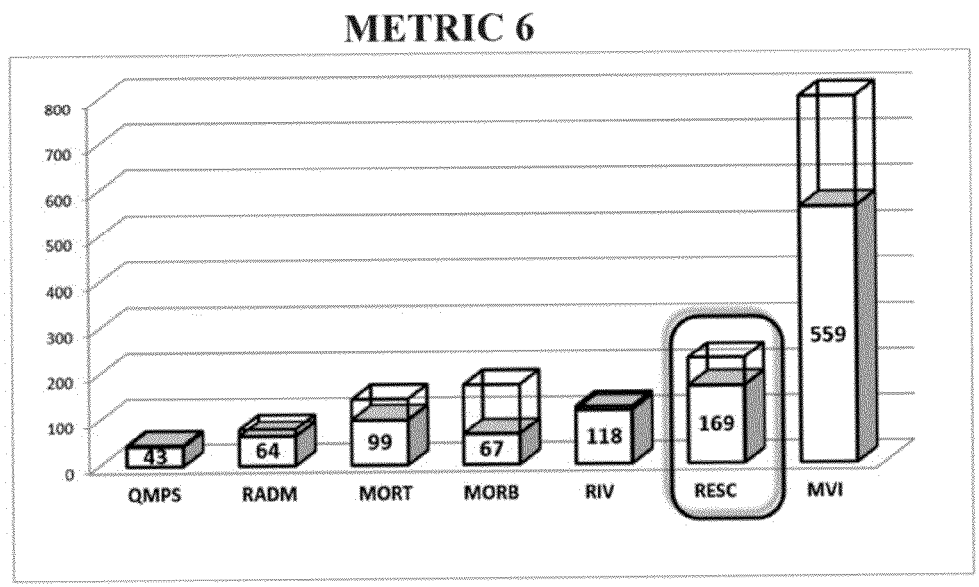
TITLE: Resource Consumption (RESC)
Score Range: 0 to 230 points (calculated score for this hospital shown as 169 out of 230)
Graphing Color: Green
Graphing Position: Sixth Position, 6th From Left of Horizontal, 6th From Bottom of Stack
Type of Measure: Charge (or Cost) Inflation Trend
Score Modified by CMI: Yes
Score Modified by Average Per-Case Charge: Yes Figure 30: Resource Consumption (RES) – Computation Summary
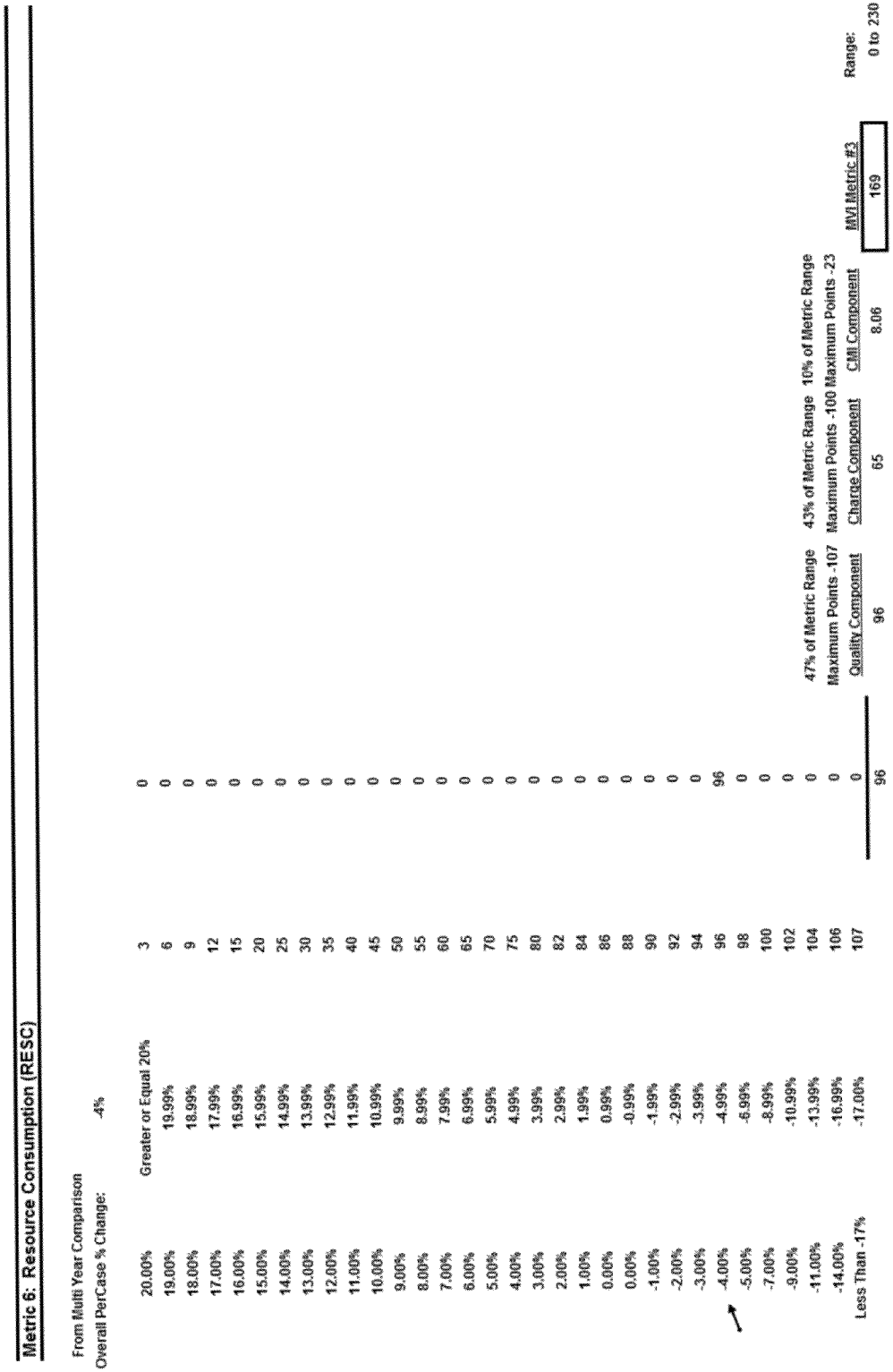

Figure 31: Recourse Consumption (RES) – Computation Detail

| Metric 6 Resource Consumption | | | | | | | |
|---|---|---|---|---|---|---|---|
| [All Payors / All DRGs For 5 Selected Services - DHMC, IP] | | | | 2012 vs (2011 & 2010) 2012 Projection Comparison | | | |
| Inpatient Changes in Resource Consumption - Improvement Is Charge Decrease | | | | | | | |
| Pulmonary ( MDC 4 ) | | | Change | Mean | Delta | Imp/Unc | Deg |
| KEY | Title | | | | | | |
| RESP (4) | Respiratory System | | -4.01% | $40,098.5 | -$1,642 | 1 | 0 |
| Cardiology ( MDC 5 ) | | | | | | | |
| KEY | Title | | | | | | |
| CIRC (5) | Circulatory System | | -5.81% | $42,193.6 | -$2,526 | 1 | 0 |
| Neurology ( MDC 1 - Medical DRGs) | | | | | | | |
| KEY | Title | | | | | | |
| NERV (1) | Nervous System - Medical | | -2.76% | $36,543.0 | -$1,022 | 1 | 0 |
| Orthopedics ( MDC 8 ) | | | | | | | |
| KEY | Title | | | | | | |
| MUSC (8) | Musculoskeletal System (and Connective Tissue) | | -4.21% | $54,210.3 | -$2,333 | 1 | 0 |
| INFD. - ( MDC 18 ) | | | | | | | |
| KEY | Title | | | | | | |
| INFD (18) | Infections | | -3.35% | $80,220.4 | -$2,734 | 1 | 0 |
| | | | -4.03% | $50,653 | -$2,051 | 5 | 0 |
| | | | Metric 6 Net: | | | | |

| 2012 Measurement Period | | | | 2011 & 2010 Back Period | | | |
|---|---|---|---|---|---|---|---|
| PerCase | Cases | Charges | PerCase | Cases | Charges | | |
| $39,277 | 644 | $25,294,545 | $40,920 | 1389 | $56,837,405 | | |
| $40,931 | 269 | $11,024,021 | $43,456 | 581 | $25,248,209 | | |
| $36,032 | 92 | $3,302,922 | $37,054 | 194 | $7,188,500 | | |
| $53,044 | 76 | $4,031,336 | $55,377 | 178 | $9,857,054 | | |
| $78,854 | 98 | $7,701,359 | $81,587 | 228 | $18,601,882 | | |

Figure 32: Resource Consumption (RES) – "Measurement Period" Data

| Metric 6 | Resource Consumption [All Payors / All DRGs / 5 Selected Services - DHMC, IP] Inpatient Changes in Resource Consumption - Improvement Is Charge Decrease | | | | | | |
|---|---|---|---|---|---|---|---|
| | | 2012 Aggregated | | | 2012 2012Q4-2012Q1 DHMC IP | | |
| | | PerCase | Cases | Charges | PerCase | Cases | Charges |
| Pulmonary ( MDC 4 ) | | | | | | | |
| KEY | Title | | | | | | |
| RESP (4) | Respiratory System | $39,277 | 644 | $25,294,545 | $39,277 | 644 | $25,294,545 |
| Cardiology ( MDC 5 ) | | | | | | | |
| KEY | Title | | | | | | |
| CIRC (5) | Circulatory System | $40,931 | 269 | $11,024,021 | $40,931 | 269 | $11,024,021 |
| Neurology ( MDC 1 - Medical DRGs) | | | | | | | |
| KEY | Title | | | | | | |
| NERV (1) | Nervous System - Medical | $36,032 | 92 | $3,302,922 | $36,032 | 92 | $3,302,922 |
| Orthopedics ( MDC 8 ) | | | | | | | |
| KEY | Title | | | | | | |
| MUSC (8) | Musculoskeletal System (and Connective Tissue) | $53,044 | 76 | $4,031,336 | $53,044 | 76 | $4,031,336 |
| INFD - ( MDC 18 ) | | | | | | | |
| KEY | Title | | | | | | |
| INFD (18) | Infections | $78,854 | 98 | $7,701,359 | $78,854 | 98 | $7,701,359 |

Figure 33: Resource Consumption (RES) – "Back Period" Data

| Metric 6 | Resource Consumption |
|---|---|
| | [All Payors / All DRGs / 5 Selected Services - DHMC, IP] |
| | Inpatient Changes in Resource Consumption - Improvement Is Charge Decrease |

Pulmonary ( MDC 4 )
KEY         Title
RESP (4)    Respiratory System

Cardiology ( MDC 5 )
KEY         Title
CIRC (5)    Circulatory System

Neurology ( MDC 1 - Medical DRGs)
KEY         Title
NERV (1)    Nervous System - Medical Orthopedics ( MDC 8 )
KEY         Title
MUSC (8)    Musculoskeletal System (and Connective Tissue)

INFD - ( MDC 18 )
KEY         Title
INFD (18)   Infections

|  | 2011 2011Q4-2011Q1 DHMC IP | | | 2010 2010Q4-2010Q1 DHMC IP | | | 2011 & 2010 Aggregated | | |
|---|---|---|---|---|---|---|---|---|---|
|  | PerCase | Cases | Charges | PerCase | Cases | Charges | PerCase | Cases | Charges |
|  | $42,186 | 794 | $33,495,482 | $39,230 | 595 | $23,341,923 | $40,920 | 1389 | $56,837,405 |
|  | $46,344 | 302 | $13,995,757 | $40,331 | 279 | $11,252,452 | $43,456 | 581 | $25,248,209 |
|  | $37,980 | 105 | $3,987,901 | $35,962 | 89 | $3,200,599 | $37,054 | 194 | $7,188,500 |
|  | $52,959 | 96 | $5,084,077 | $58,207 | 82 | $4,772,977 | $55,377 | 178 | $9,857,054 |
|  | $91,709 | 144 | $13,206,154 | $64,235 | 84 | $5,395,728 | $81,587 | 228 | $18,601,882 |

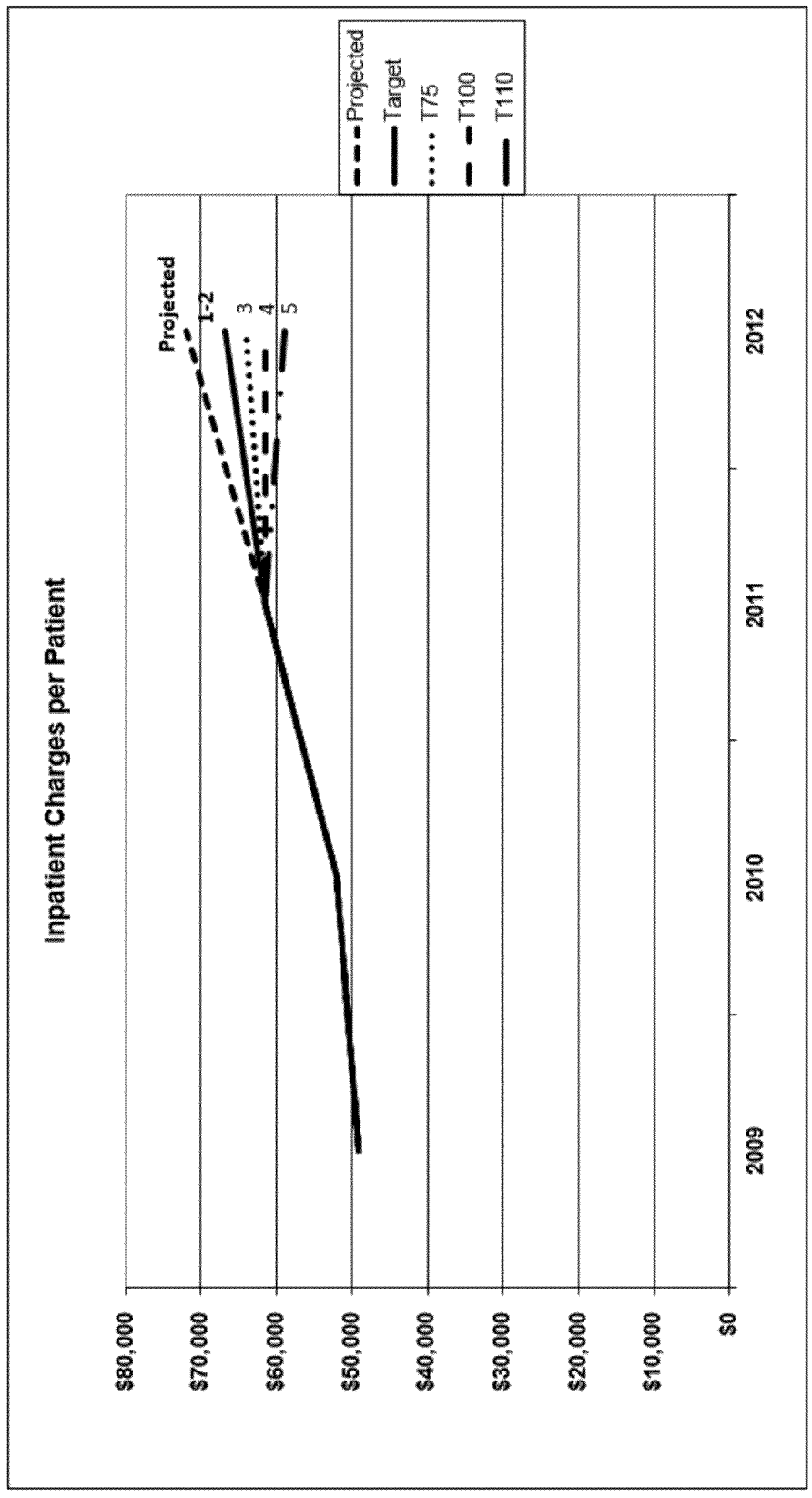
Figure 34: Charge (or Cost) Projection

Figure 35: Back Year Dollars Per-Case

| | Per Case Chrg 2009 | Per Case Chrg 2010 | Per Case Chrg 2011 | # of Cases 2011 | Total Chrg 2011 |
|---|---|---|---|---|---|
| Service 1 $ = Respiratory | $35,076 | $39,230 | $42,186 | 794 | $33,495,684 |
| Service 2 $ = Circulatory | $34,466 | $40,331 | $46,344 | 302 | $13,995,888 |
| Service 3 $ = Neurology | $33,584 | $35,962 | $37,694 | 105 | $3,957,870 |
| Service 4 $ = Orthopaedics | $78,752 | $78,752 | $86,741 | 1,603 | $139,045,823 |
| Service 5 $ = Infections | $69,265 | $67,806 | $91,709 | 144 | $13,206,096 |
| Service 6 $ = Other Clinical Service Areas | $43,406 | $50,208 | $64,548 | 3,550 | $229,143,625 |
| Total Charges, Facility Inpatient: | $49,091 | $52,048 | $61,537 | 6,498 | $432,844,986 |

Figure 36: Projection from historical percent change

| | 3 year Ave. % Change $ | Prj. Case Chrg 2012 | Prj. # of Cases Assum. 2012=2011 | Case Prj Modifier Ratio | Prj. Total Chrg 2012 |
|---|---|---|---|---|---|
| Service 1 $ = Respiratory | 20.00% | $50,623 | 794 | 1.00 | $40,194,821 |
| Service 2 $ = Circulatory | 20.00% | $55,613 | 302 | 1.00 | $16,795,066 |
| Service 3 $ = Neurology | 12.24% | $42,307 | 105 | 1.00 | $4,442,233 |
| Service 4 $ = Orthopaedics | 10.14% | $95,540 | 1,603 | 1.00 | $153,151,332 |
| Service 5 $ = Infections | 20.00% | $110,051 | 144 | 1.00 | $15,847,315 |
| Service 6 $ = Other Clinical Service Areas | 20.00% | $77,457 | 3,550 | 1.00 | $274,972,350 |
| Total Charges, Facility Inpatient: | 17.06% | $71,932 | 6,498 | 1.00 | $505,403,117 |

Figure 37: Target from Percent Change Goal

| | Tgt. % Change $ | Tgt. Case Chrg 2012 | Tgt # Cases Assum. 2012=2011 | Tgt. Total Chrg Act. 2012 |
|---|---|---|---|---|
| Service 1 $ = Respiratory | 10.00% | $46,405 | 794 | $36,845,252 |
| Service 2 $ = Circulatory | 10.00% | $50,978 | 302 | $15,395,477 |
| Service 3 $ = Neurology | 6.12% | $40,000 | 105 | $4,200,051 |
| Service 4 $ = Orthopaedics | 5.07% | $91,141 | 1,603 | $146,098,578 |
| Service 5 $ = Infections | 10.00% | $100,880 | 144 | $14,526,706 |
| Service 6 $ = Other Clinical Service Areas | 10.00% | $71,002 | 3,550 | $252,057,988 |
| Total Charges, Facility Inpatient: | 8.53% | $66,734 | 6,498 | $469,124,052 |

Figure 38: Actual Results of Measurement Period

|  | Act. Case Chrg 2012 | Act # Cases 2012 | Act. Total Chrg 2012 |
|---|---|---|---|
| Service 1 $ = Respiratory | $43,873 | 802 | $35,183,866 |
| Service 2 $ = Circulatory | $48,198 | 305 | $14,701,281 |
| Service 3 $ = Neurology | $39,202 | 106 | $4,157,347 |
| Service 4 $ = Orthopaedics | $90,211 | 1619 | $146,053,732 |
| Service 5 $ = Infections | $95,377 | 145 | $13,871,683 |
| Service 6 $ = Other Clinical Service Areas | $67,129 | 3586 | $240,692,464 |
| Total Charges, Facility Inpatient: | $63,998 | 6,563 | $454,660,373 |

Figure 39: Gross Savings

| | Projected 2012 | Target 2012 | Actual 2012 | Projection-Actual |
|---|---|---|---|---|
| Service 1 $ = Respiratory | $40,194,821 | 36,845,252 | 35,183,866 | $5,010,954.33 |
| Service 2 $ = Circulatory | $16,795,066 | 15,395,477 | 14,701,281 | $2,093,784.84 |
| Service 3 $ = Neurology | $4,442,233 | 4,200,051 | 4,157,347 | $284,886.31 |
| Service 4 $ = Orthopaedics | $153,151,332 | 146,098,578 | 146,053,732 | $7,097,599.97 |
| Service 5 $ = Infections | $15,847,315 | 14,526,706 | 13,871,683 | $1,975,631.96 |
| Service 6 $ = Other Clinical Service Areas | $274,972,350 | 252,057,988 | 240,692,464 | $34,279,886.30 |
| Total Charges, Facility Inpatient: | $505,403,117 | $469,124,052 | $454,660,373 | $50,742,744 |

Figure 40: Cost Ratios

Charge To Cost Ratio: 24%

Ratio of Costs that are Fixed & Indirect: 46%

Figure 41: The Physicians

Participating Physicians By Service Area:

| | |
|---|---|
| Service 1 = Respiratory | 10 |
| Service 2 = Circulatory | 5 |
| Service 3 = Neurology | 7 |
| Service 4 = Orthopaedics | 2 |
| Service 5 = Infections | 5 |
| Total Top Inpatient Facility Services: | 29 |
| Service 6 = Other Clinical Service Areas | 75 |
| Total All Inpatient Facility Services: | 104 |

Figure 42: The Physician Bonus By Quality Metric

1. Quality Measures & Patient Satisfaction (QMPS):
   bonus distributed to all participating MDs QMPS - Total Bonus: $353,210
   Bonus per MD: $3,396

2. Re-Admission Rate Composite (RADM)
   bonus distributed to all participating MDs RADM - Total Bonus: $511,509
   Bonus per MD: $4,918

3. Risk Adjusted Mortality Rate Analysis (MORT):
   bonus distributed to all participating MDs MORT - Total Bonus: $699,103
   Bonus per MD: $6,722

4. Risk Adjusted Morbidity Rate Analysis (MORB):
   bonus distributed to top service MDs MORB - Total Bonus: $488,001
   Bonus per MD: $16,828

5. Reduction in Variation (RIV) of Charges:
   bonus distributed to top service MDs RIV - Total Bonus: $1,190,372
   Bonus per MD: $41,047

6. Resource Consumption (RESC):
   (Implied Through Spending Reduction)

Total Bonus: $3,242,194
   Bonus per MD: $72,912

Figure 43: QMPS Measurement Factor

Measurement Factor;

| | | |
|---|---|---|
| Medical Value Index Score: | 43 | |
| Score Range: | 46 | |

| Index % | | Bonus Rate Max | | Bonus Rate |
|---|---|---|---|---|
| 92.5% | × | 3.00 | = | 2.77 |

Figure 44: QMPS Bonus Formula

Bonus Formula;

Total $
2012 Projection (builds target-actual portion scale)
$505,403,117

| Scale To Determine Base Portion Amount of Actual (or Target) | | | Bonus Level | | Bonus Rate | | Total Bonus |
|---|---|---|---|---|---|---|---|
| $505,403,117 | Greater or Equal | 0.0040% | $0 | × | 2.77 | = | $0 |
| $495,295,055 | $505,403,116 | 0.0080% | $0 | × | 2.77 | = | $0 |
| $485,186,992 | $495,295,054 | 0.0120% | $0 | × | 2.77 | = | $0 |
| $475,078,930 | $485,186,991 | 0.0160% | $0 | × | 2.77 | = | $0 |
| $464,970,868 | $475,078,929 | 0.0200% | $0 | × | 2.77 | = | $0 |
| $454,862,805 | $464,970,867 | 0.0240% | $0 | × | 2.77 | = | $0 |
| $444,754,743 | $454,862,804 | 0.0280% | $127,305 | × | 2.77 | = | $353,210 |
| $434,646,681 | $444,754,742 | 0.0320% | $0 | × | 2.77 | = | $0 |
| $424,538,618 | $434,646,680 | 0.0360% | $0 | × | 2.77 | = | $0 |
| $414,430,556 | $424,538,617 | 0.0400% | $0 | × | 2.77 | = | $0 |
| $404,322,494 | $414,430,555 | 0.0440% | $0 | × | 2.77 | = | $0 |
| Less Than | $404,322,493 | 0.0480% | $0 | × | 2.77 | = | $0 |

| 2012 Actual | | 0.0Y% | Bonus Level | | Bonus Rate | | Total Bonus |
|---|---|---|---|---|---|---|---|
| $454,660,373 | × | 0.03% | $127,305 | | 2.77 | = | $353,210 |

| | |
|---|---|
| QMPS - Total Bonus: | $353,210 |
| Number of MDs: | 104 |
| Bonus per MD: | $3,396 |

Figure 45: RADM Measurement Factor

Measurement Factor;

| | | | | | | |
|---|---|---|---|---|---|---|
| Medical Value Index Score: | 64 | Index % | | Bonus Rate Max | | Bonus Rate |
| Score Range: | 80 | 80.4% | X | 5.00 | = | 4.02 |

Figure 46: RADM Bonus Formula

Bonus Formula;

| Total $ | % | | Bonus | | | |
|---|---|---|---|---|---|---|
| 2012 Projection (builds target-actual portion scale) | | | | | | |
| $505,403,117 | | | | | | |

| Scale To Determine Base Portion Amount of Actual (or Target) | | % | | Bonus Level | | Bonus Rate | | Total Bonus |
|---|---|---|---|---|---|---|---|---|
| $505,403,117 | Greater or Equal | 0.0040% | = | $0 | X | 4.02 | = | $0 |
| $495,295,055 | $505,403,116 | 0.0080% | = | $0 | X | 4.02 | = | $0 |
| $485,186,992 | $495,295,054 | 0.0120% | = | $0 | X | 4.02 | = | $0 |
| $475,078,930 | $485,186,991 | 0.0160% | = | $0 | X | 4.02 | = | $0 |
| $464,970,868 | $475,078,929 | 0.0200% | = | $0 | X | 4.02 | = | $0 |
| $454,862,805 | $464,970,867 | 0.0240% | = | $0 | X | 4.02 | = | $0 |
| $444,754,743 | $454,862,804 | 0.0280% | = | $127,305 | X | 4.02 | = | $511,509 |
| $434,646,681 | $444,754,742 | 0.0320% | = | $0 | X | 4.02 | = | $0 |
| $424,538,618 | $434,646,680 | 0.0360% | = | $0 | X | 4.02 | = | $0 |
| $414,430,556 | $424,538,617 | 0.0400% | = | $0 | X | 4.02 | = | $0 |
| $404,322,494 | $414,430,555 | 0.0440% | = | $0 | X | 4.02 | = | $0 |
| Less Than | $404,322,493 | 0.0480% | = | $0 | X | 4.02 | = | $0 |

| 2012 Actual | | 0.0Y% | | Bonus Level | | Bonus Rate | | Total Bonus |
|---|---|---|---|---|---|---|---|---|
| $454,660,373 | X | 0.03% | = | $127,305 | X | 4.02 | = | $511,509 |

RADM - Total Bonus: $511,509
Number of MDs: 104
Bonus per MD: $4,918

Figure 47: MORT Measurement Factor

Measurement Factor;

| | | | | | | | |
|---|---|---|---|---|---|---|---|
| Medical Value Index Score: | 99 | Index % | | Bonus Rate Max | | Bonus Rate | |
| Score Range: | 144 | 68.6% | X | 8.00 | = | 5.49 | |

Figure 48: MORT Bonus Formula

Bonus Formula;

Total $ %
2012 Projection (builds target-actual portion scale)
$505,403,117

| Scale To Determine Base Portion Amount of Actual (or Target) | | | | Bonus | | Bonus Level | | Bonus Rate | | Total Bonus |
|---|---|---|---|---|---|---|---|---|---|---|
| $505,403,117 | Greater or Equal | 0.0040% | | 0.00% | = | $0 | X | 5.49 | = | $0 |
| $495,295,055 | $505,403,116 | 0.0080% | | 0.00% | | $0 | X | 5.49 | = | $0 |
| $485,186,992 | $495,295,054 | 0.0120% | | 0.00% | | $0 | X | 5.49 | = | $0 |
| $475,078,930 | $485,186,991 | 0.0160% | | 0.00% | | $0 | X | 5.49 | = | $0 |
| $464,970,868 | $475,078,929 | 0.0200% | | 0.00% | | $0 | X | 5.49 | = | $0 |
| $454,862,805 | $464,970,867 | 0.0240% | | 0.03% | | $127,305 | X | 5.49 | = | $699,103 |
| $444,754,743 | $454,862,804 | 0.0280% | | 0.00% | | $0 | X | 5.49 | = | $0 |
| $434,646,681 | $444,754,742 | 0.0320% | | 0.00% | | $0 | X | 5.49 | = | $0 |
| $424,538,618 | $434,646,680 | 0.0360% | | 0.00% | | $0 | X | 5.49 | = | $0 |
| $414,430,556 | $424,538,617 | 0.0400% | | 0.00% | | $0 | X | 5.49 | = | $0 |
| $404,322,494 | $414,430,555 | 0.0440% | | 0.00% | | | | | | |
| Less Than | $404,322,493 | 0.0480% | | 0.00% | | | | | | |

| 2012 Actual | | | | | | Bonus Level | | Bonus Rate | | Total Bonus |
|---|---|---|---|---|---|---|---|---|---|---|
| $454,660,373 | X | 0.0Y% | | 0.03% | = | $127,305 | X | 5.49 | = | $699,103 |

MORT - Total Bonus: $699,103
Number of MDs: 104
Bonus per MD: $6,722

Figure 49: MORB Measurement Factor

Measurement Factor;

| | | Index % | | Bonus Rate Max | | Bonus Rate |
|---|---|---|---|---|---|---|
| Medical Value Index Score: | 67 | 38.3% | X | 10.00 | = | 3.83 |
| Score Range: | 174 | | | | | |

Figure 50: MORB Bonus Formula

Bonus Formula;

Total $
2012 Projection (builds target-actual portion scale)
$505,403,117

| Scale To Determine Base Portion Amount of Actual (or Target) | | % | | Bonus Level | | Bonus Rate | | Total Bonus |
|---|---|---|---|---|---|---|---|---|
| $505,403,117 | Greater or Equal | 0.0040% | = | $0 | X | 3.83 | = | $0 |
| $495,295,055 | $505,403,116 | 0.0080% | | $0 | X | 3.83 | = | $0 |
| $485,186,992 | $495,295,054 | 0.0120% | | $0 | X | 3.83 | = | $0 |
| $475,078,930 | $485,186,991 | 0.0160% | | $0 | X | 3.83 | = | $0 |
| $464,970,868 | $475,078,929 | 0.0200% | | $0 | X | 3.83 | = | $0 |
| $454,862,805 | $464,970,867 | 0.0240% | | $0 | X | 3.83 | = | $0 |
| $444,754,743 | $454,862,804 | 0.0280% | | $127,305 | X | 3.83 | = | $488,001 |
| $434,646,681 | $444,754,742 | 0.0320% | | $0 | X | 3.83 | = | $0 |
| $424,538,618 | $434,646,680 | 0.0360% | | $0 | X | 3.83 | = | $0 |
| $414,430,556 | $424,538,617 | 0.0400% | | $0 | X | 3.83 | = | $0 |
| $404,322,494 | $414,430,555 | 0.0440% | | $0 | X | 3.83 | = | $0 |
| Less Than | $404,322,493 | 0.0480% | | $0 | X | 3.83 | = | $0 |

| 2012 Actual | | 0.0Y% | | Bonus Level | | Bonus Rate | | Total Bonus |
|---|---|---|---|---|---|---|---|---|
| $454,660,373 | X | 0.03% | = | $127,305 | | 3.83 | | $488,001 |

MORB - Total Bonus: $488,001
Number of MDs: 29
Bonus per MD: $16,828

Figure 51: RIV Measurement Factor

Measurement Factor;

| | | | | Bonus Rate |
|---|---|---|---|---|
| Medical Value Index Score: | 118 | Index % | Bonus Rate Max | 9.35 |
| Score Range: | 126 | 93.5% × 10.00 = | | |

Figure 52: RIV Bonus Formula

Bonus Formula;

Total $  
2012 Projection (builds target-actual portion scale)  
$505,403,117

| Scale To Determine Base Portion Amount of Actual (or Target) | | % | | Bonus Level | | Bonus Rate | | Total Bonus |
|---|---|---|---|---|---|---|---|---|
| Greater or Equal | $505,403,116 | 0.0040% | = | $0 | × | 9.35 | = | $0 |
| $495,295,055 | $505,403,116 | 0.0080% | | $0 | × | 9.35 | = | $0 |
| $485,186,992 | $495,295,054 | 0.0120% | | $0 | × | 9.35 | = | $0 |
| $475,078,930 | $485,186,991 | 0.0160% | | $0 | × | 9.35 | = | $0 |
| $464,970,868 | $475,078,929 | 0.0200% | | $0 | × | 9.35 | = | $0 |
| $454,862,805 | $464,970,867 | 0.0240% | | $0 | × | 9.35 | = | $0 |
| $444,754,743 | $454,862,804 | 0.0280% | | $127,305 | × | 9.35 | = | $1,190,372 |
| $434,646,681 | $444,754,742 | 0.0320% | | $0 | × | 9.35 | = | $0 |
| $424,538,618 | $434,646,680 | 0.0360% | | $0 | × | 9.35 | = | $0 |
| $414,430,556 | $424,538,617 | 0.0400% | | $0 | × | 9.35 | = | $0 |
| $404,322,494 | $414,430,555 | 0.0440% | | $0 | × | 9.35 | = | $0 |
| Less Than | $404,322,493 | 0.0480% | | $0 | × | 9.35 | = | $0 |

| 2012 Actual | | 0.0Y% | | Bonus Level | | Bonus Rate | | Total Bonus |
|---|---|---|---|---|---|---|---|---|
| $454,660,373 | × | 0.03% | = | $127,305 | × | 9.35 | = | $1,190,372 |

RIV - Total Bonus: $1,190,372  
Number of MDs: 29  
Ave Bonus per MD: $41,047

Figure 53: RESC Measurement Factor

Measurement Factor;

Medical Value Index Score: 169

Figure 54: RESC Bonus Formula

Bonus Formula;

(Computed Through Spending Reduction)

RESC - Total Bonus: NA
Number of MDs: 104
Ave Bonus per MD: NA

Figure 55: Physician Bonus Distribution

Physician Bonuses:

| | Per MD: | | Service Totals: | |
|---|---|---|---|---|
| Service 1 $ = Respiratory | | $72,912 | | $729,116.76 |
| Service 2 $ = Circulatory | | $72,912 | | $364,558.38 |
| Service 3 $ = Neurology | | $72,912 | | $510,381.73 |
| Service 4 $ = Orthopaedics | | $72,912 | | $145,823.35 |
| Service 5 $ = Infections | | $72,912 | | $364,558.38 |
| Service 6 $ = Other Clinical Service Areas | | $15,037 | | $1,127,755.75 |
| Average Base Bonus: | | $63,266 | Total Bonus: | $3,242,194.35 |

Charge To Cost Conversion (same if already cost based):

| | Per MD: | | Service Totals: | |
|---|---|---|---|---|
| Service 1 $ = Respiratory | | $17,498.80 | | $174,988.02 |
| Service 2 $ = Circulatory | | $17,498.80 | | $87,494.01 |
| Service 3 $ = Neurology | | $17,498.80 | | $122,491.62 |
| Service 4 $ = Orthopaedics | | $17,498.80 | | $34,997.60 |
| Service 5 $ = Infections | | $17,498.80 | | $87,494.01 |
| Service 6 $ = Other Clinical Service Areas | | $3,608.82 | | $270,661.38 |
| Average Cost Converted Bonus: | | $15,184 | Total Bonus: | $778,126.64 |

Fixed/Indirect Cost Adjustment:

| | Per MD: | | Service Totals: | |
|---|---|---|---|---|
| Service 1 $ = Respiratory | | $8,094.95 | | $80,949.46 |
| Service 2 $ = Circulatory | | $8,094.95 | | $40,474.73 |
| Service 3 $ = Neurology | | $8,094.95 | | $56,664.62 |
| Service 4 $ = Orthopaedics | | $8,094.95 | | $16,189.89 |
| Service 5 $ = Infections | | $8,094.95 | | $40,474.73 |
| Service 6 $ = Other Clinical Service Areas | | $1,669.44 | | $125,207.95 |
| Average Fix Cost Adjusted Bonus: | | $7,024 | Total Bonus: | $359,961.39 |

Cost Adjusted Average Bonus Per MD: $7,024
Cost Adjusted Total Bonus All MDs: $359,961

Figure 56: Net Savings

| | |
|---|---|
| Calc Flag Setting: | 1 |
| Actual Spending: | $454,660,373 |
| Projected Spending: | $505,403,117 |
| Reduction: | $50,742,744 |
| Charge To Cost Conversion (same if already cost based): | $12,178,258 |
| Fixed/Ind.Cost Adjustment: | $5,633,662 |
| Cost Adjusted Total MD Bonus: | $359,961 (calculated from quality metrics) |
| Cost Adjusted Net Savings: | $5,273,701 |

Figure 57: Hospital and Physician VSHARE Distributions

| H% Selected | P% Selected | Net Savings | Hospital % | Physician % |
|---|---|---|---|---|
| 0% | 0% | 0 - $1.0M | 50% | 50% |
| 0% | 0% | $1.0M - $2.0M | 49% | 51% |
| 0% | 0% | $2.0M - $3.0M | 48% | 52% |
| 0% | 0% | $3.0M - $4.0M | 47% | 53% |
| 0% | 0% | $4.0M - $5.0M | 46% | 54% |
| 45% | 55% | $5.0M - $6.0M | 45% | 55% |
| 0% | 0% | $6.0M - $7.0M | 44% | 56% |
| 0% | 0% | $7.0M - $8.0M | 42% | 58% |
| 45% | 55% | > $8.0M | 40% | 60% |

Net Vshare (Hosp): $2,373,165   45%
Net Vshare (MD): $2,900,536   55%

Figure 58: MD VShare Breakdown

| MD Vshare By Service Area | Savings Portion: | Vshare Potion: | MDs | Vshare Per MD |
|---|---|---|---|---|
| Service 1 $ = Respiratory | 9.88% | $286,434 | 10 | $28,643 |
| Service 2 $ = Circulatory | 4.13% | $119,684 | 5 | $23,937 |
| Service 3 $ = Neurology | 0.56% | $16,285 | 7 | $2,326 |
| Service 4 $ = Orthopaedics | 13.99% | $405,710 | 2 | $202,855 |
| Service 5 $ = Infections | 3.89% | $112,930 | 5 | $22,586 |
| Service 6 $ = Other Clinical Service Areas | 67.56% | $1,959,493 | 75 | $26,127 |
|  | 100.00% | $2,900,536 | 104 | $51,079 |

Figure 59: Total MD Dollars

|  | MDs | Vshare Per MD | + | Bonus Per Md | = | Total $ Per MD |
|---|---|---|---|---|---|---|
| Service 1 $ = Respiratory | 10 | $28,643 |  | $8,095 |  | $36,738 |
| Service 2 $ = Circulatory | 5 | $23,937 |  | $8,095 |  | $32,032 |
| Service 3 $ = Neurology | 7 | $2,326 |  | $8,095 |  | $10,421 |
| Service 4 $ = Orthopaedics | 2 | $202,855 |  | $8,095 |  | $210,950 |
| Service 5 $ = Infections | 5 | $22,586 |  | $8,095 |  | $30,681 |
| Service 6 $ = Other Clinical Service | 75 | $26,127 |  | $1,669 |  | $27,796 |

Figure 60: Yearly Calculation and Summary

| Physician Value Share (Vshare) plus Bonuses: (All dollar amounts in this box are aligned with costs) | | |
|---|---|---|
| 1. Physician portion of Improved financial performance: Actual vs Projected Resource Consumptions for 2012 | Net Vshare: Total All MDs: | $2,900,536 |
| 2. Bonuses for improving Mortality and Morbidity Rates. | Improved Quality Metrics All MDs: | $359,961 |
| | Total All MDs: | $3,260,497 |
| Total MDs: 104 | Avg Per MD: | $31,351 |

| Hospital Value Sharing (Vshare): (All dollar amounts in this box are aligned with costs) | | |
|---|---|---|
| 3. Hospital portion of Improved financial performance: Actual vs Projected Resource Consumptions for 2012 | Net Vshare: Total Hospital: | $2,373,165 |

MEDICAL VALUE INDEX

FIELD OF THE INVENTION

The Medical Value Index "MVI" is designed to objectively and accurately assess the major metrics of value (quality and cost) for inpatient healthcare as well as calculate and distribute financial net saving among providers who are engaged in approved at-risk contracts. A significant percentage of healthcare dollars are expended for hospitalized patients and data availability is sufficient for statistical analyses, which is imperative for quality measurements. Providers use the MVI to document and continuously improve the value they deliver to their patients and the community. The Index is also utilized, by individuals and organizations which pay for healthcare as they strive to move from price-based to value-based healthcare purchasing. The MVI information is presented in an easily interpreted format like the Dow Jones or J D Powers Indices. More importantly it functions as a Rosetta Stone-like translation of medical outcomes that are comprehensible to both the providers and purchasers of healthcare.

BACKGROUND OF THE INVENTION

The present invention relates to technologies, processes and algorithms that quantify medical quality and cost efficiencies for the purpose of creating, financial incentives for rewarding medical providers (hospitals and physicians). The invention uses objectively defined metrics of clinical quality and cost efficiency improvements that are trended over a multi-year period to determine a "Medical Value Index" (MVI). The MVI quantifies the relative quality and cost efficiencies of hospitals and clinical services within the hospitals (orthopedics, cardiology etc.) and determines relative reimbursement rates based on the providers' outcomes. Higher quality and greater efficiencies yield higher reimbursements for the providers. More particularly, the invention's technologies, processes and algorithms transform routinely used, hospital and insurance data into actionable, clinical quality information, which physicians can use to improve the outcomes of their patients' care. The invention's algorithms then aggregate the results of physicians' practice pattern improvements and assign appropriate provider (physician and hospital) and insurer remunerations based on the observed quality and cost efficiency outcomes.

Beginning, in the late 1980's and up to the present, US private and public healthcare purchasers and their insurers have been relying on managed care entities to control widely varying levels of questionable medical quality and escalating healthcare costs. To control costs, these third-party, managed care entities limited patients' access to their chosen physicians and implemented stringent price controls. These measures have been only partially effective. After two decades of managed care controls, the quality and costs of patient care remain uncontrolled and excessive leaving America's entire financial future in question.

Employers can no longer sustain their employees' cost increases and patients are more interested in access to their physicians than in their employers' cost savings. For patients, access to their physicians has come at a significant price because employers have begun to shift their cost burdens back onto the employees. The levels of angst have grown to the point that policy makers and even some employers are now suggesting, in spite of all evidence to the contrary, that a nationalized, single-payer system is the only viable option to control costs by the aligning of financial incentives of all stake-holders (providers, public and private purchasers and their insurers as well as patients). The recently enacted federal Patient Protection and Affordable Care Act (PPACA) was a direct response to uncontrolled, costs but it did not implement a single-payer system. However it did usher in other alternatives that involve global payments to hospitals and physicians such as Accountable Care Organizations (ACO), Acute Care Episodes (ACE) and four Bundled-Payment Models. These new delivery systems allow hospitals and physicians to share net-savings, which hold great promise for improving quality and controlling healthcare costs because physicians can now participate in the savings they helped create through improved clinical outcomes. However, these cost sharing mechanisms will be successful only if quality and efficiencies are accurately assessed and providers are appropriately reimbursed for their efforts. Verras' technologies and techniques are unique in their abilities to assist physicians and hospitals with quality and cost efficiency improvements and to translate the changes in practice patterns to appropriate reimbursements for hospitals and physicians who deliver high quality, cost efficient healthcare.

Patients want their choice of providers at reasonable prices. Public and private purchasers, as well as insurers need to know the value of the services they receive for their money; and providers need the latitude to practice their professions unencumbered by third party intrusions. But these ideals have not materialized for any number of reasons, not the least of which is the misalignment of financial incentives between purchasers, insurers, hospitals and physicians. Currently, for one of these groups to financially win, one or more of the others must lose. The effects of misaligned incentives have created a bizarre triad of: excessive profits for insurance and managed care companies that do not deliver care; insufficient funding, for providers who are dedicated and trained to deliver quality care; and diminished access, coverage and services for patients who need care. Distrust among all parties and chaos in the system are the unintended consequences of misaligned incentives and the inability to contract for healthcare services on the basis of objectively defined value, that is, quality and costs.

For these reasons, the alignment of providers' and hospitals' incentives and their integration into common provider groups are viewed as critical components of the solution to control medical quality and costs. To these ends, numerous care delivery models have been tried but few have met with anything but marginal success. This invention changes this and solves the primary, non-political problems relating the quality and cost issue facing the United States' healthcare system.

There are a few examples in which physicians, hospitals and their insurance entities have aligned their incentives and integrated themselves to achieve reasonable levels of medical quality, and to some extent, cost efficiencies and patient satisfaction. The first example is a health maintenance organization (HMO) model, such as Kaiser Permanente. The second is represented by the Mayo Clinic-type model. Delivery systems of these types can be found in a number of cities throughout the country. What is common to both models is their integration and alignment of quality and financial incentives of the three principal components—physicians, hospitals and insurance entities. Their physicians are generally on salary and receive additional remunerations if the enterprise prospers. However, from a national perspective, these models cannot accommodate the majority of US patients who are treated by independent physicians and hospitals with limited access to integrated provider enterprises, such as these examples.

Another attempt to align providers' incentives and thereby control costs is a program called "pay-for-performance." These initiatives involve the insurer awarding bonuses to physicians for improving a few selected quality indicators. Pay-for-performance has been a largely unsuccessful attempt to achieve what this invention has accomplished, which is the alignment of quality and financial incentives for independent hospitals, physicians and insurers through the novel provisioning of clinical quality improvement and financial information. The key to achieving, the invention's enhanced benefits is transforming the readily available hospital and insurance information into actionable data for physicians to create clinical improvements and aggregating the data into transparent and easily understood measure of quality and efficiencies for the benefit of all stakeholders. The most recent delivery models created by the aforementioned federal legislation (PPACA) make this invention even more valuable than before.

The PPACA legislation implements global budgeting, for hospitals and physicians who will be financially incentivized by Centers for Medicare and Medicaid Services (CMS) for improving the quality and efficiencies of their care. The previously mentioned ACOs, ACEs, and Bundled Payments are three methods as well as other federally designed delivery systems that are dependent on global budgets that will be divided between the hospital and physicians on the basis of objective measures. The technologies, algorithms and quality indices of this invention are uniquely designed to provide the objectively defined, appropriate reimbursements for the hospital and physician providers who are able to create net savings by improving clinical and financial outcomes.

SUMMARY OF THE INVENTION

The invention's technologies, processes and algorithms facilitate an integrated, value-based delivery system across the continuum of care (inpatient and outpatient) in which a healthcare insurer or public agency can financially incentivize providers who will knowledgeably share the net savings between the hospital and physician providers whose practice patterns demonstrate superior performance.

These unique processes utilize risk-adjusted; clinical quality data from hospitals' medical records departments, hospital Medicare specific data, insurers' routinely aggregated claims data, patients' ambulatory outcomes collected by physicians' offices and other examples, but not limited to, National Hospital Quality Measures and Accountable Care Organization Measures. What is pragmatic and synergistic about the invention is its ability to re-purpose the hospitals', physicians' and insurers' routinely used data, which in and of themselves, are not unique. However, the invention's ability to use these same data for four critical functions is unique. First, the invention's processes transform the routinely used data into actionable, clinical quality improvement data that physicians use to improve outcomes. Second, its algorithms quantify the results of physicians' practice pattern enhancements, third, the algorithms assign appropriate provider remunerations based on the quality and cost efficiency outcomes and fourth, the invention converts these data into a Medical Value Index (MVI) that documents a hospital's and medical staff's outcomes over time. For the first time, independent physicians and hospitals will have inpatient, outpatient and insurance data, which can be used to improve clinical, financial and patient centered outcomes while directly linking their quality improvements to appropriate financial rewards. Moreover, employers, patients, public agencies and the providers themselves will have a transparent and accurate measure of the providers' quality and cost efficiencies over time.

The MVI is designed to objectively and accurately assess the major metrics of value (quality and cost) for inpatient healthcare as well as calculate and distribute financial net saving among providers who are engaged in approved at-risk contracts. A significant percentage of healthcare dollars are expended for hospitalized patients and data availability is sufficient for statistical analyses, which is imperative for quality measurements. Providers use the MVI to document and continuously improve the value they deliver to their patients and the community. The Index is also utilized by individuals and organizations which pay for healthcare as they strive to move from price-based to value-based healthcare purchasing. The MVI information is presented in an easily interpreted format like the Dow Jones or J D Powers Indices. More importantly it functions as a Rosetta Stone-like translation of medical outcomes that are comprehensible to both the providers and purchasers of healthcare.

Overview and Metrics of Medical Value Index (MVI)

The MVI has two essential features:

1. Calculating an MVI Based on Quality and Financial Improvements:

The first essential feature is the calculation of hospitals' MVI scores to quantify the enterprises' three-year, trended improvements. This feature records improvements or degradations in quality and financial outcomes (charges or costs) at the clinical service and hospital levels, it is the means by which the easily interpreted MVI graphs are constructed that compare hospitals performances for the benefit of all stakeholders; and 2. Calculating and Distributing Financial Net Savings:

The second essential feature objectively quantifies clinical and financial outcomes improvements and translates them into economic terms. As the marketplace moves from price to value-based healthcare purchasing, the MVI will find greater use as the means of choice for accurately reimbursing providers through the distribution of hospitals' and physicians' net savings, if outcomes have objectively unproved.

The cornerstone of all value propositions is quality, which is a statistical measure. The complex nature of healthcare assessment dictates that several clinical and financial outcomes of providers' performances must be quantified and trended over time to gain a true picture of the value being delivered. Price has no meaning without a measure of the quality of the service or product being purchased. The MVI can be an important adjunct to both sides of the provider-purchaser value equation.

Inpatient Metrics of Quality that Constitute the Medical Value Index (MVI):

M1. Quality Measures and Patient Satisfaction (QMPS):—composite measure of core national measures as reported by hospitals to Center for Medicare and Medicaid Services (CMS), trended for three years or more.
NHQM (National Hospital Quality Measures)
HCAHPS (Patient Satisfactions)

M2. Hospital Readmission Rate (RADM) composite measure of risk-adjusted, 30-day rates as reported by CMS and trended for three years or more.

M3. Mortality Rates (MORT)—nine (9) different hospital mortality metrics, trended for three years or more, including 30-day rates as reported by CMS M4. Morbidity Rates (MORB)—measured for each hospital's top five MS-DRGs within each of the top five clinical services that have the greatest resource intensity (largest numbers of charges or costs) trended for three years or more.

M5. Reductions in Variation (RIV)—top 5 MS-DRGs for the five most resource intense clinical services, trended for three years or more.

M6. Resource Consumption (RESC)—top five clinical services with greatest resource intensity, trended for three years or more.

Inflation rates of Charges or Costs.

Quality Improvements & Financial Improvements and Distributions

M7. (Optional)—three of numerous, potential examples:
ACO 33 Metric (ACOM)—used for those hospitals designated as federal ACOs
American Joint Replacement Registry (AJRR)—use by orthopedic surgeons for patients outcomes assessments.
LeapFrog Measures (LFM)—Healthcare purchaser assessment tool to promote hospital safety and quality.

The current invention incorporates medical knowledge into the processes and algorithms that combine inpatient quality outcomes, ambulatory quality measures and health insurers' financial data into actionable information that hospitals and physicians can use to improve the efficacies and efficiencies of their care. It then quantifies the financial net savings that predictably accrue as a result of the providers' improved medical outcomes. The invention's processes and algorithms also provide the information necessary for the health insurer to equitably share the net saving with the physicians and hospitals as incentives to continuously improve the quality of their patients' care and control costs. In this manner the providers and insurer align their quality and financial incentives and create a virtual integrated delivery system of independent practitioners.

Moreover, this invention facilitates the formation of integrated delivery systems that can be scaled to every community in the nation, which can maximize the health benefits for our entire society.

One advantage of the present invention is the incorporation of clinical decisions, processes and algorithms transform four types of commonly used data into actionable information with which physicians improve clinical quality and cost efficiencies. (Insurers' claims data, hospital medical records data, hospital Medicare-specific quality data and patients self-assessed quality outcomes generated from physicians' offices.)

Another advantage is that clinical decisions and processes determine which clinical specialties to include in the quality improvement initiative and the number of physicians in each.

Yet another advantage of the current invention is that clinical decisions determine which Major Diagnostic Categories (MDC) and Diagnosis Related Groups (DRG) to assign to which of the clinical specialty groups for quality improvement activities.

Another advantage of the current invention is the ability to use clinical decisions to determine case volumes that constitute adequate numbers of patients.

Yet another advantage of the current invention is that clinical and administrative processes determine which patient groups to include in the initiative and calculations by geography, type of insurance plan, etc.

Still another advantage of the present invention uses clinical decisions and administrative processes to determine how many and which DRGs to include in the Reduction in Variation (RIV) computations for financial bonuses.

Another advantage of the current invention is that clinical decisions determine which of the CMS indicators and other clinical indicators are appropriate for quality measurement and remuneration.

Yet another advantage of the current invention is that clinical decisions determine what level of hospital's clinical indicator compliance should be considered as an acceptable quality level for each indicator group.

Still another advantage of the current invention uses algorithms to calculate the net changes in quality indicators, determine the quality bonus factor, apply the results to the sliding, scale and calculate the bonus distribution between physicians and hospital.

Still another advantage of the current invention is that clinical processes are established to determine the improvement percentages that are attributable to the hospital personnel and those to the physicians.

Another advantage of the current invention is that processes determine who and how the "improvements" are to be determined for remuneration (Acceptable Indicators or mortality etc.).

Yet another advantage of the current invention is that insurer's data and administrative processes are used to determine expected inflation rates for Inpatient, Outpatient and Professional components of future expenditures to calculate physicians' bonuses for inpatient care.

Another advantage of the current invention is that it can use insurer's data, actuarial process and algorithms calculate overall Per Member Per Month (PMPM) saving over 16 month periods to determine net saving for value-sharing among insurer, physicians and hospital (for all inpatient, outpatient and ambulatory care).

Still another advantage of the current invention is that clinical decisions and administrative processes designed Excel spreadsheet algorithms that determine bonuses and value-sharing among the three constituents (Physicians, hospitals and insurer).

Still another advantage of the current invention is that Algorithms assess, quantify and summarize the clinical quality and efficiency improvements. Insurer's claims data and the invention's calculations can determine whether bonuses are awarded based on improvements (bonuses dependent on quality being maintained or improved).

Another advantage of the current invention is that clinical and actuarial processes were established to be able to determine "Claims Paid Dollars" and sliding scales of Claims Paid Dollars used by quality metrics. (Quality measures 1, 2 and 7 use sliding scales.)

A further advantage of the current invention is that clinical processes determine "Calculated Net Percentage Change" that constitute "improvement" or declination of quality.

Yet another advantage of the present invention is that clinical processes determine "Clinical Indicators (CI) Net Percentage Change Multiplier" that should be rewarded for "improvement."

Another advantage of the present invention is that clinical, actuarial and administrative processes determine who and how computation of "improvements" will be determined at the end of the year.

Still another advantage of the present invention is that clinical and administrative processes can determine which of the paid dollar categories from the insurer's data should be considered for bonuses (inpatient, outpatient, professional dollars, etc.).

Another advantage of the present invention is that clinical decisions and administrative processes can determine the improvements that are attributable to the hospital personnel and those to the physicians to determine percentage remuneration.

Yet another advantage of the present invention is that clinical processes determine how the decision-support tool arrays data using four quadrant graphs in order to determine reductions in variation of care processes.

Furthermore, another advantage of the current invention is that the clinical and administrative processes determine the technique to be used for measuring weight adjusted dollar averages at year's end.

Yet another advantage of the current invention is that clinical decision and administrative processes determine appropriate "Annual Improvement Percentage" that determines appropriate "Bonus Percentage."

Still another advantage of the current invention is that Algorithms calculate the expected, year-end dollar resource consumptions (expenditures) using hospital's or insurer's inflation rates (Inpatient 8.7%, Outpatient 5.5%, Professional 6.3%).

Another advantage of the current invention is that clinical decisions determined how to measure Reductions In Variation (MAI) of Charges and Length of Stay (LOS) for selected DRGs. Changes in Departmental Variations are measured using a decision-support tool "Sherlock" that arrays the hospitals' medical records data and computes variations.

Yet another advantage of the current invention is the ability of another technology, "Watson", to aggregate specific data from 23 different areas of the hospital i.e. Lab, Pharmacy, X-ray and assign each line item to: the patient on which the resource was applied, the patients with efficient or inefficient outcomes for comparisons, to ordering physician and time the resources were deployed.

Yet another advantage of the current invention is that clinical decisions can determine if or when to include readmission rates in algorithm for remuneration.

Still another advantage of the current invention is that administrative decision processes determine "Bonus Percentage" for each "Level of Individual Participation," that is, physician participation.

Another advantage of the current invention is that clinical, administrative and actuarial processes determine percentage of sharing between insurer, hospital, physicians and Verras.

Yet another advantage of the current invention is that actuarial and clinical processes determine dollars that are available for bonuses and value-sharing using algorithm based on 3 year averages of hospital's data or insurer's paid dollars for each of the clinical specialties that physicians used to improve quality and efficiencies.

Furthermore, another advantage of the present invention is that administrative and actuarial processes determine a method of distributing available dollars if no, or only a portion of value-sharing dollars are available.

Another advantage of the present invention is that administrative processes can determine how start-up costs are covered, by whom and with which dollars.

A further advantage of the current invention is that algorithms determine bonuses for "inpatient" and "facility outpatient care" as well as for value-sharing (net-savings) for total resource utilization, inpatient, facility outpatient, professional fees and ambulatory (office) care.

BRIEF DESCRIPTION OF THE DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 1C represents a graphical analysis of the Medical Value index (MVI) computed using six factors (MVI6);

FIG. 2 represents a tabular analysis of Global Drivers, Case Mix Index Modifier. & Hospital 3 Yr. Average Case Charge used in the analysis of the Medical Value Index (MVI);

FIG. 3 represents a graphical analysis of Quality Measures and Patient Satisfactions (QMPS);

FIG. 4 represents a tabular analysis of a computation summary of Quality Measures and Patient Satisfactions (QMPS);

FIG. 5 represents a tabular analysis of National Hospital Quality Measures (NHQM)—CMS;

FIGS. 6A and 6B represent a tabular analysis of National Hospital Quality Measures (NHQM) specifying the "Measurement Period" data;

FIGS. 7A, 7B and 7C represent a tabular analysis of National Hospital Quality Measures (NHQM) specifying the "Back Period" data;

FIG. 8 represents a graphical analysis of the re-admission rate (RADM);

FIG. 9 represents a tabular analysis of the Composite Re-Admit Rate (RADM)—Computation Summary;

FIG. 10 represents a tabular analysis of the Composite Re-Admit Rate (RADM)—Computation Detail;

FIG. 11 represents a tabular analysis of the Composite Re-Admit Rate (RADM)—"Measurement Period" Data;

FIG. 12 represents a tabular analysis of the Composite Re-Admit Rate (RADM)—"Back Period" Data;

FIG. 13 represents a graphical analysis of the Risk Adjusted Mortality Rate (MORT);

FIG. 14 represents a tabular analysis of the Risk Adjusted Mortality (MORT)—Computation Summary;

FIG. 15 represents a tabular analysis of the Risk Adjusted Mortality Rate (MORT)—Computation Detail Data;

FIG. 16 represents a tabular analysis of the Risk Adjusted Mortality Rate (MORT)—"Measurement Period" Data;

FIG. 17 represents a tabular analysis of the Risk Adjusted Mortality Rate (MORT)—"Back Period" Data;

FIG. 18 represents a graphical analysis of the Risk Adjusted Morbidity Rate (MORB);

FIG. 19 represents a tabular analysis of the Risk Adjusted Morbidity Rate (MORB)—Computation Summary;

FIG. 20 represents a tabular analysis of the Risk Adjusted Morbidity Rate (MORB)—Computation Detail;

FIG. 21 represents a tabular analysis of the Risk Adjusted Morbidity Rate (MORB)—"Measurement Period" Data;

FIG. 22 represents a tabular analysis of the Risk Adjusted Morbidity Rate—"Back Period" Data;

FIG. 23 represents a graphical analysis of the Reduction in Variation (RIV);

FIG. 24 represents a graphical analysis of Reduction In Variation (RIV)—3-Year Trending Model;

FIG. 25 represents a tabular analysis of the Reduction in Variation (RIV)—Computation Summary;

FIGS. 26A and 26B represent a tabular analysis of the Reduction In Variation (RIV)—Computation Detail;

FIGS. 27A and 27B represents a tabular analysis of the Reduction in Variation (RIV)—"Measurement Period" Data;

FIGS. 28A and 28B represents a tabular analysis of the Reduction In Variation (RIV)—"Back Period" Data;

FIG. 29 represents a graphical analysis of the Resource Consumption (RESC);

FIG. 30 represents a tabular analysis of the Resource Consumption (RES)—Computation Summary;

FIG. 31 represents a tabular analysis of the Recourse Consumption (RES)—Computation Detail;

FIG. 32 represents a tabular analysis of the Resource Consumption (RES)—"Measurement Period" Data;

FIG. 33 represents a tabular analysis of the Resource Consumption (RES)—"Back Period" Data;

FIG. 34 represents a graphical analysis of the Charge (or Cost) Projection;

FIG. 35 represents a tabular analysis of the Back Year Dollars Per-Case;

FIG. 36 represents a tabular analysis of the Projection from historical percent change;

FIG. 37 represents a tabular analysis of the Target from Percent Change Goal;

FIG. 38 represents a tabular analysis of the Actual Results of Measurement Period;

FIG. 39 represents a tabular analysis of the Gross Savings;

FIG. 40 represents a tabular analysis of the Cost Ratios;

FIG. 41 represents a tabular analysis of The Physicians;

FIG. 42 represents a tabular analysis of The Physician Bonus By Quality Metric;

FIG. 43 represents a tabular analysis of the Quality Measures and Patient Satisfaction (QMPS) Measurement Factor;

FIG. 44 represents a tabular analysis of the QMPS Bonus Formula;

FIG. 45 represents a tabular analysis of the Composite Re-Admit Rate (RADM) Measurement Factor;

FIG. 46 represents a tabular analysis of the RADM Bonus Formula;

FIG. 47 represents a tabular analysis of the Risk Adjusted Mortality (MORT) Measurement Factor;

FIG. 48 represents a tabular analysis of the MORT Bonus Formula;

FIG. 49 represents a tabular analysis of the Risk Adjusted Morbidity Rate (MORB) Measurement Factor;

FIG. 50 represents a tabular analysis of the MORB Bonus Formula;

FIG. 51 represents a tabular analysis of the Reduction in Variation (RIV) Measurement Factor;

FIG. 52 represents a tabular analysis of the RIV Bonus Formula;

FIG. 53 represents a tabular analysis of the RESC Measurement Factor;

FIG. 54 represents a tabular analysis of the RESC Bonus Formula;

FIG. 55 represents a tabular analysis of the Physician Bonus Distribution;

FIG. 56 represents a tabular analysis of the Net Savings;

FIG. 57 represents a tabular analysis of the Hospital and Physician VSHARE Distributions;

FIG. 58 represents a tabular analysis of the MD VShare Breakdown;

FIG. 59 represents a tabular analysis of the MD VShare Breakdown;

FIG. 60 represents a tabular analysis of the Yearly Calculation and Summary.

DETAILED DESCRIPTION OF THE PREFERRED EMBODIMENT

The accompanying drawings, which are incorporated in and form a part of this specification, illustrate embodiments of the invention and together with the description, serve to explain the principals of this invention.

Figure 1A:
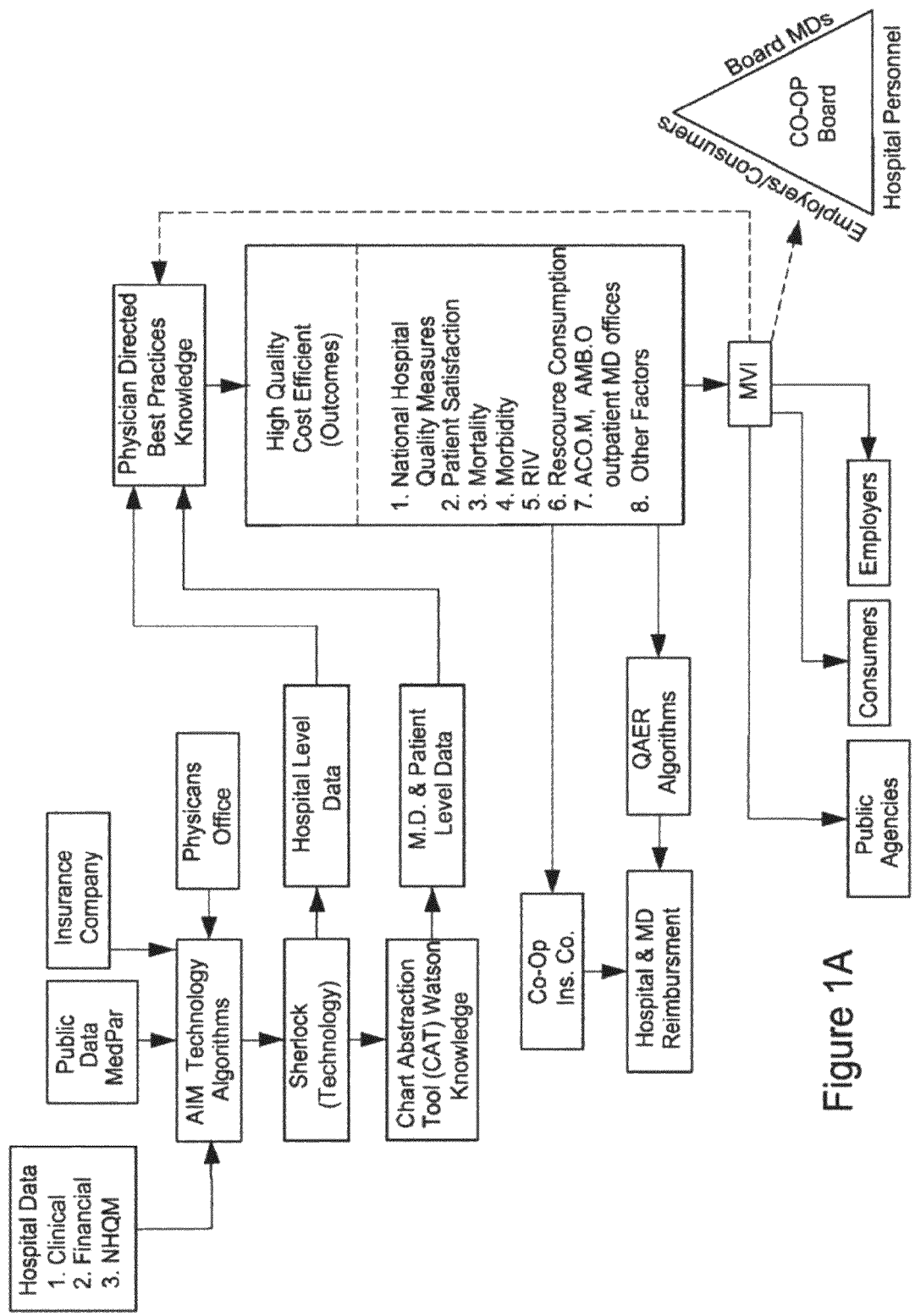
FIG. 1A depicts a flow chart indicating the flow of use of and dissemination of hospital data, physician's office data, public (MedPar) data and data from insurance companies.

Referring now to the drawings, wherein similar parts are identified by like reference numerals, FIG. 1A shows a flow chart of data leading to the calculation of a Medical Value Index (MVI) also known previously as an Index of Quality Improvement (IQI), but from here forth simply referred to as MVI, and the pathways of use of that MVI. Data is originally sourced from hospital records, public data like MedPar, insurance companies and physician's offices. The data is fed to AIM technology algorithms and sent to Sherlock for conversion into hospital level data. Data from Sherlock also is sent to a Chart Abstraction Tool (CAT) and Watson knowledge system for transference into MD and patient level data. Both hospital level data and MD and patient level data are sent to a physician directed best practices knowledge base, and used in metric calculations. High quality efficiency outcomes lead to 6 or more metrics available for use in calculating an MVI. In FIG. 1A, 7 metrics are shown: 1. National Hospital Quality Measures (NHQM); 2. Patient Satisfaction; 3. Mortality; 4. Morbidity; 5. Reductions in Variation (RIV); 6. Resource consumption; and 7. Accountable Care Measures (ACO.M), ambulatory outcomes (AMB.O) from outpatient MD offices. A more typical arrangement of metrics is to combine metrics 1 and 2 into a compound metric 1 called Quality Measures & Patient Satisfaction (QMPS). Furthermore, a new metric titled Re-Admission (RADM) is installed as metric 2. One or more additional factors, represented by metric 8 can also be used in the calculation of MVI. The metrics within the MVI are modular and may be tailored to fit the audience. Once an MVI is determined, it is sent to public agencies, consumer, employers and optionally CO-Ops, and optionally may be sent back to the physician directed best practices knowledge base. CO-Ops may use the MVI information through their CO-Op Board and disseminated to employers/consumers, board MDs and hospital personnel. Therefore, as illustrated in FIG. 1A the present invention is a system for healthcare performance measurement and equitable provider reimbursement comprising, the elements of: (a) gather medical information from hospital patients charts data, hospital medical records department data, insurance company data, and physician's office data; (b) aggregate the gathered data and calculating the following quality metrics: National Hospital Quality Measures (NHQM) and patient satisfaction mandated by Centers for Medicare and Medicaid Services (CMS), morbidity, mortality, reduction in variation, resource consumption; (c) calculate a Medical Value index (MVI) for each healthcare provider; (d) generate value sharing computations and calculate overall net savings, and (e) distribute said net savings to physicians, hospitals, CO-OPs and insurers in the form of reimbursements.

Figure 1B:
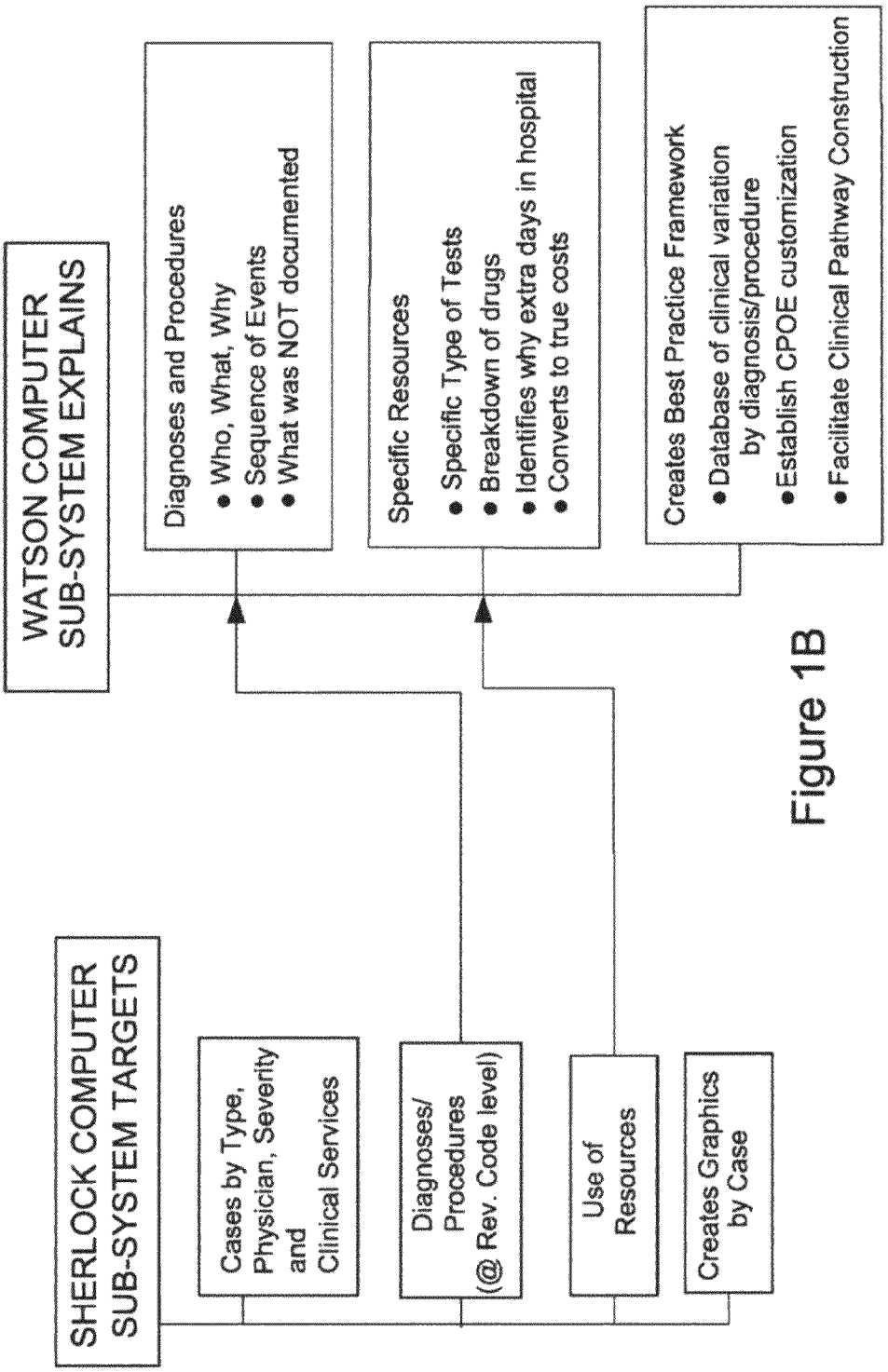
FIG. 1B illustrates the relationship between the Sherlock computational model and the Watson analytic model, and the flow of information between the two systems.

FIG. 1B illustrates the characteristics of and relationships between Sherlock and Watson, and in particular is illustrates the data flow between the two systems. AIM technology algorithms (as seen in FIG. 1A) are employed to aggregate data gathered from medical information from hospital patients charts data, hospital medical records department data, insurance company data, and physician's office data, prior to providing the resulting information to a. Sherlock sub-system. The Sherlock sub-system arranges the data for full drill-down analysis, allowing, inspection down to the lowest element in a hierarchical arrangement. Sherlock sub-system aggregated data is further analyzed by a Watson sub-system which explains diagnoses and procedures by who, what and why, sequence of events and what was not documented, explains specific resources by specific type of tests, breakdown of drugs, identifies why extra days were spent in hospital, and converts to true costs, and create a best practices framework by database of clinical variation by diagnosis and procedure, establishes a computerized physician order entry (CPOE) customization and facilitates clinical pathway construction. At the revenue code level—every billed item in a hospital has a revenue code. For example a Chest X-ray is 320. Sherlock has the capability of telling us that during a specific hospital stay, there were 10 chest rays using these codes. However, the revenue code level cannot tell you the specific type of chest X-ray nor when it was ordered and who ordered it. The Watson sub system provides an alternate and deeper analysis to the data clues provided by the Sherlock sub-system Watson's Chart Audit tools use the Revenue Codes and other data targeted by Sherlock to discover the basis of why, who, when these order were written. CPOE is short for Computerized. Physician Order Entry. Now that all hospitals are moving toward the Electronic Health Record (EHR or EMR), a physician must bring up a screen and decide what orders are required rather than just pull the chart and write them out. In order to expedite this process, templates are built by diagnosis to list the most appropriate or likely test based on diagnosis. Watson will use a physician's actual order history, pull out their best practices and customize these templates. The value here is that by customizing (shortening) this list it improves compliance with the CPOE and hopefully stops the physician from over-ordering.

FIG. 1C depicts in graphical form the calculation of a Medical Value Index (MVI) using six metrics. The six metrics are (1) Quality Measures and Patient Satisfaction (QMPS), (2) Re-Admission Rate Score (RADM); (3) Mortality index (MORT), (4) Morbidity index (MORB), (5) Reductions in Variation (RIV); and (6) Resource Consumption (RESC). When these metrics are added up in FIG. 1C, as shown, the MVI is 559 for the example demo hospital medical center.

Interpretation of MVI:

The Medical Value Index, has been developed in order to presents multiple quality and efficiency improvement outcomes in a transparent and easily understood manner. Each hospital's outcomes metrics are depicted by a single bar graph—the higher the bar, the greater the three-year hospital improvements and the greater the value of the medical organization's outcomes, as seen here in FIG. 1C. Hospitals' clinical services can individually be displayed in a similar manner. Hospitals and physicians have historically used one or more of these industry-standard metrics on an individual basis to measure their quality and cost efficiency outcomes. They are generally part of a regulatory report or for marketing themselves to local employers and self-pay patients. Public and private purchasers can also use the MVI as an excellent means of comparing efficacies and efficiencies of regional hospitals.

To simplify the interpretations of individual Mill metrics, each of the component bars are stacked to create a single MVI bar graph representing a hospital's Total MVI Score (See FIG. 1C). Moreover, the total score can be calculated to represent a single facility or the average of multiple facilities. (Example below—a Single Hospital's (DHMC) Bar Graph on Left has an MVI score of 559/800. The Regional Norm of multiple hospitals' averages on the Right has scores of 510/800). The height of each clinical component indicates the relative contribution to the overall score and the degree to which the indicator was improved or degraded over three years or more. The 6 metric MVI utilizes an 800-point scoring method, while the optional 7 metric MVI uses a 1000-point total. The component measures have different weighting factors based on experiential evidence as to which metrics are the most predictive of actual clinical quality and cost efficiency improvements.

Verras' technologies and techniques aggregate the measures and trend multiple clinical quality and efficiency outcomes to statistically determine if there have been improvements, degradations or static outcomes over at least a 3-year period. The six or seventh (optional) outcome changes are computed separately using the Verras MVI algorithm to determine the "score" for each of the outcomes. Each outcome's metric score is compared to the empirically derived maximum score and recorded as a percentage. As shown below in FIG. 1C, the measures are then stacked one on top of another for a visual MVI, which is an index of value for each hospital as well as down to clinical service levels (orthopedics, cardiology etc.) "The higher the bar, the greater the value of the hospital's outcomes". In this regard it is like the Dow Jones or J. D. a Powers indices, which are also easily interpreted means for business and investors to evaluate whether companies' products and business metrics are improving or degrading.

Unique and Critical Functions of the MVI:
  A. Objectively Documents All Major Metrics of Hospitals' Quality and Cost Efficiency Improvements (Value) over Three or More Years.
  B. Objectively and Transparently Quantities Hospital's and Medical Staff's Outcomes in Order for Healthcare Purchasers and Patients to Compare Hospitals' Outcomes and Transition from Contracting on Price to Value-Based Healthcare Purchasing,
  C. Prospectively Determines the Financial Rewards for Each Hospital, Based on the Clinical and Financial Outcomes of a Multiple Hospital Accountable Care Organization (ACO).
  D. Prospectively Determines the Appropriate Financial Distribution Between a Hospital and Its Medical Staff that Participate in an At-Risk, Value-Based Payment Model.
  E. Quantifies Inpatient Quality and Efficiency Outcomes of Individual Clinical Services (Cardiology, Orthopedics, and Hospitalists) in Order to Differentially Reimburse the Hospital and Its Physicians Who Are At-Risk Under Medicare or Other Value-Based Payment Models.

Data Sources and Time Periods Utilized for Calculating the MVI:

The computations for each of the component measures of the Medical Value Index are similar in that they are aggregated and the data are compared for single or multiple hospitals over a period of three or more-years.

MVI is created using a rolling three or more years assessment to maximize accuracy. Most data inputs are from hospitals' medical records data (Uniform Hospital Discharge Data Set 'UHDDS'). Additional data inputs from NHQM (including re-admission rates and mortality rates) and HCAHPS are, for the most part, manually abstracted by hospital personnel and processed by third party vendors as mandated by the federal government. Some measures, such as 30-day mortality and 30-day re-admission rates are calculated directly by CMS and made available publically. The UHDDS and NHQM and HCAPS data records may be pulled from government repositories, such as the CMS MedPAR and Hospital Compare databases representing acute care for the Medicare population, or directly from hospital database systems and staff. Verras commonly accesses these federal and hospital specific data sources as inputs for the MVI. The outcomes will be discussed with each of the measures.

At the beginning of a hospital initiative, or when calculating a multiple hospital MVI using Medicare (MedPAR Data), four or more years of data are acquired from the hospital or from the Medicare Provider Analysis and Review (MedPAR). They are labeled by years from newest to oldest as Measurement Period, Back 1, Back 2, Back 3, Back n, Periods. The "Measurement Period" moves ahead with each passing year, as do the "Back. Periods". Thus to measure the subsequent year, the "Measurement Period" is assigned to the new year, the previous "Measurement Period" is now assigned to the Back 1 Period, the previous Back 2 Period is now assigned to the Back 2 Period, and so on.

As an adjunct to measuring (indexing) the quality and cost efficiencies of a facility, one may determine a net savings that is a result of quality improvement as measured by MVI for the purpose of distributing the dollars between clinical and administrative entities responsible for the changes. In order to prognosticate a net savings that can be shared among the hospital and physicians, it is necessary to Project the subsequent years resource consumption in charges (or costs) as the expected number of resources that will be consumed, based on the previous 4 or more years' trended financial outcomes.

At the conclusion of the "Measurement Period" and the data becomes available from the respective technology systems, the "Measurement Period" data is entered into the MVI as what "Actually" has transpired in comparison to the outcomes that were projected. At the beginning of the Measurement Period, the providers determine "Target" outcomes they will endeavor to achieve over the ensuing; 12 months. At the end of the twelve months Measurement Period, the differences between the "Actual" measurement data and the Projections become the "Net Savings" or "Net Losses". Improvements in other metrics such as, QMPS, RADM, MORB, MORT, and RIV may also be prognosticated to demonstrate the expected outcomes of the physicians' improvements. Time Periods, listed in Table 1 below, provide further examples of the typical data periods and how they align to the MVI and Net Savings use cases:

TABLE 1

Example Data Periods

| | |
|---|---|
| Measurement Period | 2012 (Most current period in Calculation, the focus of analysis)* |
| Back 1 | 2011 |
| Back 2 | 2010 Minimum Oldest Period for MVI |
| Back 3 | 2009 Minimum Oldest Period for Financial Projection |

*Note, the "Measurement Period" is unique in that it is the annual interval of attention for a given calculation run. In the planning stages for prognosticating the outcomes of the "Measurement Period", before all the data for the "Measurement Period" is available, the provider enterprise can Project the data and Target a goal for this period, as is often done for the financial trend analysis. The "Measurement Period" represents the Actual and final calculation for that period once all the data is received from the data sources and processed for that time frame.

MVI Positive Score System:

The empirical values for the six component metrics and total score (800 points) are based on years of experiential observations as to the accuracy of each metric in predicting clinical and operational quality of care. As an example, QMPS has the lowest maximum score (46 points) because it is the least predictive, while RESC has the highest maximum score (230 points) because it has both robust financial as well as quality implications.

The following quality and financial indicators demonstrate improvements when their rates are smaller as expressed by negative numbers: Re-Admission (RADM) and Mortality (MORT) and Morbidity (MORB) rates, Reductions In Variation (RIV) and Resource Consumption 'charges or costs' (RESC). Sin order to create a MVI bar that is positive (higher) with improving quality and efficiencies, the direction of improvement is inverted either directly or through sliding scales. Conversely. NHQM and HCAHPS improvements are positive numbers; therefore no conversions from negative to positive scores are necessary.

Global Drivers and Common Patient Cohorts for MVI Assessments:

A set, of common computations are performed and made available for use by the metrics in varying combinations. Two global drivers are used as modifiers to the various quality and cost efficiency calculations: A. Case Mix Index (CMI) and B. Each Hospital's Actual Charges. These two drivers are discussed as follows:

Case Mix Index (CMI):

The first driver is each hospital's reported, average three-year Case Mix Index. In order to compare hospitals' outcomes in any geographic area, it is necessary to take into consideration the complexity of each hospital's patients' conditions. Each hospital's Case Mix Index is an acceptable means of accomplishing such comparisons. This insures that the tertiary and quaternary services in such hospitals are taken into consideration when being compared to hospitals without such intense services. For each of the relevant scores, ten percent (10%) are attributed to the hospital's CMI. The 10% is an empirically derived amount based on years of Observing hospital data. (Note below, the hospital (DHMC) that is used for these examples has a CMI of 1.6827 as determined by the federal governments' formula.

The CMI component is determined specific to the maximum sub score of a given metric. The computation is as follows. First determine 10% of the max score for the given metric, this will be the max of the associated CMI component. Next determine the maximum possible value of the three-year average CMI scores for all in-patient hospitals across the United States in relation to the "Measurement Period" and "Back Period" years. Next, determine the three-year average CMI of the target hospital in relation to the measurement and "Back Period" year periods of the other hospitals. Finally take these three determined values and calculate the CMI Component Score using the following formula.

CMI Component Score=([10% of Metric Max]/[3-Year CMI Max of all Hospitals])×[3-Year Average CMI of Target Hospital]

Hospitals' Actual, Three-Year Average Charges:

The second global driver involves each hospital's actual, three-year, average of charges Per-Case. Even when costs are the central focus in other areas of the MVI, this measure specifically targets a hospital's charges. When computing inflation rates and then comparing hospitals one to another in a given region, it is important for healthcare purchasers and also to providers to have some rough idea as to the relative prices being charged for medical service rendered.

Even as inexact as such a science might be, employers and other healthcare purchasers especially interested to know these relative prices among hospitals. For example, two hospitals in a city may have identical price inflation rates over a three or more year period, but if one hospital charges 20% or even 50% more than the other, purchasers want to know it. They also want to be assured these price differences have been taken into account in a system such as MVI.

FIG. 2, Global Drivers, Interpretations:
1. On the top left side of FIG. 2 is placed the hospital's Average CMI. It is used in the appropriate measures as recorded in the "CMI. Modifier to Apply" box on right,
2. The lower portion of FIG. 2 is the hospitals' average three-year Case Charges. The charge amount is converted by the inverse sliding scale to the modifier and recorded in the "Charge Modifier to Apply" box on right. Note the inverse ratio of the "Charge Modifier to Apply" to METRIC 6—Resource Consumption—the lower the hospitals charge, the larger the additive charge modifier. A higher modifier is a component of the MVI for Resource Consumption (RESC), indicating a more favorable charge structure and higher value for customers.

Top Five Clinical Service Areas:

These are the top most resource intensive service areas as defined by those Major Diagnostic Categories (MDCs) with the highest total charges (or costs) across both the "Measurement Period" and the Back Periods. Each hospitals list may be different but the typical areas are Pulmonary (MDC 4), Cardiology (MDC 5), Neurology (MDC 1), Orthopedics (MDC 8), and infections Disease (MDC 18). This driver is a starting point for Mortality. Reduction-In-Variation and Resource Consumption Calculations.

Top Ten Diagnosis Related Groups (DRG):

These are the top most resource intensive diagnosis groups as defined those MS-DRGs with the highest total charges (or costs) across both the "Measurement Period" and the Back Periods. Each patient's discharge record is grouped to a single DRG for reporting and payment purposes. The primary DRG system in use is the Medicare Severity-Diagnosis Related Groups (MS-DRGs) defined by CMS. This driver is a starting point for Morbidity Calculations.

Top MS-DRGs for Each Top Clinical Service Area:

These are the top most resource intensive diagnosis groups for each of the top most resource intensive service areas. This is defined as the Top 5 MS-DRGs within each of the Top 5 MDCs with the highest total charges (or costs). This driver is primary for Reduction-In-Variation Calculations.

II. Calculating MVI Scores to Quantify Hospitals' Trended Quality Improvements

All calculations of MVI scores are performed at the Major Diagnostic Category (MDC) and Diagnosis Related Group (DRG) levels. This allows clinicians of multiple clinical disciplines to enhance their patients' outcomes by reasoning together to reduce variations in clinical practices and thereby create improvements in quality and cost efficiencies as well as improve their hospital's MVI. (In selected circumstances it may be possible to calculate the scores at the individual physician level, but the example used here will be done at the clinical service levels. Calculating, exact resource consumptions by physician requires the hospital to have four years of fully allocated cost data plus the means to assign each test or treatment to the appropriate ordering physicians using. Computerized Physician Order Entry (CPOE).

The rest of this section elucidates the computation details of each MVI component metric. This information is presented in the following format to act as guides and recurring references. In many instances the information will be repeated to support non-sequential reading.

TABLE 2

Format for Discussing Each of the Six Component Measures:

TITLE: Name and Characteristics
DESCRIPTION: General definition of the Metric and data sources
COMPUTATION SUMMARY: Overview description of the measures calculations
COMPUTATION DETAILS: Full discussion of calculation steps
MEASUREMENT PERIOD DATA: Specifics of the Measurement Period's source data concerning the most recent 12 month period in the Target Data, period range.
BACK PERIOD DATA: Specifics of the Measurement Period's Back Data - the data concerning the period older than the "Measurement Period" in the Target Data, period range.

QMPS Measure Definition

Metric 1

TITLE: Quality Measures & Patient Satisfactions (QMPS)

Score Range: 0 to 46 points (calculated score for this hospital shown as 43 out of 46)

Graphing Color: Medium Blue

Graphing Position: First Position, Left Most of Horizontal Bars and Bottom of Stack Type of Measure: Bundle of Core National Process of Care Measures Score Modified by CMI: No Score Modified by Average Per-Case Charge: No See FIG. 3.

Description:

QMPS is a composite measure of National Hospital Quality Measures (NHQM) and Hospital Consumer Assessment of HealthCare Providers and Systems (HCAHPS). The two data sets are provided by each hospital and both reported by the hospital to the Center for Medicare and Medicaid Services (CMS).

There are 24 NHQM and 10 HCAHPS assessments included in the MVI at this time, as shown below in Table 3 below. The number of measures used in this composite measure may change over time as CMS retires measures or adds new measures required for full reimbursement under the Prospective Payment System (PPS),

TABLE 3

Select National Quality Measures and Patient Satisfaction (QMPS)

| Acute Myocardial Infarction (AMI) - Improvement Is Rate Increase | |
|---|---|
| AMI-1: | Aspirin at Arrival |
| AMI-2: | Aspirin Prescribed at Discharge |
| AMI-3: | ACEI or ARB for LVSD |
| AMI-4: | Adult Smoking Cessation Advice/Counseling |
| AMI-5: | Beta Blocker Prescribed at Discharge |
| AMI-7a: | Fibrinolytic Therapy Received within 30 Minutes of Hospital Arrival |
| AMI-8a: | Primary PCI Received within 90 Minutes of Hospital Arrival |
| Heart Failure (HF) - Improvement Is Rate increase | |
| HF-1: | Discharge Instructions |
| HF-2: | Evaluation of LVS Function |

TABLE 3-continued

Select National Quality Measures and Patient Satisfaction (QMPS)

| | |
|---|---|
| HF-3: | ACEI or ARB for LVSD |
| HF-4: | Adult Smoking Cessation Advice/Counseling |

Pneumonia (PN) - Improvement Is Rate Increase

| | |
|---|---|
| PN-2: | Pneumococcal Vaccination |
| PN-3b: | Blood Cultures Performed in the ER Prior to Initial Antibiotic Received in Hospital |
| PN-4: | Adult Smoking Cessation Advice/Counseling |
| PN-5c: | Initial Antibiotic Received Within 6 Hours of Hospital Arrival |
| PN-6: | Initial Antibiotic Selection for CAP in Immunocompetent Patient |

Surgical Care Improvement Project (SCIP) - Improvement Is Rate Increase

| | |
|---|---|
| SCIP-Inf-1a: | Prophylactic Antibiotic Received within One Hour to Surgical Incision |
| SCIP-Inf-2a: | Prophylactic Antibiotic Selection for Surgical Patients |
| SCIP-Inf-3a: | Prophylactic Antibiotics Discontinued within 24 Hours After Surgery End Time |
| SCIP-Inf-4: | Cardiac Patients with controlled 6 am, Postoperative Blood Glucose |
| SCIP-Inf-6: | Surgery Patients with Appropriate Hair Removal |
| SCIP-Card-2: | Surgery Patients on Beta Blocker Therapy Prior Arrival & Periop |
| SCIP-VTE-1: | Surgery Patients with Venous Thromboembolism Prophylaxis |
| SCIP-VTE-2: | Surgery Patients with Venous Thromboembolism Prophy in 24 hrs |

Patient Satisfaction - Improvement Is Rate Increase

| | |
|---|---|
| PS-1: | Admission Overall |
| PS-2: | Room Overall |
| PS-3: | Meals Overall |
| PS-4: | Nurses Overall |
| PS-5: | Test & Treatments |
| PS-6: | Visitors & Family |
| PS-7: | Physician |
| PS-8: | Discharge |
| PS-9: | Personal Issues |
| PS-10: | Overall Assessment |

The calculations will be discussed only for NHQM (not HCAHPS) as they are similar.

Data Sources:

Values for each of these measures are gathered from either the CMS Hospital Compare database or directly from the hospital. Designated 3rd party vendors manage the calculations of these values for each of the individual measures in the bundle. The technical definitions of the individual measures are strictly controlled by CMS so that the calculations are consistent. There are specifications manuals published biannually and jointly by CMS and The Joint Commission that define the detailed algorithms behind the measures. Third-party vendors are tested and verified to be able to calculate the measure in perfect alignment with the active specification manuals.

Verras has used its 30 years of experience to create the novel ability to aggregate and trend data such as NHQMs and HCAHPS outcomes over 3 years and determine if there have been improvements, degradations or status quo outcomes during the 3-year period. The Verras MVI algorithm maps the overall rate of the measures bundled together in QMPS to determine the "score", which is a percentage of the total possible points allocated to the QMPS (46). There is no modification by the hospital's CMI or average Per-Case charge for this measure. In the illustrated example used here, the hospital's QMPS component score is 92% or 43 points of 46 total.

Computation Summary:

Metric 1 (QMPS) is calculated from the overall mean rate of the collection of measures and translating the rate into the score range assigned to QMPS—0 to 46. The resulting translation becomes the MVI 1 QMPS component score. See FIG. 4, in this example the overall mean rate of 92.48% translates to a component score of 43.

Computation Details:

Metric 1 (QMPS), computation begins with the gathering of 3 or more years of data from the intended data sources; either directly from the hospital or from a public source such as the CMS Hospital Compare database. The most recent year of the data period gathered is the "Measurement Period" while the prior years are denoted the "Back Years". In the current example, the "Measurement Period" is for calendar year 2012 and the Base Period is for 2011, 2010, and 2009. The key source data elements to be gathered are the numerator and denominator case counts for each sub-measure in the collection for each reporting period within the full data period range. Often the reporting periods for these sub-measures are in quarters of a year so they are aggregated up as needed.

The computation that drives the QMPS score is the Overall Mean Rate %, which is the mean of all rates across the collection of measures across all years in the data period range. In the current example this is the Overall Mean Rate of 42.46% rounded to 43%. This mean rate is then translated into the official score for the MVI QMPS component using the following formula:

(QMPS Component Score [43])=(Overall Mean Rate [92.48%])×[QMPS Max Score=46]) rounded to nearest integer.

Additional computations are performed and done in stages of comparison between the "Measurement Period" and the "Back Period". The first level of analysis begins with the aggregations of the "Back Period" data separate from the "Measurement Period" data. This involves determining the mean rate of the measures in the "Back Period" and then the mean rate of the measures in the "Measurement Period."

The additional calculations to help with analysis include the computation of the change in mean rate (Delta) and which measures have improved (Imp), remained unchanged (Unc), or degraded (Deg) when comparing the "Measurement Period" to the "Back Years". The calculations of these data Delta, Imp/Unc, Deg, are not figured into the calculations of the score but simply an aid for quality improvement purposes. For example in FIG. 3 below, if the Delta % is positive (second column below), then improvements have been made. If the Delta % is negative, as with "AM1-1 Aspirin at Arrival", then degradation in performance has occurred. FIG. 5 illustrates these computations along with the detailed steps that follow.

Note as one example, AM1-1 Aspirin on Arrival: the Mean Comparison is 99.2% (orange, left column) and the Delta is a −0.4% because there are degradation of outcomes from 99.4% in the "Back Period" (dark green, 2011 and 2010) to 99.0%"Measurement Period" (dark blue, 2012).

Step 1. Gather the NHQM and HCAPS Rates and associated numerator case count and denominator case count for each of the selected NHQM and HCAPS sub-measures for both the "Measurement Period" and the "Back. Period". The resulting rates are calculated by gathering the numerator and denominator counts.

(Step 2. (Optional) Calculate the Delta Rate and Imp/Unc Flag and Deg Flag for each of the selected NHQM and HCAPS sub-measures for both the "Measurement Period" and the Back Period. These are calculated as an investigative aid for quality improvement purposes used by hospital personnel and MDs.

Step 3. Calculate the Overall Mean Rate % by determining mean of all rates across the collection of sub-measures across all years in the full data period range.

Step 4. Calculate the MVI Component Score for QMPS. Using the Overall Mean Rate calculated in the prior step, calculate the score as a percentage of the max.

(QMPS Component Score [43])=(Overall Mean Rate [92.48%])×[QMPS Max Score=46]) rounded to nearest integer.

The QMPS Component Score is also known as the MVI Metric #1 Score, which is that used in the graphs as the official score for quality measures and patient satisfaction for the measurement period.

Measurement Period Data:

The "Measurement Period" is the most current 12-month period in the full data period range. The reporting period of the source data for Metric 1 (QMPS) is typically a quarter. For transparency and traceability purposes, data is normally stored in its original quarterly form and aggregated together as needed to support the overall computations. Thus with QMPS, the "Measurement period" data consists of four quarters of numerator and denominator data for each measure. See FIG. 6.

Note, when a given sub-measure defined in the collection is not applicable for the hospital being measured, such as a hospital has waived the need to calculate the sub-measure, the sub-measure is excluded from the calculation in a way to not adversely affect the hospitals MVI Score.

Back Period Data:

The "Back Period" data is the range of data that chronologically comes before the "Measurement period" in the full data period range, which is 3 or more years. As mentioned with the "Measurement Period" data, the reporting period of the source data for Metric 1 (QMPS) is typically a quarter. For transparency and traceability, data is normally stored in its original quarterly form and aggregated together as needed to support the overall computations. Thus with QMPS, the "Back Period" data consists of eight or more quarters of numerator and denominator data for each measure. See FIG. 7.

Note, when a given measure element is not applicable for the hospital being measured, such as a measure the hospital may have waived their need to support, the measure is excluded from the calculation in a way to not adversely affect the hospitals MVI Score.

RADM Measure Definition

Metric 2

TITLE: Composite Re-Admission Rate (RADM)
Score Range: 0 to 80 points (calculated score for this hospital shown as 64 out of 80)
Graphing Color: Orange
Graphing Position: Second Position, $2^{nd}$ From Left of Horizontal, $2^{nd}$ From Bottom of Stack
Type of Measure: Bundle of Re-Admission Rate measures
Score Modified by CMI: No
Score Modified by Average Per-Case Charge: No
See FIG. 8.

Description:

RADM is a composite measure of thirty (30)-day re-admission rates for AMI, HF, and PN as calculated by CMS using claims data it receives directly from the hospital. Third panics, such as Verras, do not calculate these sub-measures, however CMS does publish the algorithms for peer review.

Calculations of overall re-admit rate on current, all-pay data is provided by each hospital and are accumulated by Verras according to federal guidelines.

Data Sources: The values for each of the re-admission sub-measures are gathered from either the CMS Hospital Compare database or directly from the hospital. The calculations and technical definitions of the 30-day measures are strictly controlled and calculated by CMS so that calculations are consistent. There are specifications manuals published hi-annually by CMS that define the detailed algorithms behind the measures.

Computation Summary:

Metric 2, RADM, is calculated from the overall mean rate of the collection of measures and then inversely translating this mean rate into a score within the range of 0 to 80 points. This "Inverted Rate %" reflects the fact that a reduced readmission rate reflects an improvement. The resulting translation becomes the MVI RADM Component score. As shown in FIG. 9, the overall mean re-admission rate of 19.64% translates to a component score of 64.

Computation Detail:

Metric 2, RADM, computation begins with the gathering of 3 or more years of data from the intended data sources; either directly from the hospital or from a public source such as the CMS Hospital Compare database. The most recent year of the data period gathered is the "Measurement Period" while the prior years are denoted the "Back Period". In the current example, the "Measurement Period" is for calendar year 2012 and the "Back Period" is for 2011 and 2010. The data to be gathered are the numerator and denominator case counts for each sub-measure for each reporting period within the full data period range. Often the reporting periods for these sub-measures are in quarters of a year so they are aggregated up to a year as needed.

Much like QMPS, the computation that drives the RADM score is the Overall Mean Rate %, which is the mean of all rates across the collection of sub-measures across all years in the data period range. In the current example this is the Overall Mean Rate of 19.64% which if rounded is 20%. This mean rate is then translated into the official score for the MVI RADM component by inversion mapping the rate to the point range of 0 to 80 points. The inversion mapping is to account for the fact that a lower readmission rate is desirable and commands a higher MVI RADM component score.

To help with the analysis of a given score, additional computations are performed and done in stages of comparison between the "Measurement Period" and the "Back Period". The first level of analysis begins with the aggregations of the "Back Period" data separate from the "Measurement Period" data. This involves determining the mean rate of the measures in the "Back Period" and then the mean rate of the measures in the Measurement Period.

The additional calculations to help with analysis include the computation of the change in mean rate (Delta. Rate), which measures have improved (Imp), remained static=unchanged (Unc.), or degraded (Deg) when comparing the "Measurement Period" to the Back Period. The calculations of these data, Delta Rate. Imp/Unc flag, Deg flag, etc., are not figured into the calculations of the score but simply considered an aid to physicians' quality improvement activities. FIG. 10 below illustrates these computations along with the detailed steps that follow.

Example: "Measurement Period" RADM-30 PN Pneumonia (PN) Re-Admission Rate: Mean Comparison—17.1%, Delta—0.9% "Measurement Period" Rate—16.7% (2012 'Dark Blue' Numerator 62 and Denominator 372) compared to "Back Period" Rate—17.6% (2011 & 2010 'Dark Green' Num. 122 and Den. 695).

Step 1. Gather or Calculate the Re-Admission Rates and associated numerator case count and denominator case count for each of the selected re-admission rate sub-measures for both the "Measurement Period" and the "Back Period" by gathering the numerator and denominator counts and calculate the resulting rates.

Step 2. (Optional) Calculate the Delta Rate and Imp/Unc Flag and Deg Flag for each of the selected re-admission rate sub-measures for both the "Measurement Period" and the "Back Period". These are calculated as an investigative aid for clinicians' quality improvement activities.

Step 3. Calculate the Overall Mean Rate % by determining the mean of all rates across the collection of sub-measures across all years in the full data period range. Note the Overall Mean Rate is a value between 0 and 1 and the Overall Mean Rate is a value between 0 and 100.

Step 4. Calculate the MVI Component Score for RADM. Using the Overall Mean Rate calculated in the prior step, calculate the score as an inverted percentage of the max. The inversion is done such that the normal improvement direction of a decreasing re-admission rate is translated into an increasing score to align with the positive score model of MVI.

(RADM Component Score [64])=((1−Overall Mean Rate)×[RADM Max Score=80]) rounded to nearest integer.

The RADM Component Score is also known as the MVI RADM Metric Score (64) and is what is used in the graphs as the official score for re-admission rates for the measurement period.

Measurement Period Data:

The "Measurement Period" is the most current 12-month period, in the full data period range. The reporting period of the source data for Metric 2, RADM, is typically a quarter. For transparency and traceability, data is normally stored in its original quarterly form and aggregated together as needed to support the overall computations. Thus with RADM, the "Measurement Period" data consists of four quarters of numerator and denominator data for each sub-measure. See FIG. 11.

Note, when a given measure element is not applicable for the hospital being measured, such as when a hospital has waived the calculation of a sub-measure, as is its option, the sub-measure is excluded from the calculation in a way to hot adversely affect the hospitals MV Score.

Back Period Data:

The "Back Period" data is the range of data that is older than, chronologically comes before, the "Measurement Period" in the full data period range. As mentioned with the "Measurement Period" data, the reporting period of the source data for Metric 2 (RADM) is typically a quarter. For transparency and traceability data is normally stored in its original quarterly form and aggregated together as needed to support the overall computations. Thus with RADM, the "Back Period" data consists of eight or more quarters of numerator and denominator data for each sub-measure. See FIG. 12.

Note, when a given measure element is not applicable for the hospital being measured, such as when a hospital has waived the calculation of a sub-measure, the sub-measure is excluded from the calculation in a way to not adversely affect the hospitals MVI Score.

MORT Measure Definition

Metric 3

TITLE: Risk Adjusted Mortality Rate (MORT)
Score Range: 0 to 144 points (calculated score for this hospital shown as 99 out of 144)
Graphing Color: Yellow
Graphing Position; Third Position, $3^{rd}$ Front Left of Horizontal $3^{rd}$ From Bottom of Stack
Type of Measure: Outcome Aggregation; Collection of Mortality Rates
Score Modified by CMI: Yes
Score Modified by Average Per-Case. Charge: No
See FIG. 13.

Description:

MORT grades and scores the trends of nine (9) risk-adjusted mortality rates comparing the hospital's actual rate to the risk-adjusted norms. As shown in Table 4 below, the bundle of nine mortality measures includes an overall mortality at (all-MD rate), a mortality rate for each of the top 5 clinical service areas (top 5 MDCs with the highest charges or costs), and the three publically reported Thirty (30) Day mortality rates defined by CMS.

TABLE 4

MORT Sub-Measure Collection Example

| KEY | Title |
| --- | --- |
| ALL MDC | Hospital Mortality Rate Comparison |
| 8 | Ortho Mortality Rate Comparison |
| 5 | Circ Mortality Rate Comparison |
| 6 | Dgst Mortality Rate Comparison |
| 4 | Pulm Mortality Rate Comparison |
| 1 | Nerv Mortality Rate Comparison |
| MORT-30-AMI | Acute Myocardial Infarction (AMI) 30-Day Mortality |
| MORT-30-HF | Heart Failure (HF) 30-Day Mortality Rate |
| MORT-30-PN | Pneumonia (PN) 30-Day Mortality Rate |

The hospital's all-MDC rate, as well as specific clinical departments' rates, is calculated for purposes of providing physicians with information they need for quality improvement. This analysis records actual mortality rates, but more importantly, it emphasizes statistically significant improvements and degradations over the years of observations as being of equal important as the actual rates themselves. This emphasis of continuous improvement is reflected in the Trend-Grade Scores creating the quality component score for Metric 3 as will be shown by the analysis.

It should again be re-emphasized that the calculation of Verras' MVI is not only to compare hospitals' outcomes, it is also to give clinicians a tool with which to improve performance. For this reason Trend Grades of A through F are calculated to inform the clinicians if their chronologic performance in these important clinical outcomes is excellent (A) or poor (F).

Data Sources:

The values thr each of these mortality sub-measures are gathered from a combination of data sources. Most of the mortality sub-measures observed rates and expected rates are calculated using discharge data represented in public sources such as the CMS MedPAR data set or direct from a hospital. The 30-day rates however are gathered and aggregated using the pre-calculated data in the CMS Hospital Compare database.

Computation Summary:

Metric 3 (MORT) is calculated by grading the multi-year trend of each of the mortality sub-measures and then aggregating the multiple trend grades into an overall mortality quality component score within the range of 0 to 129.6 points. A CMI component score within the range of 0 to 14.4 points further adjusts the score to account for tertiary and quaternary hospitals' higher acuity patients. The final MORT component score has a range of 0 to 144 points and is arrived at by adding the "Quality Component Score" with the "CMI Component Score". The final MORT component score therefore results in 90% of its score derived directly from the quality component represented by the trend grades and 10% of its score derived from the CMI component, as shown in FIG. 14.

If a hospital has insufficient patients in one of the nine bundled mortality sub-measures, that mortality sub-measure trend grade is not counted, so as to not adversely alter their overall trend grade score.

Computation Detail:

Metric 3 (MORT) computation begins with the gathering of 3 or more years of data from the intended data sources; either directly from the hospital or from a public sources such as the CMS Hospital Compare database. The most recent year of the data period gathered is the "Measurement Period" while the prior years are denoted the Back Period. In the current example, the "Measurement Period" is for calendar year 2012 and the Base Period is for 2011 and 2010. The data to be gathered are the observed mortality rate, expected mortality rate, expected rate upper limit, and expected rate lower limit for each mortality sub-measure for each reporting period within the full data period range. The reporting period for mortality is either quarter or yearly and must be aggregated up to year as needed for consistency across sub-measures.

The computation that drives the MORT score is the Overall Trend Grade Score, which is the summation of the trend grade score for each mortality sub-measure in the collection. The trend grade itself is a reaction to the comparison of the observed mortality rate vs. the expected mortality rate over time. Any missing trend grade scores are set to the default mid-range score before the summation so as to not adversely affect a given facility's MVI score due to lack of patients in a targeted mortality population. To determine the Trend Grade Score for each measure one must flag, the differences between observed and expected rates for each data period and then grade the trend of these difference flags as depicted in FIG. 15 and discussed in steps below.

Step 1. Determine the Top 5 Clinical Service Areas, these are the first 5 Major Diagnostic Categories (MDCs) across the full data period when sorting by MDCs with the greatest total charges (costs).

Step 2. Gather or Calculate the Observed (Actual) Mortality Rate, Expected Mortality Rate, Expected Rate Upper Limit (ExpUL) and Expected Rate Lower Limit (ExpLL) for each of the mortality sub-measures in the collection for each of the data periods. This includes the ALL-MDC sub-measure, the sub-measures for each of the Top 5 MDCs determined in Step 1, and each of the 30-Day Mortality Rates available from CMS. Again, the ALL-MDC rate is the calculation for all MDC's that a hospital services in the given data periods. For the situations in which mortality rates need to be calculated, different methods may be used however the general form is a rate as follows.

[Mortality Rate]=[Count of Deaths in Target Population]/[Target Population Count]

Step 3. Determine the Delta Mortality Rate for each sub-measure in the collection for both the "Measurement Period" and the Back. Period.

[Delta Mortality Rate]=[Observed Mortality Rate]−[Expected Mortality Rate]

Step 4. Determine the Delta Flag for each sub-measure for both the "Measurement Period" and "Back Period". The Delta Flag Numeric flag indicating a value of 2 if "Measurement Period" rate is statistically, significantly improved over expected, or a value of 1 if the "Measurement Period" rate is unchanged with respect to the expected, or a value of 0 if the "Measurement Period" rate is significantly degraded from the expected. There are different methods this may be accomplished, however one method is to compare the observed rate to the expected range,

[Delta Flag]=2 WHEN [Observed Mortality Rate]<[ExpLL]

[Delta Flag]=1 WHEN [Observed Mortality Rate]>[ExpLL] and [Observed Mortality Rate]<[ExpUL]

[Delta Flag]=0 WHEN [Observed Mortality Rate]>[ExpUL]

Step 5. Determine the "Trend Grade" for each measure. The Trend Grade=Alpha assignment (A, B, C, D, F) based on comparison of the "Measurement Period" and "Back Period" delta flags. A is considered better than F and are assigned such the improvement direction of decreasing (improving) mortality rates over the data periods tends towards an A. Increasing mortality rates (degrading) over time tend towards an F. The Alpha codes are assigned as indicated below in Table 5 to assist clinicians with quality improvement activities.

TABLE 5

Trend Grade Assignment

A = "Measurement Period" Delta Flag = 2, "Back Period" Delta Flag = 2; consistently & significantly improved
B = "Measurement Period" Delta Flag = 2, "Back Period" Delta Flag = 1; significantly improved in one period
B = "Measurement Period" Delta Flag = 1, "Back Period" Delta Flag = 2; significantly improved in one period
C = "Measurement Period" Delta Flag = 2, "Back Period" Delta Flag = 0; significantly improved in Measurement Period

TABLE 5-continued

Trend Grade Assignment

C = "Measurement Period" Delta Flag = 1, "Back Period" Delta Flag = 1; unchanged or insignificant change
D = "Measurement Period" Delta Flag = 1, "Back Period" Delta Flag = 0; degradation in one period
D = "Measurement Period" Delta Flag = 0, "Back Period" Delta Flag = 1; degradation in one period
D = "Measurement Period" Delta Flag = 0, "Back Period" Delta Flag = 2; sharp degradation in Measurement Period
F = "Measurement Period" Delta Flag = 0, "Back Period" Delta Flag = 0; degradation in both periods Step 6. Determine the "Trend Grade Score" for each measure. The Trend Grade Score Numeric assignment to the Trend Grade for purpose of aggregation into an overall subscore or index. The Trend Grade Alpha to Numeric Map assigned as indicated below in Table 6.

TABLE 6

Trend Grade Score Assignment

A = 14.4
B = 13.4
C = 12.4
D = 11.4
E = 0

Step 7. Default Missing Sub-Measures by assigning them a Trend Grade of C and therefore a Trend Grade Score of 12.4.

Step 8. Determine the "Overall Trend Grade Score". Add up the Trend Grade Scores for each sub-measure and assign this total score as the "Overall Trend Grade Score". Given there are nine mortality sub-measures with a maximum possible trend grade score of 14.4 each, the Trend Grade Score range is 0 to 129.6 (9×14.4).

Step 9. Assign the "Quality Component Score" for MORT to be equal to the Overall Trend Grade Score. In this example, the Quality Component Score is 93.80 points out of 129.6 and is computed from the aggregation of trend grade scores for all nine measures. In this example, no missing, measure corrections are needed. The quality component score represents 90% of the total points possible points for the WI Mortality Metric Score.

Step 10. Calculate the "CMI Component Score". The CMI component score for MORT represents 10% of the total possible points for the WI Mortality Metric Score. It is computed using the formula discussed earlier in "Global Drivers" but repeated here to illustrate the specifics for MORT score range.

(CMI Component Score for Mort)=([14.4]/[3 Year CMI Max Across All Hospitals])×[3 Year Average CMI of Target Hospital]

Step 11. Calculate the MVI Component Score for Mortality. Using the results of the calculations in the prior steps, one can now add the mortality quality component and CMI component scores together. The resulting score ranges from 0 to 144. In the current example a score of 99 is achieve for MORT.

(MORT Component Score [90])=(MORT Quality Component Score [93.80])+(CMI Component Score for MORT [5.05]).

The MORT Component Score is also known as the MVI Mortality Metric Score (90) and is what is used in the graphs as the official score for mortality for the measurement period.

Measurement Period Data:

The "Measurement Period" is the most current 12-month period in the full data period range. The reporting period of the source data for Metric 3 (MORT) is typically a year. In the event that some of the data is supplied as quarters, this data is aggregated up to the year level for consistency with the major form of reporting period for the other mortality sub-measures in the collection. Thus with MORT, the "Measurement Period" data consists of 1 year of observed mortality rate, expected mortality rate, expected lower limit (ExpLL), and expected upper limit ExpUL) data for each sub-measure in the collection. See FIG. 16.

Note that the MDC 8, Ortho Mortality Rate Comparison has a DeltaFlag of 2. The −0.9% is a lower and better Delta generated by an Observed 0.6 rate, which is lower (better) than Expected 1.4% (Expected Upper Limit Confidence Interval 1.5%–Expected Lower Limit confidence 1.3%).

Back Period Data:

The "Back Period" is the range of data that is chronologically before (older) than the "Measurement Period" in the full data period range. As mentioned with the "Measurement Period" data, the reporting period of the source data for Metric 3 (MORT) is typically a year. In the event that some of the data is supplied as quarters, this data is aggregated up to the year level for consistency with the major form of reporting period for the other mortality sub-measures in the collection. Thus with MORT, the "Back Period" data consists of 2 or more years of observed mortality rate, expected mortality rate, expected lower limit, and expected upper limit data for each sub-measure in the collection. See FIG. 17.

Back Period Data (2010-2011) aggregates the risk-adjusted, actual vs. expected mortality rates of the eight quarters for the "Back Period" years (2011-2010 in this case.) Note that the MDC 6 Dgst Mortality Rate Comparison has a DeltaFlag of 0 because of a 0.7% (higher and worse) Delta generated by an Observed 3.1 rate, which is higher (worse) than Expected 2.5% (Expected Upper Limit Confidence Interval 2.0%–Expected Lower Limit Confidence interval 2.4%).

MORB Measure Definition

Metric 4

TITLE: Risk Adjusted Morbidity Rate (MORB)
Score Range: 0 to 174 points (calculated score for this hospital shown as 67 out of 174)
Graphing Color: Red
Graphing Position: Fourth Position, $4^{th}$ From Left of Horizontal, $4^{th}$ From Bottom of Stack
Type of Measure: Outcome Aggregation; Excessive LOS
Score Modified by CMI: Yes
Score Modified by Average Per-Case Charge: No
See FIG. 18.

Description:

MORB is a measurement of a hospital's morbidity (complications) using a monitor on length of stay. Empirical evidence from analyses in over 300 Verras hospitals and numerous authors have noted the positive relationship of longer Lengths-Of-Stay (LOS) and morbidities. Verras defines patients as having some type of morbidity when the observed LOS is 4 or more days longer than the patients' risk-adjusted norms. The hospital's 10 MS-DRGs with the greatest number of charges (or costs) are selected to compute the hospital's morbidity rates. The MORB rate does not attempt to determine the type of morbidity, such as infection or pathophysiologic complication. Verras routinely analyzes these cases in greater detail to determine the types and etiologies that have cause the excessive LOS as a part of the hospital's clinical process improvement activities.

Computation Summary:

A hospital's risk-adjusted morbidity rate (MORB) is calculated by determining the overall mean rate of MS-DRG sub-measures and translating their mean rates into a morbidity quality component score within a range of 0 to 156.6 points. This translation both maps the rates into scores and inverts the improvement direction so decreasing morbidity rates (improvements) translate to increasing scores. A "CMI component score" within the range of 0 to 17.4 points further adjusts the "Quality Component Score". The final MORB MVI component score has a range of 0 to 174 points and computed by adding the quality component score with the CMI component score. The final MORB component score therefore results in 90% of its score derived directly from the quality component represented by the morbidity rates and 10% of its score derived from the CMI component as shown in FIG. 19, to account for the tertiary and quaternary hospitals' higher acuity patients.

In this example, the hospital had an average, Overall Mean Morbidity Rate of 20.27%, which, on the inverted sliding scale, translates to a Quality Component score of 60.6. This score, combined with the 6.10 CMI Component=66.7 (rounded to 67) Score for the MVI Metric 4 component.

Computation Detail:

Metric 4 (MORB) computation begins with the gathering of 3 or more years of data from the relevant data sources; either directly from the hospital or from a public sources such as the CMS MedPAR database. The most recent year of the data period gathered is the "Measurement Period" while the prior years are denoted as the "Back Period". In the current example, the "Measurement Period" is for calendar year 2012 and the "Back Period" is for 2011 and 2010. The data to be gathered are the numerator and denominator counts for each MS-DRG's morbidity sub-measure for each reporting period within the data period range. The reporting period for morbidity is by year.

The computation that drives the MORB score is the Overall Mean Rate which is the mean of each morbidity rate for each MS-DRG in the Top 10 DRG collection for both the "Measurement Period" and the "Back Periods". The rates represent those cases within a specific MS-DRG that have a Length of Stay (LOS) that is 4 or more days longer than the severity-adjusted, expected.

As is common with the other MVI metrics, additional computations are performed at this time and done in stages of comparison between the "Measurement Period" and the "Back Period". The first level of analysis begins with the aggregations of the "Back Period" data separate from the "Measurement Period" data. This involves determining the mean rate of the sub-measures in the "Back Period" and then the mean rate of the sub-measures in the Measurement Period.

The additional calculations to help with analysis include the computation of the change in mean rate (Delta Rate), which measures have improved (imp), stayed-the-same=unchanged (Uno), or degraded (Deg) when comparing the "Measurement Period" to the Back Period. The calculations of these data, Delta Rate, Imp/Unc flag, Deg flag, etc., are not figured into the calculations of the score but simply considered an aid to assist clinicians as to where to direct their attentions in the hospital's clinical process improvement efforts.

The calculation of the overall mean rate as well as the common additional computations are illustrated in FIG. 20 and detailed further in the steps that follow for these 10 most resource intense MS-DRGs.

Example: Comparing the 2012 "Measurement Period" Rate for DRG 853 (Infectious & Parasitic Diseases) of 31.0% (Numerator—9 and Denominator—29), with the 32.8% (Num. 21 & Den. 64) yields an Aggregated Mean of 31.92%. This change represented a decline (delta—1.8%) defining it as an improvement, indicated by the 1 in the Improved/Unchanged (Imp/Unc) column. (The lower the morbidity rate, the better the quality).

The Mean of all 10 MS-DRGs is recorded as Metric 4 Net: 20.27% (blue arrow) with an Aggregated Delta of −1.0%. Additionally, there were 7MS-DRGs Imp/Unc and 3 Degraded, which is information for clinicians who manage those cases to use for quality improvement purposes. The physicians of each clinical service need to know their risk-adjusted morbidity rates for quality assurance purposes.

Step 1. Determine the Top 10 MS-DRGs, these are the first 10 Diagnostic Reporting Groups (DRGs) across the full data period when sorting the MS-DRGs with the greatest total charges (or costs).

Step 2. Gather or calculate the Risk-Adjusted Morbidity Rate and associated numerator case count and denominator case count for each of the 10 MS-DRGs determined in Step 1 for both the "Measurement Period" and the "Back Period". The denominator is the total number of cases in a given MS-DRG and the numerator is the count of cases in a given MS-MG that have an LOS greater than or equal to the Risk Adjusted Expected LOS+4 days.

Step 3. (Optional) Calculate the Delta Rate and Imp/Unc Flag and Deg Flag for each of the 10 MS-DRGs determined in Step 1 for both the "Measurement Period" and the "Back Period". These are calculated as an investigative aid to physicians and hospital personnel.

Step 4. Calculate the Overall Mean Morbidity Rate for the full data period. Calculate the mean morbidity rate for each of the 10 MS-DRGs determined in Step 1 and using the morbidity rates calculated in Step 2. Then calculate the mean of the entire set of rates as the Overall Mean Morbidity Rate $$[\text{Overall Mean Morbidity Rate}] = ([\text{Mean Morbidity Rate DRG1}] + \ldots + [\text{Mean Morbidity Rate DRG10}])/10$$

Step 5. Calculate the "Quality Component Score" for MORB by translating the Overall Mean Morbidity Rate into a score with the range of 0 to 156.6 points. The translation both maps the percent to a score and inverts the improvement direction such that a lower morbidity percent results in a higher score. The translation is accomplished using the scale represented in Table 7 below,

TABLE 7

Overall Mean Morbidity Rate-To-Score

| | Greater or Equal | |
|---|---|---|
| 33.00% | 33% | 1.6 |
| 32.00% | 32.99% | 6.6 |
| 31.00% | 31.99% | 8.6 |
| 30.00% | 30.99% | 10.6 |
| 29.00% | 29.99% | 15.6 |
| 28.00% | 28.99% | 20.6 |
| 27.00% | 27.99% | 25.6 |
| 26.00% | 26.99% | 30.6 |
| 25.00% | 25.99% | 35.6 |
| 24.00% | 24.99% | 40.6 |
| 23.00% | 23.99% | 45.6 |
| 22.00% | 22.99% | 50.6 |
| 21.00% | 21.99% | 55.6 |
| 20.00% | 20.99% | 60.6 |
| 19.00% | 19.99% | 65.6 |
| 18.00% | 18.99% | 70.6 |
| 17.00% | 17.99% | 75.6 |
| 16.00% | 16.99% | 80.6 |
| 15.00% | 15.99% | 85.6 |
| 14.00% | 14.99% | 90.6 |
| 13.00% | 13.99% | 95.6 |
| 12.00% | 12.99% | 100.6 |
| 11.00% | 11.99% | 105.6 |
| 10.00% | 10.99% | 110.6 |
| 9.00% | 9.99% | 115.6 |
| 8.00% | 8.99% | 120.6 |
| 7.00% | 7.99% | 125.6 |
| 6.00% | 6.99% | 130.6 |
| 5.00% | 5.99% | 135.6 |
| 4.00% | 4.99% | 140.6 |
| 3.00% | 3.99% | 145.6 |
| 2.00% | 2.99% | 150.6 |
| 1.00% | 1.99% | 153.6 |
| Less Than 1% | 0.99% | 156.6 |

Step 6. Calculate the CMI Component Score. The CMI component score for MORB represents 10% of the total possible points for the MVI Morbidity Metric Score. It is computed using the formula discussed earlier in "Global Drivers" but repeated here to illustrate the specifics for MORB score range.

[CMI Component Score for MORB]=([17.4]/[3 Year CMI Max Across All Hospitals])×[3 Year Average CMI of Target Hospital]

Step 7. Calculate the MVI Component Score for Morbidity. Using the results of the calculations in the prior steps, one can now add the morbidity quality component and CMI component scores together. The resulting score ranges from 0 to 174. In the current example a score of 67 is achieve for MORB.

(MORB Comp. Score [67])=(MORB Quality Comp. Score [60.60])+(CMI Comp. Score [6.10]).

The MORB Component Score is also known as the MVI Metric #4 Score (67) and is what is used in the graphs as the official score for morbidity for the measurement period.

Measurement Period Data:

The "Measurement Period" is the most current 12-month period in the full data period range. The reporting period of the source data for Metric 4 (MORB) is typically a year. Thus with MORB, the "Measurement Period" data consists of 1 year of morbidity rate numerator and denominator case counts for each of the top MS-DRGs. See FIG. 21.

The year of data from 2012 had 9 patients in the Num. and 29 in the Den., which yielded an Aggregated rate of 31.0%.

Back Period Data:

The "Back Period" data is the range of data that chronologically before (older) than the "Measurement Period" in the full data period range. As mentioned with the "Measurement Period" data, the reporting period of the source data for MORB is typically a year. Thus with MORB, the "Back Period" data consists of 2 or inure years of morbidity rate numerator and denominator case counts for each of the top MS-DRGs. See FIG. 22.

The 2011 rate of 31.6% (Num. 12 and Den. 38) is aggregated with the 2010 rate of 34.6% (Num. 9 and Den. 26) to yield the 32.6% Aggregated Rate.

The 2011 rate of 31.6% (Num. 12 and Den. 38) is aggregated with the 2010 rate of 34.6% (Num. 9 and Den. 26) to yield the 32.6% Aggregated Rate.

RIV Measure Definition

Metric 5

TITLE: Reduction In Variation (RIV)
Score Range: 0 to 126 points (calculated score for this hospital shown as 118 out of 126)
Graphing Color: Light Blue
Graphing Position: Fifth Position, $5^{th}$ From Left of Horizontal, $5^{th}$ From Bottom of Stack
Type of Measure: Charge (or Cost) Variation
Score Modified by CMI: Yes
Score Modified by Average Per-Case Charge: No
See FIG. 23.

Description:

RIV measures the reduction in charge (or cost) variations for the top 5 clinical service areas. The calculations are done using a hospital's top 5 MS-DRGs (those with the highest numbers of resource consumption in dollars (charges or costs) in each of the top 5 MDCs (those with the highest numbers of resource consumptions in dollars (charges or costs). FIG. 24 graphically illustrates Reduction in Variation (RIV) over a 3-year period using ovals that encircle a 2 St. Dev. Charges and LOS volume of cases each year for a given clinical condition. The trend of the ovals' migration is exaggerated to make the point. (An "up and to the right" migration of the ovals, indicates the charge [cost] and LOS Means [averages—M1 to M2 to M3] are improving over time.)

Patients' data are risk-adjusted and their plots are placed on this 4-quadrant graph. The white lines of the 4-quadrant graph represent a regional norm for Charges (horizontal line) and Length of Stay (LOS) (vertical line). The ovals represent 2 Standard Deviation ovals with 95% of patient's charges and LOS within the ovals. During year 1 (dashed line), the largest oval has a charge variance from +$4,000 to −$4,000 or total variance of $8,000 (read from Delta Charges on left axis). The LOS variation is from +2.5 day shorter than the norms (to the right of the vertical line) to −2.5 day longer than the norm for total LOS variation of 5 days (read Delta LOS per patient below graph). The Mean (Average) for year 1 (M1) is below and to the left of the charge and LOS averages meaning the hospital has inefficient outcomes compared to the norm being used.

In a typical use of RIV measurement, after the data has established that there are no significant morbidity or mortality problems, the providers' efficiencies are then evaluated. Verras provides the clinical information with which physicians modify their practice patterns based on their own best-demonstrated outcomes. Efficiencies are created by physicians whose future ordering patterns replicate the clinical processes that created the most efficient outcomes represented by those patients' outcomes in the upper portion of the right upper quadrant (RUQ). In this "green" cohort, the doctors used fewer resources than the norms and discharged their patients from the hospital whose lengths of stay that were shorter than the norms. Verras terms this educational process "physician-directed, best demonstrated practices". Physicians use these processes to develop order sets that are continuously improved to insure ever-increasing efficacies and efficiencies.

In this particular graph, during year 2, the dotted line indicates that the oval has been reduced (Reduction in Variation) in both charges and LOS and just as importantly, the outcomes have improved because the M2 (Mean) of the outcomes have moved up and to the right. During year 2, the physicians used fewer resources and fewer days per patient. Year 3 (solid line), demonstrates further improvements because the ovals are smaller (RIV) and the Mean 3 has again moved up and to the right. This pattern of RN and improving, outcomes is the essence of quality improvement and indicates the clinicians and hospital personnel are reasoning together to achieve greater efficacies and efficiencies in their practices.

The MVI statistically records the RIV for charges or costs as Metric 5. When this established metric of quality is combined with Mortalities, Morbidities etc., providers, employers and patients have a very easily interpreted idea as to how each hospital is performing from year to year. When quality metrics are combined with a comparative resource consumption measure, providers and purchases have an objective measure of the medical enterprise's value, which is both quality and costs.

Data Sources:

The variation values for each of the top 5MS-DRGs within the top 5 clinical service areas are calculated using public discharge data such as CMS MedPAR data or data direct from the hospital's Uniform Hospital Discharge Data Set (UH-DDS).

Computation Summary:

Metric 5, RIV, is calculated by determining the number of MS-DRGs (Top 5 for each of the Top 5 clinical service areas) for which the charge variation is significantly improved, unchanged or significantly degraded when comparing the "Measurement Period" data to the "Back Period" data. The count of MS-DRGs that have improved or unchanged vs. degraded yields a number called the Net Change %, which is then translated into the RIV quality component score within the range of 0 to 113.4 points. A CMI component score within the range of 0 to 0.12.6 points further adjusts the total score. The final RIV component score has a range of 0 to 126 points and is arrived at by adding the quality component score with the CMI component score. The final RIV component score therefore results in 90% of its score derived directly from the quality component represented by the net change percentage and 10% of its score derived from the CMI component, as shown in FIG. 25.

Computation Detail:

Metric 5, RIV, computation begins with the gathering of 3 or more years of data from the intended data sources; either directly from the hospital or from a public source such as the CMS MedPAR database. The most recent year of the data period gathered is the "Measurement Period" while the prior years are denoted the "Back Period". In the current example, the "Measurement Period" is for calendar year 2012 and the "Back Period" is for 2011 and 2010. (This assumes these computations are being performed early in the year 2013 after all of the hospital data for 2012 has been amassed.) The data to be gathered includes the charge (or cost) variation and case counts for each of the Top 5 MS-DRGs within each of the Top 5 clinical service areas for each reporting period within the full data period range. The reporting period for Reduction In Variation is by year.

The computation that drives the RIV score is the Net Change %, which is the percent of Top 5 MS-DRGs across each of the Top 5 clinical service areas that have either experienced an improved RIV as exhibited by a significant Reduction In Variation or have remained statistically the same when comparing the "Measurement Period" to the "Back Period".

A number of additional computations are needed to arrive at the Net Change %. The additional computations include the determination of the change in mean variation (Delta Variation), flagging which variations have improved (Imp), stayed-the-same (Uric), degraded (Deg). If the changes are statistically significant the data will be tagged with a (SigTest). These additional computations, which are optional aids in other components of MVI, are critical elements in the determination of the Net Change % for RIV. The computations are performed as part of a direct comparison of "Measurement Period" data vs. "Back Period" data as illustrated, in FIG. 26 and discussed in the detailed steps that follow.

Step 1. Determine the Top 5 clinical service areas, these are the first 5 Major Diagnistice Categories (MDCs) across the full data period when sorting by MDCs with the greatest total charges (or costs).

Step 2. Determine the Top 5 MS-DRGs for each of the Top 5 clinical service areas determined in step 1. These are the MS-DRGs within each of the respective MDCs with the greatest total charges (or costs) across the full data period.

Step 3. For both the "Measurement Period" and the "Back Period", calculate the charge (or cost) variation and number of cases for each MS-DRG determined in step 2. The charge variation is calculated as the standard deviation of the delta charge. The delta charge is calculated as the risk-adjusted difference equal to expected charge—actual charge for cases of equivalent severity. (Charges are replaced by costs if such data are available or cost variation is preferred. Alternatively calculations can be carried out in charges and then converted to costs using a hospitals charge to cost ratio in this example).

Step 4. Calculate the Delta Variation for the"Measurement Period" vs the Back Period:

[Delta Variation]=[Measurement Period Variation]−[Back Period Variation]

Step 5. (Optional) Calculate the Mean Variation for the"Measurement Period" vs the Back Period. Although the Mean Variation is not used in the scoring, it can be useful in analysis of the trend.

[Mean Variation]=([Measurement Period Variation]+[Back Period Variatiorn])/2

Step 6. Calculate the Variation Confidence Interval Upper and Lower Limits for both the "Measurement Period" and "Back Period". This is calculated as a confidence interval of a standard deviation. Typically this is calculated using a chi squared distribution but other methods may be used as best determined. As an example using a formula defined for Microsoft Excel.

$$[VCI\ \text{Upper Limit}] = \sqrt{\frac{([\#\text{Cases}]-1)\times[\text{Variation}]2}{CHINV(0.025,[\#\text{Cases}]-1)}}$$

$$[VCI\ \text{Lower Limit}] = \sqrt{\frac{([\#\text{Cases}]-1)\times[\text{Variation}]2}{CHINV(0.975,[\#\text{Cases}]-1)}}$$

Step 7. Flag the Variations that are significantly different vs the same. First determine and flag the variation comparisons between the "Measurement Period" and "Back Period" that are statistically significant. This is accomplished by comparing the VCI Upper & Lower Limits of the "Measurement. Period" with the VCI Upper and Lower Limits of the "Back Period". If the Limits of the two periods do not overlap, then there the Significance Test Flag should be set to (1). Once the significance flag is set, then the significantly degraded flag can be set for any variation that is greater in the "Measurement Period" vs the "Back Period" and also has the Significance Flag set. In the absence of significant degradation, the Imp/line Flag is set since the variation is either significantly improved or of insignificant difference.

(initialize flags for each MS-DRG to 0)

[SigTest]=1 When "Measurement Period" VCI UL-VCI LL Overlaps "Back Period" VCI UL-VCI LL

[SigDeg]=1 When "Measurement Period" Variation>"Back Period" Variation AND SigTest=1

[Imp/Unc]=1 When "Measurement Period" Variation<"Back Period" Variation AND SigTest=1

[Imp/Unc]=1 When SigTest=0

Step 8. Calculate the Net Change % by taking the difference between the MS-DRG sub-measures that have improved or stayed-the same vs significantly degraded and dividing the difference by the count of MS-DRG sub-measures that are involved in the calculation, if an MS-DRG has a low population such that variation cannot be properly compared, then the measured is flagged as not measurable and excluded from calculations.

[NetChange %]=([#MS-DRGs Imp/Unc]-[#Drgs SigDeg])/(([#MS-DRGs Imp/Unc]+[#Drgs SigDeg])

Step 9. Determine the Quality Component Score using the Net Change %. The Net Change % is directly applied to the quality component range of 113.4 points to determine the resulting quality score.

[RIV Quality Component Score]=([Net Change %]× [RIV Quality Component Max Score=113.4])

Step 10. The CMI component score for RIV is calculated, which represents 10% of the total possible points for the MVI RIV Metric Score. It is computed using the formula discussed earlier in "Global Drivers" but repeated here to illustrate the specifics for RIV score range.

[CMI Component Score for RIV]=([12.6]/[3 Year CMI Average Max Across All Hospitals])×[3 Year Average CMI of Target Hospital]

Step 11. Calculate the MVI Component Score fear RIV. Using the results of the calculations in the prior steps. The RIV quality component and CMI component for RIV scores are added together. The resulting score ranges from 0 to 126. In the current example a score of 118 is achieve for RIV.

(RIV Comp. Score [118])=(RIV Quality Comp. Score [113.42])+(CMI Comp. Score [4.42])

The RIV Component Score is also known as the MVI REV Metric Score and is what is used in the graphs as the total score for Reduction In Variation (118) for the measurement period.

Example

Referring, back to the hospital example above in FIG. 21, observe DRG 228 under Cardiology (MDC 5). The variation in resource consumption in the "Back Period". Years 2010-2011 (dark green) is $65,284 for 10 cases with Variation Confidence Intervals—Lower Limit and Upper Limits (VCI_LL—$48,225 and VCI_UL—$101,039).

During 2012 "Measurement Period" (dark blue) the observed variation is $10,108 on 8 cases with variation intervals of $6,083/$20,573. This Reduction In Variation from $65,284 in the "Back Period" to $10,108 in the "Measurement Period" represents a Statistically Significant reduction of −$55,176 as recorded in the "Measurement Comparison" column (orange). The fact that it is significant is indicated by a "1" in the SigTest column.

Measurement Period Data:

The "Measurement Period" is the most current 12-month period in the full data period range. The reporting, period of the source data for Metric 5, RIV, is typically a year. Thus with RIV, the "Measurement Period" data consists of 1 year of charge variation and case counts for each of the Top 5 MS-DRGs within the Top 5 clinical service areas. See FIG. 27.

Back Period Data:

The "Back Period" data is the range of data that chronologically comes before (older), the "Measurement Period" in the full data period range. As mentioned with the "Measurement Period" data, the reporting, period of the source data for Metric 5 (RIV) is typically a year. Thus with RIV, the "Back Period" data consists of 2 or more years of charge variation and case counts for each of the Top 5 MS-DRGs within the Top 5 clinical service areas. See FIG. 28.

RESC Measure Definition

Metric 6

TITLE: Resource Consumption (RESC)
Score Range: 0 to 230 points (calculated score for this hospital shown as 169 out of 230)
Graphing Color: Green
Graphing Position: Sixth Position, $6^{th}$ From Left of Horizontal, $6^{th}$ From Bottom of Stack
Type of Measure: Charge (or Cost) Inflation Trend
Score Modified by CMI: Yes
Scare Modified by Average Per-Case Charge: Yes
See FIG. 29.

Description:

Resource Consumption RESC in this hospital and measured using charges or costs. It is optimal to assess resource consumption using fully allocated costs if the hospital's IT department is able to support such data. However, costs are often not available and charges are therefore used. This is acceptable because the charge master is the same for all patients, making physicians' intra-hospital comparisons valid as well as being adequate for determining the hospital's MVI.

The RESC metric determines if fewer or greater numbers of resources were consumed over time when comparing the measurement data period to the back data period. The calculations monitor the charges (or costs) for the Top 5 clinical service areas (those with the highest numbers of resource consumptions in charges (or costs) dollars.

Data Source:

The per-discharge charge (or cost) values for each of the Top 5 clinical service areas are calculated using either data directly from the hospital's Uniform Discharge Data Set (UHDDS) or public data such as CMS MedPAR data for inter-hospital comparisons.

Computation Summary:

The summary displays the inflation rates of resource consumption over 3 years of the most resource intense five clinical services. In this example hospital, the services are: Respiratory (MDC 4), Cardiology (MDC 5), Neurology (MDC 1), Orthopedics (MDC 8), Infectious Disease (MDC 18). The calculations are done for RESC using hospitals' Inpatient and hospital-associated Outpatient Data for all clinical services. (The MDC 1 medical MS-DRGs are distinguished from the MS-DRGs associated with Neurosurgery.)

Calculations using the 5 clinical services determine the metric's score, which in this Neurology example is a deflation rate of −4%, recorded in the "Overall Per-Case % Change" in the dark green box. See FIG. 30.

Computation Detail:

Metric 6, RESC, computation begins with the gathering of 3 or more years of data from the intended data sources; either directly from the hospital or from a public sources such as the CMS MedPAR database. The most recent year of the data period gathered is the "Measurement Period", while the prior years are denoted as the back years. In the current example, the "Measurement Period" is for calendar year 2012 and the "Back Period" is for 2011 and 2010. The data to be gathered includes the total charges (or costs) and case counts for each of the top 5 MDC defined clinical service areas for each reporting period within the data period range. The reporting period for resource consumption is by year.

The computation that drives the RESC score is the Overall Per-Case Change which is the percent of change in the per-case-charge (or cost) when comparing the "Measurement Period" to the "Back Period" for each of the Top 5 clinical service areas as defined by those MDC's that have the highest total charges (or costs). The percent change is based on the difference between the "Measurement Period" per-case charge (or cost) and the "Back Period" charge (or cost), this difference is referred to as the "Delta".

As is Common With the other metrics, additional computations are performed at this time and done in stages of comparison between the "Measurement Period" and the "Back Period". The first level of analysis begins with the aggregations of the "Back Period" data. This includes but not limited to determining the mean per-case charge (or cost) of the MDC in the "Measurement Period" vs. the "Back Periods".

The additional calculations to help with analysis include the computation of the mean per-case charge or cost (mean), which MDCs have improved (Imp), stayed-the-same (unchanged 'Unc'), or degraded (Deg) when comparing the "Measurement Period" to the "Back Period". The calculations of these data. Delta Per-Case. Imp/Unc flag, Deg flag, etc., are not figured into the calculations of the score but simply considered an aid to assist the appropriate clinicians by determining where process improvements should be focused.

The calculation of the overall Per-Case percent change as well as the common additional computations are illustrated below in FIG. 31 and detailed further in that steps that follow.

Step 1. Determine the Top 5 clinical service areas, these are the first 5 major diagnostic categories (MDC) across the full data period when sorting by MDCs with the greatest total charges (or costs)

Step 2. For both the "Measurement Period" and the "Back Period Data", calculate the per-case charge (or cost) for each MDC determined in step 1. The per-case charge is calculated as the total charges (or costs) for a given MDC divided by the total cases for the given MDC. (Charges are simply replaced by costs if supported by the data and a cost level measure is preferred.) Costs are always used when determining physicians' reimbursements, so it may be necessary to carry out the calculations in charges and then converted to costs using a hospital's charge to cost ratio.

Step 3. Calculate the Delta Per-Case Charge (or Cost) for the "Measurement Period" vs the "Back Period". (In this hospital example the Delta Per-Case Charge is −$2,051 see FIG. 25 above.)

[Delta Per-Case Charge]=[Measurement Period Per-Case Charge]−[Back Period Per-Case Charge]

Step 4. Calculate the Per-Case Change by dividing the Delta Per-Case Charge for Cost) by the Per-Case Charge of the "Back Period". This is first done for each of the Top 5 MDC's and then averaged cross the 5 MDCs to make the Overall Per-Case Change. (In this example hospital the Per-Case is −4.03%—see FIG. 25).

[Per-Case % Change]=[Delta Per-Case Charge]/[Back Period Per-Case Charge]

Step 5. Determine the Quality Component Score using the Overall Per-Case %, Change. The Overall Per-Case % Change needs to be translated into the Quality Component Score for RESC with a range of 0 to 156.6 points. The translation both maps the percent to a score and inverts the improvement direction such that a negative Per-Case change % results in a higher score. The translation is accomplished using, the scale represented in Table 8 below. (In this example hospital the Per-Case % Change to Score is −403% to 96.)

TABLE 8

Resource Consumption - Overall Per-Case % Change-To-Score

| | Greater or Equal | |
|---|---|---|
| 20.00% | 20% | 3 |
| 19.00% | 19.99% | 6 |
| 18.00% | 18.99% | 9 |
| 17.00% | 17.99% | 12 |
| 16.00% | 16.99% | 15 |
| 15.00% | 15.99% | 20 |
| 14.00% | 14.99% | 25 |
| 13.00% | 13.99% | 30 |
| 12.00% | 12.99% | 35 |
| 11.00% | 11.99% | 40 |

TABLE 8-continued

Resource Consumption - Overall Per-Case % Change-To-Score

| | | |
|---|---|---|
| 10.00% | 10.99% | 45 |
| 9.00% | 9.99% | 50 |
| 8.00% | 8.99% | 55 |
| 7.00% | 7.99% | 60 |
| 6.00% | 6.99% | 65 |
| 5.00% | 5.99% | 70 |
| 4.00% | 4.99% | 75 |
| 3.00% | 3.99% | 80 |
| 2.00% | 2.99% | 82 |
| 1.00% | 1.99% | 84 |
| 0.00% | 0.99% | 86 |
| 0.00% | −0.99% | 88 |
| −1.00% | −1.99% | 90 |
| −2.00% | −2.99% | 92 |
| −3.00% | −3.99% | 94 |
| −4.00% | −4.99% | 96 |
| −5.00% | −6.99% | 98 |
| −7.00% | −8.99% | 100 |
| −9.00% | −10.99% | 102 |
| −11.00% | −13.99% | 104 |
| −14.00% | −16.99% | 106 |
| Less Than −17% | −17.00% | 107 |

Step 6. The Average Charge Component Score for RESC is calculated next and represents 43% of the total possible points for the MVI RESC Metric Score. It is computed using the formula discussed earlier in "Global Drivers" but repeated here to illustrate the specifics for RESC score range.

[AVG CHG Component Score for RESC]=Score derived from applying the relevant hospital's 3 year Average Charge across all services into the Score Translation Table, shown below as Table 9. (This hospital's Average Charge is $37,441 (see FIG. 2), which yields an Average Charge-to-Score of 65 as seen in the Translation Table 9, below).

TABLE 9

Score Translation Table:
Resource Consumption - Average Charge-to-Score

| | Greater or Equal | |
|---|---|---|
| $100,000.00 | 100K | 1 |
| $95,000.00 | 99,999.99 | 5 |
| $90,000.00 | 94,999.99 | 10 |
| $85,000.00 | 89,999.99 | 15 |
| $80,000.00 | 84,999.99 | 20 |
| $75,000.00 | 79,999.99 | 25 |
| $70,000.00 | 74,999.99 | 30 |
| $65,000.00 | 69,999.99 | 35 |
| $60,000.00 | 64,999.99 | 40 |
| $55,000.00 | 59,999.99 | 45 |
| $50,000.00 | 54,999.99 | 50 |
| $45,000.00 | 49,999.99 | 55 |
| $40,000.00 | 44,999.99 | 60 |
| $35,000.00 | 39,999.99 | 65 |
| $30,000.00 | 34,999.99 | 70 |
| $25,000.00 | 29,999.99 | 75 |
| $20,000.00 | 24,999.99 | 80 |
| $15,000.00 | 19,999.99 | 85 |
| $10,000.00 | 14,999.99 | 90 |
| $5,000.00 | 9,999.99 | 95 |
| Less Than 5K | 4,999.99 | 100 |

Step 7. The CMI Component Score for RESC is calculated next and represents 10% of the total possible points for the MVI RESC Metric Score. It is computed using the formula discussed earlier in "Global Drivers" but repeated here to illustrate the specifics for RIV score range. The Maximum possible Point (Score) for the CMI Component is 23 (10% of 230 possible). Using this example hospital and the formula below, the CMI Component Score is 8.06 (rounded to 8) out of a possible 23 points.

[CMI Component Score for RESC]=([23]/[3 Year CMI Max Across All Hospitals])×[3 Year Average CMI of Target Hospital]

Step 8. Calculate the MVI Component Score for RESC. Using the results, of the calculations in the preceding, steps, one can now add the RESC quality component and Hospital AVG CHG component and CMI component for RESC scores together. The resulting score ranges from 0 to 230. In the current example a score of 169 is achieve for RESC.

[RESC Component Score]=[RESC Quality Component Score]+[AVG CHG Component Score]+ [CMI Component Score for RESC]

Measurement Period Data:

The "Measurement Period" is the most current 12-month period in the full data period range. The reporting period of the source data for Metric 6, RESC is typically a year. Thus with RESC, the "Measurement Period" data consists of 1 year of charges (or costs) and case counts for each of the Top 5 clinical service (Orthopedics. GI etc.) areas defined by MDCs with the highest charges (or costs). See FIG. 32.

The four quarters of Aggregated Neurology Cases, as the example, from DHMC (2012Q4-2012Q1) totaled $3,302,922 for 92 cases or $36,032 Per-Case Charges. This will be compared to the average charges during the previous two years of "Back Period" data.

Back Period Data:

Back Period data is the range of data that chronologically comes before (older than), the "Measurement Period" in the full data period range. As mentioned with the "Measurement Period" data, the reporting period of the source data for Metric 6, RESC is typically a year. The "Back Period" data consists of 2 or more years of charges (or costs) and case counts for each of the Top 5 clinical service areas (Respiratory, Cardiology etc) defined by MDCs with the highest charges (or costs), see FIG. 33.

The eight quarters of Aggregated Neurology data from DHMC (2011-2010) averaged $37,054 Per-Case charges for 194 cases. These are the aggregated data, which when compared to the 2012, "Measurement Period" data ($32,032) documents the Delta—$1,022 (FIG. 31) change (reduced numbers of resources consumed by Neurology) by −2.76% (FIG. 31).

Using MVI Scores to Distribute Hospitals' and Physicians' Financial Savings

The second essential feature of the MVI's capabilities is to objectively document and distribute hospitals' and physicians net-saving, if clinical quality and operational improvements have actually produced net savings. This function is different from the first feature, described in Section I & II, of calculating MVI scores to quantify hospitals' trended improvements. This first function only records improvements or degradations in financial outcomes (charges or costs) at the clinical service and hospital levels. It is the means by which the MVI graphs are constructed that are used to compare hospitals' performances.

This second function quantifies the specific dollar amounts attributable to each metric that is improved to achieve a net-savings in order to reimburse (bonus) hospitals and physicians. This demonstration will calculate MVI scores at the clinical service levels, meaning the physicians who work in that service i.e. orthopedics, who will share equally in the saving. (Measuring each physician's efficiencies is optimal but often not practicable, because it requires the hospital to have 4 years of fully allocated cost data plus an equal number of years with Computerized Physician Order Entry (CPOE) to capture each resource consumption entry.)

Financial Projection:

The process of determining the savings available for distribution begins with a projection based upon prior data. Specifically the trend of per encounter charges (or costs) across the back data periods is determined and they projected to the measurement period. See FIG. 34. The projection represents the estimate of the per-encounter charges (or costs) in the ensuing "measurement year" that would exist if no improvements in clinical and financial methods are achieved. However the goal of clinical process improvement activities is to initiate clinical and operational changes that result in a downward bending of the cost curve as graphically demonstrated by the color lines. (For instance, if significant efficiencies are achieved during the measurement period, as evidenced by the same number of resources having been expended in the measurement period as were expended in the previous year, the curve would be bent down to the number 3 [blue line]. This is arbitrarily considered to be a 100% improvement. (Naturally, the curve could actually be reduced even further to line 4 [T110] or black line.)

The "measurement year" changes are the resultant of either greater or decreased efficiencies. The difference between these charges and the projected charges becomes the savings or loses. A change-goal is prospectively determined, which becomes the target (usually 50% improvement). Thus MVI targets levels of change in the measurement period. The target levels help to perform early analysis of savings potentials prior to having all the measurement period data being in-hand. With the target as the anticipated or goal change, the actual change, at the end of the "measurement year" is a recording of what objectively took place during the measurement period once all data for measurement period is collected. The savings is the difference between the projected level and the actual measurement period result. The net saving (or change from the projection) is the driver of the amount that can be distributed to the hospital and physicians under risk-sharing arrangements. Note the projection can be driven against charges or costs depending on the level available. If charges are used, as is generally the case as costs are often not available, they will eventually get converted to costs using charge to cost ratios as part of the process of awarding bonuses.

To calculate the financial projection, aggregate the per encounter charge (or cost) data for each of the top 5 service areas for each of the back periods (typically each period is a year). The top 5 services areas are the same ones determined in the MVI calculations. A sixth service is also often included, called "Other", which records values for the remaining clinical service areas not already represented by the top 5. The data gathered for these service areas includes the total charges or costs), total number of encounters (a.k.a total cases), and average charge (or cost) Per-Case. See FIG. 35.

Once the back year Per-Case dollars have been gathered, the projection can be calculated. The projection calculated from adjusting the per-case dollars of the most recent back year by applying, the average percent change across the back years. However the percent change calculation is controlled by an agreed upon ceiling figure, in this example 20%. This calculation is done for each service and overall. Additionally, a Case Projection Modifier Ratio is included, defaulted to 1, to allow adjustments to the projection if case levels are significantly changed from the assumed back year carry over. See FIG. 36.

The difference between the projection (Pd. Total Chrg 2012) and the Actual Charges, which is calculated next, provides the savings for loss). Ideally the anticipated improvement efforts will yield a 50% or more decrease from the projection. These anticipated improvement situations could be determined in like manner by defining a change that identifies the organizations predetermined goals. The projected value—the target value (Tgt. Total Chrg 2012) represents the potential targeted savings. See FIG. 37.

The purpose of calculating a "Target Total Charge Value" is to prospectively demonstrate to the providers their potential bonuses if they participate in clinical quality and cost efficiency improvement efforts that improve outcomes. (Note in FIG. 34, the Target is represented by the solid line, which is a 50% improvement) At the beginning of the measurement period, the exact number of cases during that year cannot be known, therefore an assumption is made that the number of "Tgt # Cases" is equal to the previous year.

The difference that determines the bonuses is the result of the actual data that is gathered retrospectively at the completion of the measurement period. The projection actual values provide the overall saving to be distributed. See FIG. 38 and FIG. 39. (Note the Actual 2012 [Act. Total Chrg 2012] represents an improved performance [greater savings] over the target [Target 2012]).

At the end of the measurement period, the Actual Charges for each clinical area times the actual number of cases equals the Actual Total Charges. In this example it is $454,660,373.

The difference between the Projected 2012 Total Charges, Facility Inpatient ($505,403,1170) and the Actual 2012 Total Charges is the Projected minus Actual ($50,742,744). These are the gross charges that are available for distribution.

Costs Vs. Charges:

The final savings calculations for bonus distributions are based on costs. Charges are generally used in place of costs in the early portions of the calculation and are then converted to costs at the appropriate times. (Hospitals are relatively accurate in determining charges for their reimbursements. Costs may or may not be accurate in most hospitals.) if accurate cost data are not available, it is important to ascertain the cost to charge ratios for the hospital to accomplish this conversion. See FIG. 40.

Optionally one may use an array of ratios dedicated to each service area to improve and refine cost conversion. Ideally all dollars are in actual costs from the start. When costs are available the cost ratio simply becomes 100% and just the fixed costs have to be accounted for.

Participating Physicians:

The physicians are at the center of the clinical improvements that are measured by the MVI and drive the change in the cost curve. The next step is to determine the participating physicians and the service lines they are most closely associated with to help determine the proportions of savings for each physician. See FIG. 41.

Physician are considered part of specific top service group if they the responsible MD for 1% or more of the total cases in the respective service area; otherwise they are considered part of the "Other Clinical Service" group.

Quality Metrics (MVI):

The MVI quality metrics, discussed in detail in Section II, are used to index the clinical improvements and drive the level of savings each physician is entitled to. See FIG. 42.

In the example used here, physicians' bonuses for improvements in quality components scores 1, 2 and 3 (QMPS, RADM, MORT) are hospital-wide measures; therefore the bonuses are equally divided among all physicians (104 MDs FIG. 41). Quality components scores 4 and 5 (MORB, RIV) are divided equally across just the participating physicians in the Top 5 Inpatient Facility Service areas, (29 MDs FIG. 41). However, there is an alternative to this equal sharing method. At the end of the Measurement Year, to reflect the fact that the cardiologists, for example, improved their quality indicators more than the orthopedic surgeons, these computations may be done separately for each service to avoid equal sharing.

Component score RESC is special in that a RESC bonus is implied through the spending reduction related distributions including the Value Share discussed later.

The following sub sections show how each of the quality metrics is used to determine separate bonus levels if improvements have been achieved.

QMPS (Quality Measures & Patient Satisfaction) Bonus Factor:

The QMPS score is determined by the performance of the entire hospital and medical staff. Therefore, physicians bonuses are divided among all participating physicians. The Medical Value Index Score is a composite score computed from information aggregated by the hospital.

To determine the QMPS bonus per MD, the component score (Medical Value Index Score, see FIG. 43 is translated into the bonus rate, a factor used to amplify the bonus. The Bonus Rate Max is a value that is modified over time with experience and "3.00" is the amount used if the component score (Score Range) is at the maximum (46). See FIG. 43.

In order to translate the hospital's QMPS Score to a dollar amount for potential bonus distributions, a sliding scale is built against the projection dollars for the top 5 service areas using 2% reduction increments. The actual top 5 service area dollars for the measurement year are then compared to the scale to determine a bonus level. The bonus level increases in proportion to the greater financial improvements as measured by the difference between actual and projected. The bonus level is computed by multiplying the spending, level by a Y %, determined through comparison of current spending level to the projection based sliding scale. The Y % scale values used to generate the bonus levels are designed to be adjusted over time to best match bonus levels to the respective MVI component score expectations. Furthermore, the bonus level is then multiplied by the bonus rate to determine the overall bonus amount for QMPS. The bonus amount (Total Bonus) is divided by the number of participating physicians in order to determine the Bonus per MD. See FIG. 44.

RADM (Readmission) Bonus Factor:

The RADM rate is determined by the performance of the entire hospital and cannot be attributed to a single clinical service. Therefore, like the QMPS bonus, the RADM is divided among all participating physicians. The Medical Value Index Score is the Readmission Rate computed by the hospital.

To determine the RADM bonus per MD, the component score (Medical Value Index Score, see FIG. 45, a factor used to amplify the bonus. The bonus rate max is a value that is modified over time with experience and is the amount used if the component score (Score. Range) is at its maximum (80). See FIG. 45.

To convert the hospital readmission rate to a dollar figures, a sliding scale is built against the projection dollars for the top 5 service areas using 2% reduction increments. The actual top 5 service area dollars for the measurement year are then compared to the scale to determine a bonus level. The bonus level increases the greater the difference between actual and projected. The bonus level is computed by multiplying the spending level by a Y % determined through comparison of current spending level to the projection based sliding scale. The Y % scale values used to generate the bonus level are designed to be adjusted over time to best match bonus levels to the respective MVI component score expectations. Furthermore, the bonus level is then multiplied by the bonus rate to determine the overall bonus amount for RADM. This bonus amount is divided by the number of participating physicians in order to determine the bonus per MD. See FIG. 46.

MORT (Mortality Rate) Bonus Factor:

Mortality rates are influenced by the overall performance of the entire hospital and not to a single clinical service. The bonuses are therefore equally divided among the physicians. To determine the MORT bonus per MD, the component score (Medical Value Index Score, see FIG. 47, is translated into the bonus rate (Index %), a factor used to amplify the bonus. The bonus rate max is a value that is modified over time with experience and is the amount used if the component score (Score Range) is at the maximum (144). See FIG. 47.

To equate reductions (improvements) in mortality rates to dollar bonuses, a sliding scale is built against the projection dollars for the top 5 service area using 2% reduction increments. The actual top 5 service area dollars for the measurement year are then compared to the scale to determine a bonus level. The bonus level increases the greater the difference between actual and projected. The bonus level is computed by multiplying the spending level by a Y % determined through comparison of current spending, level to the projection based sliding scale. The Y % scale values used to generate the bonus level are designed to be adjusted over time to best match bonus levels to the respective MVI component score expectations. Furthermore, the bonus level is then multiplied by the bonus rate to determine the overall bonus amount for MORT. This bonus amount is divided by the participating physicians in order to determine the bonus per MD. See FIG. 48.

MORB (Morbidity Rate) Bonus Factor:

To determine the MORB bonus per MD, the component score (Medical Value Index Score, see FIG. 49, is translated into the bonus rate (Index %), a factor used to amplify the bonus. The Bonus Rate Max is a value that is modified over time with experience and is the amount used if the component score is at maximum Score Range (174). See FIG. 49.

In order to convert the reduction (improvements) in Morbidity Rates to dollars for bonuses, as determined by the Bonus Rate, a sliding scale is built against the projection dollars for the top 5 service areas using 2% reduction increments. The actual top 5 service area dollars for the measurement year are then compared to the scale to determine a bonus level. The bonus level increases the greater the difference between actual and projected. The bonus level is computed by multiplying the spending, level by a Y % determined through comparison of current spending level to the projection based sliding scale. The Y % scale values used to generate the bonus level are designed to be adjusted over time to best match bonus levels to the respective MVI component score expectations. Furthermore, the bonus level is then multiplied by the bonus rate to determine the overall bonus amount for MORB. This bonus amount is divided by the participating physicians to determine the bonus per physician. See FIG. 50.

RIY (Reduction in Variation) Bonus Factor:

To determine the RIND bonus per MD, the component score (Medical Value Index Score, see FIG. 51, is translated into the bonus rate (Index %), a factor used to amplify the bonus. The bonus rate max is a value that is modified over time with experience and is the amount used if the component score is at its maximum level. (126) See FIG. 51.

In order to convert the Reductions In Variation (improvements) to dollars for bonuses, as determined by the Bonus Rate, a sliding scale is built against the projection dollars for the top 5 service areas using 2% reduction increments. The actual top 5 service area dollars for the measurement year are then compared to the scale to determine a bonus level. The bonus level increases the greater the difference between actual and projected. The bonus level is computed by multiplying the spending level by a Y % determined through comparison of current spending level to the projection based sliding, scale. The Y % scale values used to generate the bonus level are designed to be adjusted over time to best match bonus levels to the respective MVI component score expectations. Furthermore, the bonus level is then multiplied by the bonus rate to determine the overall bonus amount for RIV. This bonus amount is divided by the participating physicians to determine the bonus per MD. See FIG. 52.

RESC (Resource Consumption Rate) Bonus Factor:

RESC measures a reduction in the rate of Resource Consumption, as defined by dollars, needed to treat a relatively homogeneous cohort of patients. A declining for increasing) rate, which is translated into the component score (Medical Value Index Score, see FIG. 53, determines a hospital's and medical staff's net saving or lack thereof. See FIG. 54.

Physician Bonus Distribution:

The per physician bonus amounts calculated by application of the MVI scores are aggregated across the breakdown of participating, physicians and the associated service areas. Bonus for "Top Service" MDs are determined by all five of the MVI Metrics QMPS, RADM, MORT, MORB, & RIV. Bonus for "Other" MDs determined only from MVI Metrics QMPS, RAM & MORT as these are hospital-wide measures used to reimburse physicians whose practices represent a smaller portion of inpatient charges (or costs) and are outside the patient cohorts contained in the "Top Service" areas.

The dollar calculations for physicians' bonuses must be converted to cost along with an accounting of the fixed costs using the ratios presented earlier. (Optionally one may use an array of ratios dedicated to each service area to improve and refine cost conversion.) As previously stated, in an ideal situation, all dollars would be in actual costs across all back and measurement years but this is usually not the case. If or when actual costs are available, the conversion becomes a one to one computation and just the fixed costs have to be accounted for. See FIG. 55.

Net Savings:

As previously noted, the gross savings is determined from the comparison of the measurement period actuals vs. the spending projection. The MVI calculations have been used to index the improvements and determine the physician bonuses, which can be modified through changes in each component score's computations. The calculations can be brought together to determine the net savings. The net savings are the savings after taking the gross reduction (savings) and accounting for costs and bonus due to physicians for their measured quality improvements. See FIG. 56.

Optionally one may use an array of ratios dedicated to each service area to improve and refine cost conversions.

Distribution of Value Share (VSHARE) Dollars:

Once the Cost Adjusted Net Savings has been determined, the final step is to determine how the Net Savings is distributed, if the hospital and physicians are participating; in a risk-sharing initiative. The distribution is called the Value Share (VShare) and is distributed back to the hospital administration and physicians. For the physicians this is a financial bonus amount over and above, the bonus they earned from direct and measured clinical quality improvements. The proportion that the physicians receive vs, the hospital administration is driven by it scale that increase the share to the physicians the greater the overall financial savings. (These percentages are predetermined by the hospital and physicians and reflect the fact that it is the physicians' ordering pens that primarily drive a hospital's consumption of resources.) See FIG. 57.

In this example, the Cost Adjusted Net Savings is $5,273,701 as noted in FIG. 56. That amount is applied to the sliding scale in FIG. 57 to determine the distribution of savings between the hospital (45%) and physicians (55%), as noted in FIG. 57.

The VShare to the physicians is broken down and distributed by proportion to the gross savings and the respective service areas. See FIG. 58.

Given that the VShare is a final and additional distribution to the physicians, the total distribution to the physicians is represented by their bonuses plus the VShare amount. See FIG. 59.

Summary:

The final results of the calculations are presented to the hospital and participating physicians. The total amounts per MD and per hospital are summarized and reported. The process is repeated each year after the initial measurement year calculation has been completed. See FIG. 60.

A Summary Overview of the MVI Process:

At the beginning of the project, which is generally the beginning of the measurement period, the back data is collected and processed to determine the financial projection that is the agreed upon estimate of the future without further improvements. Immediately after the close of the measurement year, the actual data is gathered to both fill in the actual values and compute the MVI against the measurement year. The value-sharing computations are then completed for the measurement year as described throughout.

Assuming that clinical and financial outcomes have improved and that the hospital and physicians are participating in a risk-sharing initiative, the hospital will realize its newfound savings and the participating physicians are rewarded for their part in the effort. Without a qualified risk-sharing arrangement, all financial benefits will accrue to the hospital.

For the following year, the cycle continues with the previous measurement year moving into a back year status and the current period becoming the new measurement year. At the close of the new 12-month period, the value sharing calculations will be repeated to recognize and reward improvements. This represents a yearly process for recognizing and rewarding continuous quality and cost efficiency improvements the essence of value-based healthcare delivery and purchasing.

INDUSTRIAL APPLICABILITY

The present invention has the following capabilities conferring upon it comprehensive industrial applicability:

- Utilize Verras' technologies (AIM, Sherlock, Watson) to quantify, score and graph the major metrics of quality of multiple clinical quality and efficiency outcomes to statistically determine if there have been improvements, degradations or static outcomes over at least a 3 or more-years. (AIM, Sherlock and Watson are Verras' supporting technologies but are not included in the MVI patent.)
- Utilize Sherlock to demonstrate charge and LOS variations then differentiate the more efficient patients' from those with less efficient outcomes then aggregate these patients' data using Watson's technology to drill down into each patient's clinical and operational level data (lab, pharmacy, x-ray etc.) in order for MVI to quantify improvements or degradations in outcomes that are to be displayed by the MVI graphs.
- Simplify the interpretations of individual MVI metrics, by stacking each of the component bars to create a single MVI bar graph representing a hospital's Total MVI Score.
- Assign each component metric with different weighting factors based on 30 years and hundreds of hospitals experiential evidence, to express which metrics are the most predictive of actual clinical quality and cost efficiency improvements.
- Use the different weighting factors to assign maximum numeric scores for each MVI metric of quality then quantify each hospital's outcomes score and express them as a percentage of the maximum score in order for MVI to differentiate their relative contributions to the overall measure of healthcare quality for hospitalized patients.
- Create an MVI bar that is positive (higher), either directly by inversion or through sliding scales, to express improving quality or efficiencies when actual improvements are smaller as expressed by negative numbers such as seen with these outcomes: Re-Admission (RADM) and Mortality (MORT) and Morbidity (MORB) rates, Reductions in Variation (RIV) and Resource Consumption 'charges or costs' (RESC).
- Aggregate and trend multiple clinical quality and efficiency outcome measures to statistically determine if there have been improvements, degradations or static outcomes over at least a 3-year period,
- Aggregate and trend federally defined quality measures of National Hospital Quality Measures (NHQM) and Hospital Consumer Assessment of HealthCare Providers and Systems (HCAHPS) and determine each hospital's ability to document statistically significant improvements trended over a three-year period as one score (QMPS), which is a percentage of the total possible points (46) allocated to the QMPS.
- Incorporate a composite measure, such as readmission rates (RADM) of thirty (30)-day re-admission rates for AMI, HF, and PN as calculated by CMS using claims data it receives directly from the hospital.
- Objectively Document All Major Metrics of Hospitals' Quality and Cost Efficiency Improvements (Value) over Three or More Years and graphically demonstrate each metric's contribution as component parts of the MVI's bar graph that demonstrate the overall quality of the institution as represented by the hospital's Total MVI Score.
- Objectively Document All Major Metrics of Quality and Cost Efficiency Improvements (Value) for each clinical service (orthopedics, cardiology etc.) over three or more years and graphically demonstrate each metric's contribution as stacked component parts of the MVPs bar graph to demonstrate the overall quality of the entire hospitals and of each clinical service.
- Objectively and transparently quantify multiple hospitals and medical staff's clinical and financial outcomes using multiple MVI Bar Graphs in order for healthcare purchasers and patients to compare hospitals' outcomes.
- Incorporate into MVI additional metrics of quality in a sixth, seventh or more (optional) outcomes whose trends are computed separately using Verras MVI algorithms to determine the "score" for each of the optional outcomes by comparing each outcome's metric score to the empirically derived, maximum score then recorded as a percentage.
- Incorporate each hospital's reported, average three-year Case Mix Index in order to compare hospitals' outcomes in any geographic area so as not to penalize the tertiary and quaternary hospitals with more complex cases,
- Incorporate each hospital's actual, three-year, average Charges Per-Case for healthcare purchasers and providers to have some rough idea as to the relative prices being charged for medical service rendered.
- Grade and score the trends of nine (9) risk-adjusted mortality rates, by comparing the hospital's actual rate to regional risk-adjusted norms, which include an overall mortality rate (all-MDC rate), a mortality rate for each of the top 5 clinical service areas (top 5 MDCs with the highest charges or costs), and the three publically reported Thirty (30) Day mortality rates defined by CMS.
- Measurement and score a hospital's morbidity (complications) rate using a monitor on length of stay when the observed. LOS is 4 or more days longer than the patients' risk-adjusted norms for the hospital's 10 MS-DRGs with the greatest number of charges.
- Calculate the statistically significant reduction in charge (or cost) variations (RIV) for the top 5 MS-DRGs (charges or costs) in each of the top 5 MDCs with the highest numbers of resource consumptions in dollars (charges or costs) and convert the RIV to a positive score for the MVI bar graph.
- Determine if fewer or greater numbers of resources were consumed over time when comparing the measurement data period to the back data (previous years) period for the Top 5 clinical service areas (those with the highest numbers of resource consumptions in charges (or costs) dollars and converting the negative trends to positive for MVI presentation for a given hospital using each hospital's Uniform Discharge Data Set (UHDDS) or public data such as CMS MedPAR data for inter-hospital comparisons.
- Determine, at the end of the measurement year, calculate the actual net-savings and rewards for each hospital and it medical staff, based on their projected clinical and financial outcomes for use by federal or commercial bundled or global payment initiatives, such as a single or multiple hospital accountable care organization (ACO).
- Quantify inpatient quality and efficiency outcomes of each hospital in order to differentially distribute net saving between the hospital and medical staff members who are at-risk under Medicare or other value-based payment models.

Quantify inpatient quality and efficiency outcomes of individual clinical services (Cardiology, Orthopedics, Hospitalists) in order to differentially reimburse the hospital and its physician services which are at-risk under Medicare or other value-based payment models.

Quantify inpatient quality and efficiency outcomes of individual physicians in order to differentially reimburse the hospital and individual physicians who are at-risk under Medicare or other value-based payment models.

Calculate the net-saving attributable to the physicians quality and cost efficiency improvements, combining the value share (overall efficiencies) portion with the bonuses attributable to each clinical services quality and efficiency Outcomes to assess the total bonuses received by each clinical service and each physician.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The above description, together with the objects of the invention and the various features of novelty which characterize the invention, are pointed out with particularity in the claims annexed to and forming part of this disclosure. For a better understanding of the invention, its operating advantages and the specific advantages attained by its uses, reference should be made to the accompanying drawings and descriptive matter in which there are illustrated preferred embodiments of the invention.

Furthermore the purpose of the foregoing abstract is to enable the U.S. Patent and Trademark Office and the public generally, and especially the scientists, engineers, and practitioners in the art who are not familiar with patent or legal terms or phraseology, to determine quickly from a cursory inspection, the nature and essence of the technical disclosure of the application. The abstract is neither intended to define the invention of the application, which is measured by the claims, nor is it intended to be limiting as to the scope of the invention in any way.

We claim:

1. A computer implemented, web-based method for calculating a medical value index of healthcare performance measurement for one or more healthcare providers comprising:
    (a) searching one or more computer databases and one or more computer network memory for medical information from hospital patients charts data, hospital medical records and hospital department data, insurance company data government data and physician's office data;
    (b) gathering, compiling and aggregating said medical information from hospital patient charts data, hospital medical records and hospital department data, insurance company data, government data and physician's office data wherein said aggregation of data includes the use of a Sherlock computer program sub-system and memory database which targets cases by type, physician, severity and clinical services, diagnoses and procedures at a revenue code level, and use of resources;
    (c) using the aggregated gathered compiled data or calculating the following quality metric scores:
        (i) Quality Measures and Patient Satisfaction (QMPS);
        (ii) Composite Re-Admission Rate (RADM);
        (iii) Risk Adjusted Mortality Rate (MORT);
        (iv) Risk Adjusted Morbidity Rate (MORB);
        (v) Reduction In Variation (RIV); and
        (vi) Resource Consumption (RESC);
    wherein said Sherlock computer sub-system aggregated data is further analyzed by a Verras Watson based computer sub-system which explains diagnoses and procedures by whom by specific physician, what and win, sequence of events, and what was not documented, explains specific resources by specific type of tests, breakdown of drugs, identifies why extra days were spent in hospital, and converts charges to true costs, and creates a best practices framework by database of clinical variation by diagnosis and procedure, establishes a computerized physician order entry (CPOE) customization and facilitates clinical pathway construction; and
    (d) calculating a medical value index (MVI) for each healthcare provider by adding the quality metric scores for each of the six metrics.

2. The computer implemented, web-based method for calculating a medical value index of healthcare performance measurement for one or more healthcare providers, according to claim 1, wherein said Quality Measures and Patient Satisfaction (QMPS) metric score is calculated for a specified measurement period timeframe and a back period timeframe using National Hospital Quality Measures (NHQM) data and Patient Satisfaction (CMS) data mandated to be supplied to the US federal government from all hospitals.

3. The computer implemented, web-based method for calculating a medical value index of healthcare performance measurement for one or more healthcare providers, according to claim 1, wherein said Composite Re-Admission Rate (RADM) metric score is calculated for a specified measurement period timeframe and a back period timeframe using hospital composite re-admission rate data for all business, all MD categories and all services, routinely collected by hospitals.

4. The computer implemented, web-based method for calculating a medical value index of healthcare performance measurement for one or more healthcare providers, according to claim 1, wherein said Risk Adjusted Mortality Rate (MORT) metric score is calculated for a specified measurement period timeframe and a back period timeframe using hospital risk adjusted Mortality rate data for all business, all Payers, all MD categories and all services.

5. The computer implemented, web-based method for calculating a medical value index of healthcare performance measurement for one or more healthcare providers, according to claim 1, wherein said Risk Adjusted Morbidity Rate (MORB) metric score is calculated for a specified measurement period timeframe and a back period timeframe using hospital risk adjusted morbidity complication rate data for all business, all Payers all MD categories and all services.

6. The computer implemented, web-based method for calculating a medical value index of healthcare performance measurement for one or more healthcare providers, according to claim 1, wherein said Reduction In Variation (RIV) of charges/costs metric score is calculated for a specified measurement period timeframe and a back period timeframe using, hospital data for all payers, top drugs by dollar amounts and selected services.

7. The computer implemented, web-based method for calculating a medical value index of healthcare performance measurement for one or more healthcare providers, according to claim 1, wherein said Resource Consumption (RESC) of charges/costs metric score is calculated for a specified measurement period timeframe and a back period timeframe using hospital data for all payers, all dines used and selected services used.

8. The computer implemented, web-based method for calculating a medical value index of healthcare performance measurement for one or more healthcare providers, according to claim 6, wherein the mean variation and its statistical significance of said Reduction In Variation (RIV) is calculated as the Delta Variation for the Measurement Period versus the Back Period, as follows:

[Delta Variation]=[Measurement Period Variation]–[Back Period Variation]

and the Variation Confidence Interval Upper and Lower Limits for both the Measurement Period and Back Period is calculated as a confidence interval of a standard deviation a chi squared distribution, as follows:

$$[VCI \text{ Upper Limit}] = \sqrt{\frac{([\# \text{Cases}] - 1) \times [\text{Variation}]2}{CHINV(0.025, [\# \text{Cases}] - 1)}}$$

$$[VCI \text{ Lower Limit}] = \sqrt{\frac{([\# \text{Cases}] - 1) \times [\text{Variation}]2}{CHINV(0.975, [\# \text{Cases}] - 1)}}.$$

9. The computer implemented, web-based method for calculating a medical value index of healthcare performance measurement for one or more healthcare providers, according to claim 8, wherein said Reduction In Variation (RIV) is graphically illustrated over a 3-year period using ovals that encircle two standard deviation charges and length of stay (LOS) volume of cases each year, for a given clinical condition.

10. The computer implemented, web-based method for calculating a medical value index of healthcare performance measurement for one or more healthcare providers, according to claim 7, wherein said Resource Consumption (RESC) quality metric is calculated using the Delta Per-Case Charge for the Measurement Period versus the Back Period, as follows:

[Delta Per-Case Charge]=[Measurement Period Per-Case Charge]—[Back Period Per-Case Charge]

and calculating the Per-Case % Change by dividing the Delta Per-Case Charge by the Per-Case Charge of the Back Period, as follows

[Per-Case % Change]=[Delta Per-Case Charge]/[Back Period Per-Case Charge].

11. A computer implemented, web-based method, according to claim 1, for using a calculated medical value index of healthcare performance measurement for equitable provider reimbursement comprising:
 (a) calculating a medical value index (MVI) for each healthcare provider by adding the quality metric scores for each of the six metrics;
 (b) generating value sharing computations and calculating overall gross and net savings; and
 (c) calculating an equitable proportional distribution of said net savings to physicians, hospitals, Accountable Care Organizations (ACOs), CO-OPs and insurers in the form of physician bonuses and healthcare provider facility reimbursements.

12. A computer implemented web-based method, according to claim 11, for using a calculated medical value index of healthcare performance measurement for equitable provider reimbursement wherein said step of generating value sharing computations and calculating, overall gross and net savings includes graphically illustrating, charge/cost projections for inpatient charges per patient, tabulating back year dollars per case and projections from historical percent change for all service areas, tabulating target from percent change totals and actual results of measurement period for all service areas, and arriving at a gross and net savings for the hospital and each clinical service area.

13. A computer implemented, web-based method, according to claim 11, for using a calculated medical value index of healthcare performance measurement for equitable provider reimbursement wherein said step of calculating an equitable proportional distribution of said net savings to physicians includes using said MVI quality metric scores to calculate physician bonuses by quality metric, to arrive at bonuses to be distributed to all participating physicians.

14. A computer implemented, web-based method, according to claim 13, for using a calculated medical value index of healthcare performance measurement for equitable provider reimbursement wherein said step of calculating an equitable proportional distribution of said net savings to physicians includes distributing said calculated physician bonuses based upon clinical service areas.

15. A computer implemented, web-based method, according to claim 11, for using a calculated medical value index of healthcare performance measurement for equitable provider reimbursement wherein said step of generating value sharing computations includes calculating, cost adjusted net savings, generating value share distribution percentages based on net savings ranges, calculating physician value share breakdowns, total physician dollars to be distributed and yearly calculations and summary of physician hospital value sharing distributions.

\* \* \* \* \*